(12) United States Patent
Pons

(10) Patent No.: US 7,968,690 B2
(45) Date of Patent: Jun. 28, 2011

(54) AGONIST ANTI-TRKC ANTIBODIES AND METHODS USING SAME

(75) Inventor: Jaume Pons, San Bruno, CA (US)

(73) Assignee: Rinat Neuroscience Corp., South San Francisco, CA (US)

(*) Notice: Subject to any disclaimer, the term of this patent is extended or adjusted under 35 U.S.C. 154(b) by 932 days.

(21) Appl. No.: 10/584,443

(22) PCT Filed: Dec. 23, 2004

(86) PCT No.: PCT/US2004/043435
§ 371 (c)(1),
(2), (4) Date: Aug. 17, 2007

(87) PCT Pub. No.: WO2005/062955
PCT Pub. Date: Jul. 14, 2005

(65) Prior Publication Data
US 2009/0202526 A1    Aug. 13, 2009

Related U.S. Application Data

(60) Provisional application No. 60/532,592, filed on Dec. 23, 2003.

(51) Int. Cl.
*C12P 21/08* (2006.01)
*C07K 16/00* (2006.01)
*A61K 39/395* (2006.01)
*A61K 39/00* (2006.01)

(52) U.S. Cl. .............. 530/388.1; 530/387.1; 530/387.3; 424/130.1; 424/133.1; 424/141.1

(58) Field of Classification Search .................. None
See application file for complete search history.

(56) References Cited

U.S. PATENT DOCUMENTS

| | | | |
|---|---|---|---|
| 3,773,919 A | 11/1973 | Boswell et al. | 424/19 |
| 4,485,045 A | 11/1984 | Regen | 260/403 |
| 4,544,545 A | 10/1985 | Ryan et al. | 424/1.1 |
| 4,676,980 A | 6/1987 | Segal et al. | 424/85 |
| 4,777,127 A | 10/1988 | Suni et al. | 435/5 |
| 4,816,567 A | 3/1989 | Cabilly et al. | 530/387 |
| 5,013,556 A | 5/1991 | Woodle et al. | 424/450 |
| 5,047,335 A | 9/1991 | Paulson et al. | 435/69.1 |
| 5,219,740 A | 6/1993 | Miller et al. | 435/69.6 |
| 5,225,539 A | 7/1993 | Winter | 530/387.3 |
| 5,278,299 A | 1/1994 | Wong et al. | 536/53 |
| 5,422,120 A | 6/1995 | Kim | 424/450 |
| 5,500,362 A | 3/1996 | Robinson et al. | 435/7.23 |
| 5,510,261 A | 4/1996 | Goochee et al. | 435/240.2 |
| 5,530,101 A | 6/1996 | Queen et al. | 530/387.3 |
| 5,545,806 A | 8/1996 | Lonberg et al. | 800/2 |
| 5,545,807 A | 8/1996 | Surani et al. | 800/2 |
| 5,569,825 A | 10/1996 | Lonberg et al. | 800/2 |
| 5,580,859 A | 12/1996 | Felgner et al. | 514/44 |
| 5,585,089 A | 12/1996 | Queen et al. | 424/133.1 |
| 5,604,202 A | 2/1997 | Kessler et al. | 514/12 |
| 5,625,126 A | 4/1997 | Lonberg et al. | 800/2 |
| 5,633,425 A | 5/1997 | Lonberg et al. | 800/2 |
| 5,661,016 A | 8/1997 | Lonberg et al. | 435/172.3 |
| 5,693,761 A | 12/1997 | Queen et al. | 536/23.53 |
| 5,693,762 A | 12/1997 | Queen et al. | 530/387.3 |
| 5,750,373 A | 5/1998 | Garrard et al. | 435/69.4 |
| 5,807,715 A | 9/1998 | Morrison et al. | 435/69.6 |
| 5,814,482 A | 9/1998 | Dubensky, Jr. et al. | 435/69.3 |
| 5,821,337 A | 10/1998 | Carter et al. | 530/387.3 |
| 5,866,692 A | 2/1999 | Shitara et al. | 536/23.1 |
| 5,981,568 A | 11/1999 | Kunz et al. | 514/411 |
| 5,997,867 A | 12/1999 | Waldmann et al. | 424/154.1 |
| 6,180,370 B1 | 1/2001 | Queen et al. | 435/69.6 |
| 6,331,415 B1 | 12/2001 | Cabilly et al. | 435/69.6 |
| 6,548,640 B1 | 4/2003 | Winter | 530/387.1 |
| 7,306,793 B2 | 12/2007 | Haddada et al. | 424/93.2 |
| 7,384,632 B2 | 6/2008 | Devaux et al. | 424/142.1 |
| 2004/0137513 A1 | 7/2004 | Devaux et al. | |
| 2005/0089521 A1 | 4/2005 | Shelton | 424/146.1 |
| 2007/0014786 A1* | 1/2007 | Shelton | 424/133.1 |
| 2007/0036794 A1* | 2/2007 | Devaux et al. | 424/146.1 |

FOREIGN PATENT DOCUMENTS

| | | |
|---|---|---|
| EP | 0345242 | 2/1989 |
| EP | 0524968 | 6/1995 |
| GB | 2200651 | 8/1988 |
| WO | WO8704462 | 7/1987 |
| WO | WO9007936 | 7/1990 |
| WO | WO9011092 | 10/1990 |
| WO | WO9100360 | 1/1991 |
| WO | WO9100904 | 1/1991 |
| WO | WO9102805 | 3/1991 |
| WO | WO9114445 | 10/1991 |
| WO | WO9220373 | 11/1992 |
| WO | WO9303769 | 3/1993 |
| WO | WO9310218 | 5/1993 |

(Continued)

OTHER PUBLICATIONS

Rudikoff, Giusti, Cook, and Scharff. Single amino acid substitution altering antigen-binding specificity. Proceedings of the National Academy of Sciences, 1982. vol. 79, pp. 1979-1983.*

Mac Callum, Martin, and Thornton. Antibody-antigen interactions: contact analysis and binding site topography. Journal of Molecular Biology, 1996. vol. 262, pp. 732-745.*

De Pascalis, Iwahashi, Tamura, Padlan, Gonzales, Santos, Giuliano, Schuck, Schlom, and Kashmiri. Grafting of abbreviated complementarity determining regions containing specificity determining residues essential for ligand contact to engineer a less immunogenic humanzied monoclonal antibody. Journal of Immunology, 2002. vol. 169, pp. 3076-3084.*

Casset, Roux, Mouchet, Bes, Chardes, Granier, Mani, Pugniere, Laune, Pau, Kaczorek, Lahana, and Rees. A peptide mimetic of an anti-CD4 monoclonal antibody by rational design. Biochemical and Biophysical Research Communications, 2003. vol. 307, pp. 198-205.*

(Continued)

*Primary Examiner* — Anne M. Gussow
(74) *Attorney, Agent, or Firm* — Pfizer Patent Dept.

(57) ABSTRACT

The invention concerns agonist anti-trkC antibodies, polypeptides, and polynucleotides encoding the same. The invention further concerns use of such antibodies, polypeptides and/or polynucleotides in the treatment and/or prevention of neuropathies, such as sensory neuropathies, including taxol-induced sensory neuropathy, cisplatin-induced sensory neuropathy, and pyridoxine-induced sensory neuropathy.

16 Claims, 9 Drawing Sheets

FOREIGN PATENT DOCUMENTS

| | | |
|---|---|---|
| WO | WO9311230 | 6/1993 |
| WO | WO9319191 | 9/1993 |
| WO | WO9325234 | 12/1993 |
| WO | WO9325698 | 12/1993 |
| WO | WO9403622 | 2/1994 |
| WO | WO9404690 | 3/1994 |
| WO | WO9412649 | 6/1994 |
| WO | WO9423697 | 10/1994 |
| WO | WO9428938 | 12/1994 |
| WO | WO9500655 | 1/1995 |
| WO | WO9507994 | 3/1995 |
| WO | WO9511984 | 5/1995 |
| WO | WO9513796 | 5/1995 |
| WO | WO9530763 | 11/1995 |
| WO | WO9617072 | 6/1996 |
| WO | WO9742338 | 11/1997 |
| WO | WO 99/07410 | 2/1999 |
| WO | WO9958572 | 11/1999 |
| WO | WO0053211 | 9/2000 |
| WO | WO0198361 | 12/2001 |
| WO | WO2004058184 | 7/2004 |
| WO | WO 2004058190 A2 * | 7/2004 |

OTHER PUBLICATIONS

Vajdos, Adams, Breece, Presta, DeVos, Sidhu. Comprehensive functional maps of the antigen-binding site of an anti-ErbB2 antibody obtained with shotgun scanning mutagenesis. Journal of Molecular Biology, 2002. vol. 320, pp. 415-428.*

Holm, Jafari, and Sundstrom. Functional mapping and single chain construction of the anti-cytokeratin 8 monoclonal antibody TS1. Molecular Immunology, 2007. vol. 44, pp. 1075-1084.*

Chen, Wiesmann, Fuh, Li, Christinger, Mc Kay, De Vos, and Lowman. Selection and analysis of an optimized anti-VEGF antibody: crystal structure of an affinity matured Fab in complex with antigen. Journal of Molecular Biology, 1999. vol. 293, pp. 865-881.*

Wu, Nie, Huse, and Watkins. Humanization of a murine monoclonal antibody by simultaneous optimization of framework and CDR residues. Journal of Molecular Biology, 1999. vol. 294, pp. 151-162.*

Nielson, et al., "Affinity Maturation by Chain Shuffling and Site Directed Mutagenesis," Antibody Engineering (Springer Lab Manuals), May 1, 2001, ISBN: 3-540-41354-5, pp. 515-539.*

Takkinen, et al., "Affinity and Specificity Maturation by CDR Walking," Antibody Engineering (Springer Lab Manuals), May 1, 2001, ISBN: 3-540-41354-5, pp. 540-545.*

Urfer, et al., J.Biol. Chem., vol. 273(10), pp. 5829-5840 (1998).
Barbacid, J. Neurobiol., vol. 25, pp. 1386-1403 (1994).
Barbacid, Ann. New York Aced. Sci., vol. 766, pp. 442-458 (1995).
Rydén, et al., J. Biol. Chem., vol. 271(10), pp. 5623-5627 (1996).
Belliveau, et al., J. Cell. Biol., vol. 136, pp. 375-388 (1997).
Fariñas, et al., Neuron, vol. 21, pp. 325-334 (1998).
Chaudhry, et al., Muscle and Nerve, vol. 23, pp. 189-192 (2000).
Haase, et al., J. Neurol. Sci., vol. 160, pp. S97-S105 (1998).
Helgren, et al., J. Neurosci., vol. 17(1), pp. 372-382 (1997).
Armour, et al., Eur. J. Immunol., vol. 29, pp. 2613-2624 (1999).
McCafferty, et al., Nature, vol. 348, pp. 552-554 (1990).
Vaughan, et al., Nature Biotech., vol. 14, pp. 309-314 (1996).
Sheets, et al., PNAS (USA), vol. 95, pp. 6157-6162 (1998).
Hoogenboom, et al., J. Mol. Biol., vol. 227, pp. 381-388 (1991).
Marks, et al., J. Mol. Biol. vol. 222, pp. 581-597 (1991).
Boerner, et al., J. Immunol., vol. 147(1), p. 86-95 (1991).
Al-Lazikani, et al., J. Mol. Biol., vol. 273, pp. 927-948 (1997).
Shelton, et al., J. Neurosci., vol. 15(1), pp. 477-497 (1995).
Ravetch, et al., Ann. Rev. Immunol., vol. 9, pp. 457-492 (1991).
Capel, et al., Immunomethods, vol. 4, pp. 25-34 (1994).
de Haas, et al., J. Lab. Clin. Med., vol. 126, pp. 330-341 (1995).
Guyer, et al., J. Immunol., vol. 117, pp. 587-593 (1976).
Gazzano-Santoro, et al., J. Immunol. Methods, vol. 202, pp. 163-171 (1997).
Clynes, et al., PNAS (USA), vol. 95, pp. 652-656 (1998).
Sadick, et al., Exp. Cell. Res., vol. 234, pp. 354-361 (1997).
Bird, et al., Science, vol. 242, pp. 423-426 (1988).
Holliger, et al., PNAS (USA), vol. 90, pp. 6444-6448 (1993).
Poljak, et al., Structure, vol. 2, pp. 1121-1123 (1994).
Suresh, et al., Methods in Enzymology, vol. 121, pp. 210-228 (1986).
Millstein, et al., Nature, vol. 305, pp. 537-539 (1983).
Jefferis, et al., Chem. Immunol., vol. 65, pp. 111-128 (1997).
Wright, et al., TibTECH, vol. 15, pp. 26-32 (1997).
Boyd, et al., Mol. Immunol., vol. 32(17), pp. 1311-1318 (1995).
Wittwer, et al., Biochemistry, vol. 29, pp. 4175-4180 (1990).
Wyss, et al., Current Opin. Biotech., vol. 7, pp. 409-416 (1996).
Umaña, et al., Nature Biotech., vol. 17, pp. 176-180 (1999).
Hsu, et al., J. Biol. Chem., vol. 272; pp. 9062-9070 (1997).
Barbas, et al., PNAS (USA), vol. 91, pp. 3809-3813 (1994).
Schier, et al., Gene, vol. 169, pp. 147-155 (1996).
Yelton, et al., J. Immunol., vol. 155(4), pp. 1994-2004 (1995).
Jackson, et al., J. Immunol., vol. 154(7), pp. 3310-3319 (1995).
Hawkins, et al., J. Mol. Biol., vol. 226(3), pp. 889-896 (1992).
Balint, et al., Gene, vol. 137(1), pp. 109-118 (1993).
Wilbur, et al., PNAS(USA), vol. 80, pp. 726-730 (1983).
Mahato, et al., Pharm. Res., vol. 14(7), pp. 853-859 (1997).
Sevarino, et al., J. Biol. Chem., vol. 263(2), pp. 620-623 (1988).
Miura, et al., J. Biol. Chem., vol. 269(1), pp. 542-547 (1994).
Zenke, et al., PNAS(USA), vol. 87(10), pp. 3655-3659 (1990).
Dickinson, et al., J. Biol. Chem., vol. 266(1), pp. 334-338 (1991).
Curiel, et al., Hum. Gene Ther., vol. 3, pp. 147-154 (1992).
Wu, et al., J. Biol. Chem., vol. 264(29), pp. 16985-16987 (1989).
Philip, et al., Mol. Cell Biol., vol. 14(4), pp. 2411-2418 (1994).
Eppstein, et al., PNAS(USA), vol. 82, pp. 3688-3692 (1985).
Hwang, et al., PNAS(USA), vol. 77, pp. 4030-4034 (1980).
Chattopadhyay, et al., Ann. Neurol., vol. 51(1), pp. 19-27 (2002).
Pisano, et al., Clin. Cancer Res., vol. 9, pp. 5756-5767 (2003).
Tredici, et al., Exp. Neurol., vol. 159, pp. 551/558 (1999).
Sadick, M.D., Analysis of Neurotropin/Receptor Interactions with a gD-Flag-Modified Quantitative Kinase Receptor Activation (gD. KIRA) ELISA. Experimental Cell Research 1997, 234:354-361.
Armour, K.L. "Recombinant Human IgG Molecules Lacking Fcgamma Receptor I Binding and Monocyte Triggering Activities" European Journal of Immunology, 1999. 29:2613-2624.
Nielson, et al., "Affinity Maturation by Chain Shuffling and Site Directed Mutagenesis," *Antibody Engineering* (Springer Lab Manuals), May 1, 2001, ISBN: 3-540-41354-5, 515-539.
Takkinen, et al., "Affinity and Specificity Maturation by CDR Walking," *Antibody Engineering* (Springer Lab Manuals), May 1, 2001, ISBN: 3-540-41354-5, 540-545.

* cited by examiner

FIGURE 1

BOX= CDRS: bold =Kabat, *Italics=Chothia*

A. Antibody A5 Heavy chain variable domain

```
        1  2  3  4  5  6  7  8  9 10 11 12 13 14 15 16 17 18 19 20 21 22 23 24 25 26 27 28 29 30 31 32 33 34 35 36 37 38 39 40
                                                                                        H1
A5-H    Q  V  Q  L  V  Q  S  G  A  E  V  K  K  P  G  A  S  V  K  V  S  C  K  A  S  G  Y  T  F  T  S  Y  R  I  H  W  V  R  Q  A 41 42 43 44 45 46 47 48 49 50 51 52 53 54 55 56 57 58 59 60 61 62 63 64 65 66 67 68 69 70 71 72 73 74 75 76 77 78 79 80
                                        H2
A5-H    P  G  Q  G  L  E  W  M  G  E  I  Y  P  S  N  A  R  T  N  Y  N  E  K  F  K  S  R  V  T  M  T  R  D  T  S  T  S  T  V  Y
                                                                                H3
       8182 83 84 85 86 87 88 89 90 91 92 93 94 95 96 97 98 99 100   105             110             115                 120
A5-H    M  E  L  S  S  L  R  S  E  D  T  A  V  Y  Y  C  A  R  K  Y  Y  Y  G  N  T  R  R  S  W  Y  F  D  V  W  G  Q  G  T  T  V 121 122 123
A5-H    T  V  S
```

B. Antibody A5 Light chain variable domain

BOX = CDRS: bold =Kabat, *Italics* =Chothia

A. Heavy chain variable domain (SEQ ID NO:14)

```
       1  2  3  4  5  6  7  8  9 10 11 12 13 14 15 16 17 18 19 20 21 22 23 24 25 26 27 28 29 30 31 32 33 34 35 36 37 38 39 40
2256H  Q  V  Q  L  Q  Q  P  G  A  E  L  V  K  P  G  A  S  V  K  L  S  C  K  A  S  G  Y  T  F  T  S  Y  W  M  H  W  V  K  Q  R
                                                                                         ─────────H1──────────

41 42 43 44 45 46 47 48 49 50 51 52 53 54 55 56 57 58 59 60 61 62 63 64 65 66 67 68 69 70 71 72 73 74 75 76 77 78 79 80
2256H  P  G  Q  G  L  E  W  I  G  E  I  Y  P  S  N  G  R  T  N  Y  N  E  K  F  K  S  K  A  T  L  T  V  D  K  S  S  T  A  Y
                                    ────────────H2────────────────

8182 83 84 85 86 87 88 89 90 91 92 93 94 95 96 97 98 99 100                              105                    110                              115                              120
2256H  M  Q  L  S  S  L  T  S  E  D  S  A  V  Y  Y  C  A  R  K  Y  Y  Y  G  N  S  Y  R  S  W  Y  F  D  V  W  G  A  G  T  T  L
                                                        ──────────────────H3──────────────────

121 122 123
2256H  T  V  S
```

B. Light chain variable domain (SEQ ID NO:15)

```
       1  2  3  4  5  6  7  8  9 10 11 12 13 14 15 16 17 18 19 20 21 22 23 24 25 26 27 28 29 30 31 32 33 34 35 36 37 38 39 40
2256L  D  I  V  L  T  Q  S  P  A  S  L  A  V  S  L  G  Q  R  A  T  I  S  C  R  A  S  E  S  V  D  N  Y  G  I  S  F  M  N  W  F
                                                            ──────────────────L1──────────────────

41 42 43 44 45 46 47 48 49 50 51 52 53 54 55 56 57 58 59 60 61 62 63 64 65 66 67 68 69 70 71 72 73 74 75 76 77 78 79 80
2256L  Q  Q  K  P  G  Q  P  P  K  L  L  I  Y  A  A  S  N  Q  G  S  G  V  P  A  R  F  S  G  S  G  S  G  T  D  F  S  L  N  I  H
                                       ──────L2─────

8182 83 84 85 86 87 88 89 90 91 92 93 94 95 96 97 98 99 100                              105                    110              114
2256L  P  M  E  D  D  T  A  M  Y  F  C  Q  Q  S  K  E  V  P  R  T  F  G  G  G  T  K  L  E  M  K  R  T
                              ────────────L3────────────
```

SEQUENCE LISTING

<160> NUMBER OF SEQ ID NOS: 31

<210> SEQ ID NO 1
<211> LENGTH: 123
<212> TYPE: PRT
<213> ORGANISM: Artificial
<220> FEATURE:
<223> OTHER INFORMATION: Synthetic Construct

<400> SEQUENCE: 1

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Arg Ile His Trp Val Arg Gln Ala Pro Gly Gln Gly Leu Glu Trp Met
        35                  40                  45

Gly Glu Ile Tyr Pro Ser Asn Ala Arg Thr Asn Tyr Asn Glu Lys Phe
    50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Tyr Tyr Tyr Gly Asn Thr Arg Arg Ser Trp Tyr Phe Asp
            100                 105                 110

Val Trp Gly Gln Gly Thr Thr Val Thr Val Ser
        115                 120

<210> SEQ ID NO 2
<211> LENGTH: 113
<212> TYPE: PRT
<213> ORGANISM: Artificial
<220> FEATURE:
<223> OTHER INFORMATION: Synthetic construct

<400> SEQUENCE: 2

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Asp Asn Tyr
            20                  25                  30

Gly Ile Ser Phe Leu Ala Trp Tyr Gln Gln Lys Pro Gly Lys Ala Pro
        35                  40                  45

Lys Leu Leu Ile Tyr Ala Ala Ser Asn Arg Gly Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln Gln Ser Lys
                85                  90                  95

Thr Val Pro Arg Thr Phe Gly Gln Gly Thr Lys Leu Glu Ile Lys Arg
            100                 105                 110

Thr

<210> SEQ ID NO 3
<211> LENGTH: 15
<212> TYPE: PRT
<213> ORGANISM: Artificial
<220> FEATURE:
<223> OTHER INFORMATION: Synthetic construct

<400> SEQUENCE: 3

```
Gly Gly Gly Gly Ser Gly Gly Gly Ser Gly Gly Gly Ser
1               5                   10                  15

<210> SEQ ID NO 4
<211> LENGTH: 10
<212> TYPE: PRT
<213> ORGANISM: Artificial
<220> FEATURE:
<223> OTHER INFORMATION: Synthetic construct

<400> SEQUENCE: 4

Gly Tyr Thr Phe Thr Ser Tyr Arg Ile His
1               5                   10

<210> SEQ ID NO 5
<211> LENGTH: 17
<212> TYPE: PRT
<213> ORGANISM: Artificial
<220> FEATURE:
<223> OTHER INFORMATION: Synthetic construct

<400> SEQUENCE: 5

Glu Ile Tyr Pro Ser Asn Ala Arg Thr Asn Tyr Asn Glu Lys Phe Lys
1               5                   10                  15

Ser

<210> SEQ ID NO 6
<211> LENGTH: 15
<212> TYPE: PRT
<213> ORGANISM: Artificial
<220> FEATURE:
<223> OTHER INFORMATION: Synthetic construct

<400> SEQUENCE: 6

Lys Tyr Tyr Tyr Gly Asn Thr Arg Arg Ser Trp Tyr Phe Asp Val
1               5                   10                  15

<210> SEQ ID NO 7
<211> LENGTH: 15
<212> TYPE: PRT
<213> ORGANISM: Artificial
<220> FEATURE:
<223> OTHER INFORMATION: Synthetic construct

<400> SEQUENCE: 7

Arg Ala Ser Glu Ser Ile Asp Asn Tyr Gly Ile Ser Phe Leu Ala
1               5                   10                  15

<210> SEQ ID NO 8
<211> LENGTH: 7
<212> TYPE: PRT
<213> ORGANISM: Artificial
<220> FEATURE:
<223> OTHER INFORMATION: Synthetic construct

<400> SEQUENCE: 8

Ala Ala Ser Asn Arg Gly Ser
1               5

<210> SEQ ID NO 9
<211> LENGTH: 9
<212> TYPE: PRT
<213> ORGANISM: Artificial
<220> FEATURE:
<223> OTHER INFORMATION: Synthetic construct

<400> SEQUENCE: 9
```

Gln Gln Ser Lys Thr Val Pro Arg Thr
1               5

<210> SEQ ID NO 10
<211> LENGTH: 338
<212> TYPE: DNA
<213> ORGANISM: Artificial
<220> FEATURE:
<223> OTHER INFORMATION: Synthetic construct

<400> SEQUENCE: 10
gatatccaga tgacacagtc cccatcctcc ctgtctgcct ctgtgggtga ccgcgtcacc     60
atcacctgcc gcgcaagtga gagcatcgac aactatggca tttccttcct ggcctggtat    120
cagcagaagc cgggcaaagc accaaaactc ctgatctatg ctgcatccaa tcggggttca    180
ggtgtcccat cacgcttcag tggcagtggc tctggtacag atttcaccct caccattagc    240
agcctgcaac agaagatat tgccacttat tactgccaac agagtaagac tgtgccacgc     300
actttcggtc aaggcaccaa gctggagatc aaacgcac                            338

<210> SEQ ID NO 11
<211> LENGTH: 654
<212> TYPE: DNA
<213> ORGANISM: Artificial
<220> FEATURE:
<223> OTHER INFORMATION: Synthetic construct

<400> SEQUENCE: 11
gatatccaga tgacacagtc cccatcctcc ctgtctgcct ctgtgggtga ccgcgtcacc     60
atcacctgcc gcgcaagtga gagcatcgac aactatggca tttccttcct ggcctggtat    120
cagcagaagc cgggcaaagc accaaaactc ctgatctatg ctgcatccaa tcggggttca    180
ggtgtcccat cacgcttcag tggcagtggc tctggtacag atttcaccct caccattagc    240
agcctgcaac agaagatat tgccacttat tactgccaac agagtaagac tgtgccacgc     300
actttcggtc aaggcaccaa gctggagatc aaacgcactg tggctgcacc atctgtcttc    360
atcttccctc catctgatga gcagttgaaa tccggaactg cctctgttgt gtgcctgctg    420
aataacttct atcccgcgcga ggccaaagta cagtggaagg tggataacgc cctccaatcc    480
ggtaactccc aggagagtgt cacagagcag gacagcaagg acagcaccta cagcctcagc    540
agcaccctga ccctgagcaa agcagactac gagaaacaca agtctacgc ctgcgaagcc     600 acccatcagg gcctgagttc tccagtcaca aagagcttca ccgcggtga gtgc            654

<210> SEQ ID NO 12
<211> LENGTH: 369
<212> TYPE: DNA
<213> ORGANISM: Artificial
<220> FEATURE:
<223> OTHER INFORMATION: Synthetic Construct

<400> SEQUENCE: 12
caggtgcagc tggtgcagtc tggtgctgag gtgaagaagc ctggcgcttc cgtgaaggtt     60
tcctgcaaag catctggtta caccttacc agctatcgga tccactgggt gcgccaagcc    120
cctggtcaag gcctggagtg gatgggcgaa atctacccaa gcaacgcgcg cactaactac    180
aacgagaagt tcaaatcccg ggtgaccatg actcgcgata cctccaccag cactgtctac    240
atggaactga gctctctgcg ctctgaggac actgctgtgt attactgtgc ccgcaagtac    300
tattacggca atacgcgtcg ctcctggtac ttcgatgtgt ggggccaggg taccactgtt    360

```
accgtgtcc                                                                        369

<210> SEQ ID NO 13
<211> LENGTH: 1348
<212> TYPE: DNA
<213> ORGANISM: Artificial
<220> FEATURE:
<223> OTHER INFORMATION: Synthetic Construct

<400> SEQUENCE: 13
ggtgcagctg gtgcagtctg gtgctgaggt gaagaagcct ggcgcttccg tgaaggtttc      60
ctgcaaagca tctggttaca cctttaccag ctatcggatc cactgggtgc gccaagcccc     120
tggtcaaggc ctggagtgga tgggcgaaat ctacccaagc aacgcgcgca ctaactacaa     180
cgagaagttc aaatcccggg tgaccatgac tcgcgatacc tccaccagca ctgtctacat     240
ggaactgagc tctctgcgct ctgaggacac tgctgtgtat tactgtgccc gcaagtacta     300
ttacggcaat acgcgtcgct cctggtactt cgatgtgtgg ggccagggta ccactgttac     360
cgtgtcctct gcctccacca agggcccatc tgtcttccca ctggccccat gctccgcag     420 cacctccgag agcacagccg ccctgggctg cctggtcaag gactacttcc cagaaccctgt     480 gaccgtgtcc tggaactctg gcgctctgac cagcggcgtg cacaccttcc cagctgtcct     540
gcagtcctca ggtctctact ccctcagcag cgtggtgacc gtgccatcca gcaacttcgg     600
cacccagacc tacacctgca acgtagatca caagccaagc aacaccaagg tcgacaagac     660
cgtggagaga agtgttgtg tggagtgtcc accttgtcca gcccctccag tggccggacc     720
atccgtgttc ctgttccctc caaagccaaa ggacaccctg atgatctcca gaaccccaga     780
ggtgacctgt gtggtggtgg acgtgtccca cgaggaccca gaggtgcagt tcaactggta     840
tgtggacgga gtggaggtgc acaacgccaa gaccaagcca gagaggagc agttcaactc     900 caccttcaga gtggtgagcg tgctgaccgt ggtgcaccag gactggctga acggaaagga     960
gtataagtgt aaggtgtcca acaagggact gccatccagc atcgagaaga ccatctccaa    1020
gaccaaggga cagccaagag agccacaggt gtatacctg ccaccatcca gagaggagat    1080
gaccaagaac caggtgtccc tgacctgtct ggtgaaggga ttctatccat ccgacatcgc    1140
cgtggagtgg gagtccaacg gacagccaga gaacaactat aagaccaccc ctccaatgct    1200
ggactccgac ggatccttct tcctgtattc caagctgacc gtggacaagt ccagatggca    1260
gcagggaaac gtgttctctt gttccgtgat gcacgaggcc ctgcacaacc actatacccca    1320 gaagagcctg tccctgtctc caggaaag                                         1348

<210> SEQ ID NO 14
<211> LENGTH: 10
<212> TYPE: PRT
<213> ORGANISM: Homo sapiens

<400> SEQUENCE: 14

Trp Gln Gly Thr Leu Val Thr Val Ser Ser
1               5                   10

<210> SEQ ID NO 15
<211> LENGTH: 11
<212> TYPE: PRT
<213> ORGANISM: Homo sapiens

<400> SEQUENCE: 15

Thr Phe Gly Gln Gly Thr Lys Leu Glu Ile Lys
1               5                   10
```

```
<210> SEQ ID NO 16
<211> LENGTH: 10
<212> TYPE: PRT
<213> ORGANISM: Artificial
<220> FEATURE:
<223> OTHER INFORMATION: Synthetic Construct
<220> FEATURE:
<221> NAME/KEY: VARIANT
<222> LOCATION: (8)..(8)
<223> OTHER INFORMATION: X = R or W
<220> FEATURE:
<221> NAME/KEY: VARIANT
<222> LOCATION: (9)..(9)
<223> OTHER INFORMATION: X = I, L, R or M

<400> SEQUENCE: 16

Gly Tyr Thr Phe Thr Ser Tyr Xaa Xaa His
1               5                   10

<210> SEQ ID NO 17
<211> LENGTH: 17
<212> TYPE: PRT
<213> ORGANISM: Artificial
<220> FEATURE:
<223> OTHER INFORMATION: Synthetic construct
<220> FEATURE:
<221> NAME/KEY: VARIANT
<222> LOCATION: (7)..(7)
<223> OTHER INFORMATION: X = A, T, S, or G
<220> FEATURE:
<221> NAME/KEY: VARIANT
<222> LOCATION: (16)..(16)
<223> OTHER INFORMATION: X = K or E

<400> SEQUENCE: 17

Glu Ile Tyr Pro Ser Asn Xaa Arg Thr Asn Tyr Asn Glu Lys Phe Xaa
1               5                   10                  15

Ser

<210> SEQ ID NO 18
<211> LENGTH: 15
<212> TYPE: PRT
<213> ORGANISM: Artificial
<220> FEATURE:
<223> OTHER INFORMATION: Synthetic construct
<220> FEATURE:
<221> NAME/KEY: VARIANT
<222> LOCATION: (7)..(7)
<223> OTHER INFORMATION: X = T or S
<220> FEATURE:
<221> NAME/KEY: VARIANT
<222> LOCATION: (8)..(8)
<223> OTHER INFORMATION: X = R, Q, K, S OR Y

<400> SEQUENCE: 18

Lys Tyr Tyr Tyr Gly Asn Xaa Xaa Arg Ser Trp Tyr Phe Asp Val
1               5                   10                  15

<210> SEQ ID NO 19
<211> LENGTH: 15
<212> TYPE: PRT
<213> ORGANISM: Artificial
<220> FEATURE:
<223> OTHER INFORMATION: Synthetic construct
<220> FEATURE:
<221> NAME/KEY: VARIANT
<222> LOCATION: (6)..(6)
<223> OTHER INFORMATION: X = I or V
<220> FEATURE:
<221> NAME/KEY: VARIANT
<222> LOCATION: (8)..(8)
<223> OTHER INFORMATION: X = N or S
```

```
<220> FEATURE:
<221> NAME/KEY: VARIANT
<222> LOCATION: (14)..(14)
<223> OTHER INFORMATION: X = L or M
<220> FEATURE:
<221> NAME/KEY: VARIANT
<222> LOCATION: (15)..(15)
<223> OTHER INFORMATION: X = A, T or N

<400> SEQUENCE: 19

Arg Ala Ser Glu Ser Xaa Asp Xaa Tyr Gly Ile Ser Phe Xaa Xaa
 1               5                  10                  15

<210> SEQ ID NO 20
<211> LENGTH: 7
<212> TYPE: PRT
<213> ORGANISM: Artificial
<220> FEATURE:
<223> OTHER INFORMATION: Synthetic construct
<220> FEATURE:
<221> NAME/KEY: VARIANT
<222> LOCATION: (5)..(5)
<223> OTHER INFORMATION: X = R, L, or Q

<400> SEQUENCE: 20

Ala Ala Ser Asn Xaa Gly Ser
 1               5

<210> SEQ ID NO 21
<211> LENGTH: 9
<212> TYPE: PRT
<213> ORGANISM: Artificial
<220> FEATURE:
<223> OTHER INFORMATION: Synthetic construct
<220> FEATURE:
<221> NAME/KEY: VARIANT
<222> LOCATION: (5)..(5)
<223> OTHER INFORMATION: x = T, A, S or E

<400> SEQUENCE: 21

Gln Gln Ser Lys Xaa Val Pro Arg Thr
 1               5

<210> SEQ ID NO 22
<211> LENGTH: 10
<212> TYPE: PRT
<213> ORGANISM: Mus musculus

<400> SEQUENCE: 22

Gly Tyr Thr Phe Thr Ser Tyr Trp Met His
 1               5                  10

<210> SEQ ID NO 23
<211> LENGTH: 17
<212> TYPE: PRT
<213> ORGANISM: Mus musculus

<400> SEQUENCE: 23

Glu Ile Tyr Pro Ser Asn Gly Arg Thr Asn Tyr Asn Glu Lys Phe Lys
 1               5                  10                  15
Ser

<210> SEQ ID NO 24
<211> LENGTH: 15
<212> TYPE: PRT
<213> ORGANISM: Mus musculus

<400> SEQUENCE: 24
```

```
Lys Tyr Tyr Tyr Gly Asn Ser Tyr Arg Ser Trp Tyr Phe Asp Val
1               5                   10                  15

<210> SEQ ID NO 25
<211> LENGTH: 15
<212> TYPE: PRT
<213> ORGANISM: Mus musculus

<400> SEQUENCE: 25

Arg Ala Ser Glu Ser Val Asp Asn Tyr Gly Ile Ser Phe Met Asn
1               5                   10                  15

<210> SEQ ID NO 26
<211> LENGTH: 7
<212> TYPE: PRT
<213> ORGANISM: Mus musculus

<400> SEQUENCE: 26

Ala Ala Ser Asn Gln Gly Ser
1               5

<210> SEQ ID NO 27
<211> LENGTH: 9
<212> TYPE: PRT
<213> ORGANISM: Mus musculus

<400> SEQUENCE: 27

Gln Gln Ser Lys Glu Val Pro Arg Thr
1               5

<210> SEQ ID NO 28
<211> LENGTH: 450
<212> TYPE: PRT
<213> ORGANISM: Artificial
<220> FEATURE:
<223> OTHER INFORMATION: Synthetic sequence

<400> SEQUENCE: 28

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Arg Ile His Trp Val Arg Gln Ala Pro Gly Gln Gly Leu Glu Trp Met
            35                  40                  45

Gly Glu Ile Tyr Pro Ser Asn Ala Arg Thr Asn Tyr Asn Glu Lys Phe
        50                  55                  60

Lys Ser Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95

Ala Arg Lys Tyr Tyr Tyr Gly Asn Thr Arg Arg Ser Trp Tyr Phe Asp
                100                 105                 110

Val Trp Gly Gln Gly Thr Thr Val Thr Val Ser Ser Ala Ser Thr Lys
            115                 120                 125

Gly Pro Ser Val Phe Pro Leu Ala Pro Cys Ser Arg Ser Thr Ser Glu
        130                 135                 140

Ser Thr Ala Ala Leu Gly Cys Leu Val Lys Asp Tyr Phe Pro Glu Pro
145                 150                 155                 160

Val Thr Val Ser Trp Asn Ser Gly Ala Leu Thr Ser Gly Val His Thr
                165                 170                 175

Phe Pro Ala Val Leu Gln Ser Ser Gly Leu Tyr Ser Leu Ser Ser Val
```

```
                        180                 185                 190
Val Thr Val Pro Ser Ser Asn Phe Gly Thr Gln Thr Tyr Thr Cys Asn
            195                 200                 205

Val Asp His Lys Pro Ser Asn Thr Lys Val Asp Lys Thr Val Glu Arg
        210                 215                 220

Lys Cys Cys Val Glu Cys Pro Pro Cys Pro Ala Pro Val Ala Gly
225                 230                 235                 240

Pro Ser Val Phe Leu Phe Pro Pro Lys Pro Lys Asp Thr Leu Met Ile
                    245                 250                 255

Ser Arg Thr Pro Glu Val Thr Cys Val Val Val Asp Val Ser His Glu
                260                 265                 270

Asp Pro Glu Val Gln Phe Asn Trp Tyr Val Asp Gly Val Glu Val His
            275                 280                 285

Asn Ala Lys Thr Lys Pro Arg Glu Glu Gln Phe Asn Ser Thr Phe Arg
        290                 295                 300

Val Val Ser Val Leu Thr Val His Gln Asp Trp Leu Asn Gly Lys
305                 310                 315                 320

Glu Tyr Lys Cys Lys Val Ser Asn Lys Gly Leu Pro Ser Ser Ile Glu
                    325                 330                 335

Lys Thr Ile Ser Lys Thr Lys Gly Gln Pro Arg Glu Pro Gln Val Tyr
                340                 345                 350

Thr Leu Pro Pro Ser Arg Glu Met Thr Lys Asn Gln Val Ser Leu
            355                 360                 365

Thr Cys Leu Val Lys Gly Phe Tyr Pro Ser Asp Ile Ala Val Glu Trp
        370                 375                 380

Glu Ser Asn Gly Gln Pro Glu Asn Asn Tyr Lys Thr Thr Pro Pro Met
385                 390                 395                 400

Leu Asp Ser Asp Gly Ser Phe Phe Leu Tyr Ser Lys Leu Thr Val Asp
                    405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 29
<211> LENGTH: 165
<212> TYPE: PRT
<213> ORGANISM: Artificial
<220> FEATURE:
<223> OTHER INFORMATION: Synthetic construct

<400> SEQUENCE: 29

Asp Ile Gln Met Thr Gln Ser Pro Ser Ser Leu Ser Ala Ser Val Gly
1               5                   10                  15

Asp Arg Val Thr Ile Thr Cys Arg Ala Ser Glu Ser Ile Asp Asn Tyr
            20                  25                  30

Gly Ile Ser Phe Leu Ala Trp Tyr Gln Gln Lys Pro Gly Lys Ala Pro
        35                  40                  45

Lys Leu Leu Ile Tyr Ala Ala Ser Asn Arg Gly Ser Gly Val Pro Ser
    50                  55                  60

Arg Phe Ser Gly Ser Gly Ser Gly Thr Asp Phe Thr Phe Thr Ile Ser
65                  70                  75                  80

Ser Leu Gln Pro Glu Asp Ile Ala Thr Tyr Tyr Cys Gln Gln Ser Lys
                85                  90                  95
```

```
Thr Val Pro Arg Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu
                165

<210> SEQ ID NO 30
<211> LENGTH: 123
<212> TYPE: PRT
<213> ORGANISM: Mus musculus

<400> SEQUENCE: 30

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Trp Met His Trp Val Lys Gln Arg Pro Gly Gln Gly Leu Glu Trp Ile
        35                  40                  45

Gly Glu Ile Tyr Pro Ser Asn Gly Arg Thr Asn Tyr Asn Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Lys Tyr Tyr Tyr Gly Asn Ser Tyr Arg Ser Trp Tyr Phe Asp
            100                 105                 110

Val Trp Gly Ala Gly Thr Thr Leu Thr Val Ser
        115                 120

<210> SEQ ID NO 31
<211> LENGTH: 113
<212> TYPE: PRT
<213> ORGANISM: Mus musculus

<400> SEQUENCE: 31

Asp Ile Val Leu Thr Gln Ser Pro Ala Ser Leu Ala Val Ser Leu Gly
1               5                   10                  15

Gln Arg Ala Thr Ile Ser Cys Arg Ala Ser Glu Ser Val Asp Asn Tyr
            20                  25                  30

Gly Ile Ser Phe Met Asn Trp Phe Gln Gln Lys Pro Gly Gln Pro Pro
        35                  40                  45

Lys Leu Leu Ile Tyr Ala Ala Ser Asn Gln Gly Ser Gly Val Pro Ala
    50                  55                  60

Arg Phe Ser Gly Ser Gly Ser Gly Thr Asp Phe Ser Leu Asn Ile His
65                  70                  75                  80

Pro Met Glu Glu Asp Asp Thr Ala Met Tyr Phe Cys Gln Gln Ser Lys
                85                  90                  95

Glu Val Pro Arg Thr Phe Gly Gly Gly Thr Lys Leu Glu Met Lys Arg
            100                 105                 110

Thr
```

US 7,968,690 B2

AGONIST ANTI-TRKC ANTIBODIES AND METHODS USING SAME

CROSS-REFERENCE TO RELATED APPLICATIONS

This application claims the priority benefit of provisional application U.S. Ser. No. 60/532,592, filed Dec. 23, 2003, which is incorporated by reference in its entirety.

FIELD OF THE INVENTION

The invention concerns agonist anti-trkC antibodies and polypeptides. The invention her concerns use of such antibodies and polypeptides in the treatment and/or prevention of diseases, such as sensory neuropathy.

STATEMENT REGARDING FEDERALLY SPONSORED RESEARCH OR DEVELOPMENT

Not applicable.

BACKGROUND OF THE INVENTION

Neurotrophins are a family of small, homodimeric proteins, which play a crucial role in the development and maintenance of the nervous system. Members of the neurotrophin family include nerve growth factor (NGF), brain-derived neurotrophic factor (BDNF), neurotrophin-3 (NT-3), neurotrophin-4/5 (NT-4/5), neurotrophin-6 (NT-6), and neurotrophin-7 (NT-7). Neurotrophins, similar to other polypeptide growth factors, affect their target cells through interactions with cell surface receptors. According to current knowledge, two kinds of transmembrane glycoproteins serve as receptors for neurotrophins. Neurotrophin-responsive neurons possess a common low molecular weight (65-80 kDa), low affinity receptor (LNGFR), also termed as p75NTR or p75, which binds NGF, BDNF, NT-3 and NT-4/5 with a $K_D$ of $2\times10^{-9}$ M; and large molecular weight (130-150 kDa), high-affinity ($K_D$ in the $10^{-11}$ M range) receptors, which are members of the trk family of receptor tyrosine kinases. The identified members of the trk receptor family are trkA, trkB, and trkC.

TrkC is widely expressed in the central nervous system, and on a subset of neurons in the peripheral nervous system. TrkC is also expressed on some parasympathetic, enteric neurons, and some non-neural tissues. It is expressed on sympathetic neurons and on a subset of primary sensory neurons of the DRG, the large fiber sensory neurons of the DRG. Large fiber sensory neurons have large myelinated axons extending to the periphery, where they convey information regarding proprioception, and fine touch and vibration sense.

The extracellular domains of full-length native trkA, trkB and trkC receptors have five structural domains that have been defined with reference to homologous or otherwise similar structures identified in various other proteins. The domains have been designated starting at the N-terminus of the amino acid sequence of the mature trk receptors as 1) a first cysteine-rich domain; 2) a leucine-rich domain; 3) a second cysteine-rich domain; 4) a first immunoglobulin-like domain; and 5) a second immunoglobulin-like domain. See, e.g., PCT Publication No. WO 0198361; Urfer et al. *J. Biol. Chem.* 273: 5829-5840 (1998).

Neurotrophins are of interest as potential therapeutic agents for a variety of neurodegenerative and neurological diseases. Neurotrophins, such as NGF and NT-3, were tested in animal models for treating sensory neuropathy associated with pyridoxine or cis-platinum treatment. U.S. Pat. No. 5,604,202; PCT Publication No. WO 0198361. Using neurotrophins in treatment of neurodegenerative and neurological diseases have several shortcomings. One significant shortcoming is the lack of specificity. Most neurotrophins cross-react with more than one receptor. For example NT-3, the preferred ligand of the trkC receptor tyrosine kinase, also binds to and activates trkA and trkB (Barbacid, *J. Neurobiol.* 25:1386-1403, 1994; Barbarcid, *Ann. New York Aced. Sci.* 766:442-458, 1995; Ryden and Ibanez, *J. Biol. Chem.* 271: 5623-5627, 1996, Belliveau et al., *J. Cell. Biol.* 136:375-388, 1997; Farinas et al., *Neuron* 21:325-334, 1998). As a result, it is difficult to devise therapies that target a specific population of neurons. Another limitation of neurotrophin therapy is that neurotrophins, including NT-3, are known to elicit hyperalgesia (Chaudhry et al., *Muscle and Nerve* 23:189-192, 2000). In addition, some neurotrophins such as NT-3 have poor pharmacokinetic and bioavailability properties in rodents, which raise serious questions about their human clinical applications (Haase et al., *J. Neurol. Sci.* 160:S97-S105, 1998, dosages used in Helgren et al., *J. Neurosci.* 17(I):372-82, 1997). There is therefore a need for the development of new therapeutic agents for the treatment of neurodegenerative disorders and neurological diseases that are devoid of the known shortcoming of neurotrophins.

Rodent agonist anti-trkC antibodies have been reported. See PCT Publication No. WO 01/98361. However, when rodent antibodies are used therapeutically in humans, a human anti-murine antibody response develops in significant numbers of treated individuals. In addition, effector functions of mouse antibodies have proven to be less efficient in the human context. Thus, there is a serious need for improved agonist anti-trkC antibodies, including humanized agonist anti-trkC agonist antibodies.

All references, publications, and patent applications disclosed herein are hereby incorporated by reference in their entirety.

BRIEF SUMMARY OF THE INVENTION

The invention disclosed herein concerns agonist antibodies to the trkC receptor. Accordingly, in one aspect, the invention is a humanized and affinity matured antibody, A5, that specifically binds human and rodent trkc receptor ("trkC"). The amino acid sequences of the heavy chain and light chain variable regions of A5 are shown in FIGS. 1A (SEQ ID NO: 1) and 1B (SEQ ID NO:2), respectively. The complementarity determining region (CDR) portions of antibody A5 (including Chothia and Kabat CDRs) are diagrammatically depicted in FIGS. 1A and 1B. The amino acid sequences of A5 heavy and light chains, and of the individual extended CDRs are also shown below (See, "antibody sequences", below).

The invention also provides an agonist anti-trkC antibody (in some embodiments, a polypeptide) comprising a heavy chain CDRs comprising: (a) a CDR1 of the formula GYTFTSYXaaXaaH (SEQ ID NO:16), wherein Xaa at position 8 is R or W, and Xaa at position 9 is I, L, R, or M; (b) a CDR2 of the formula EIYPSNXaaRTNYNEKFXaaS (SEQ ID NO: 17), wherein Xaa at position 7 is A, T, S, or G; and Xaa at position 16 is K or E; and (c) a CDR3 of the formula KYYYGNXaaXaaRSWYFDV (SEQ ID NO: 18), wherein Xaa at position 7 is T or S; wherein Xaa at position 8 is R, Q, K, S, or Y; wherein the antibody is not an antibody comprising a heavy chain CDRs comprising a CDR1 region of SEQ ID NO:22, a CDR2 region of SEQ ID NO:23, and a CDR3 region of SEQ ID NO:24. In some embodiments, the CDR1 has the sequence of the formula GYTFTSYXaaXaaH (SEQ ID NO: 16), wherein Xaa at position 8 is R, and Xaa at position 9 is I, L, or R. In some embodiments, the CDR2 has the sequence of the formula EIYPSNXaaRTNYNEKFXaaS (SEQ ID NO: 17), wherein Xaa at position 7 is A, T, or S; and Xaa at position 16 is K or E. In some embodiments, the CDR3 has the sequence of the formula KYYYGNXaaXaaRSWYFDV (SEQ ID NO: 18), wherein Xaa at position 7 is T; wherein Xaa at position 8 is R, Q, K, or S. In some embodiments, the antibody comprises a light chain variable region.

The invention also provides an agonist anti-trkC antibody (in some embodiments, a polypeptide) comprising a light chain CDRs comprising: (a) a CDR1 of the formula RAS-ESXaaDXaaYGISFXaaXaa (SEQ ID NO:19), wherein Xaa at position 6 is I or V; Xaa at position 8 is N or S; Xaa at position 14 is L or M; Xaa at position 15 is A, T, or N; (b) a CDR2 of the formula AASNXaaGS (SEQ ID NO:20), wherein Xaa at position 5 is R, L, or Q; and (c) a CDR3 of the formula QQSKXaaVPRT (SEQ ID NO:21), wherein Xaa at position 5 is T, A, S, or E; wherein the antibody is not an antibody comprising a light chain CDRs comprising a CDR1 region of SEQ ID NO:25, a CDR2 region of SEQ ID NO:26, and a CDR3 region of SEQ ID NO:27. In some embodiments, the CDR1 has the sequence of the formula RASESXaaDX-aaYGISFXaaXaa (SEQ ID NO:19), wherein Xaa at position 6 is I; Xaa at position 8 is N or S; Xaa at position 14 is L; Xaa at position 15 is A or T. In some embodiments, the CDR2 has the sequence of the formula AASNXaaGS (SEQ ID NO:20), wherein Xaa at position 5 is R or L. In some embodiments, the CDR3 has the sequence of QQSKXaaVPRT (SEQ ID NO:21), wherein Xaa at position 5 is T, A, or S. In some embodiments, the antibody comprises a heavy chain variable region.

The invention also provides an agonist anti-trkC antibody (in some embodiments, a polypeptide) comprising: (a) a heavy chain CDRs comprising: (i) a CDR1 of the formula GYTFTSYXaaXaaH (SEQ ID NO: 16), wherein Xaa at position 8 is R or W, and Xaa at position 9 is I, L, R, or M; (ii) a CDR2 of the formula EIYPSNXaaRTNYNEKFXaaS (SEQ ID NO: 17), wherein Xaa at position 7 is A, T, S, or G; and Xaa at position 16 is K or E; and (iii) a CDR3 of the formula KYYYGNXaaXaaRSWYFDV (SEQ ID NO: 18), wherein Xaa at position 7 is T or S; wherein Xaa at position 8 is R, Q, K, S, or Y; and (b) a light chain CDRs comprising: (i) a CDR1 of the formula RASESXaaDXaaYGISFXaaXaa (SEQ ID NO:19), wherein Xaa at position 6 is I or V; Xaa at position 8 is N or S; Xaa at position 14 is L or M; Xaa at position 15 is A, T, or N; (ii) a CDR2 of the formula AASNXaaGS (SEQ ID NO:20), wherein Xaa at position 5 is R, L, or Q; and (iii) a CDR 3 of the formula QQSKXaaVPRT (SEQ ID NO:21), wherein Xaa at position 5 is T, A, S, or E; wherein the antibody is not an antibody comprising (a) a heavy chain CDRs comprising a CDR1 region of SEQ ID NO:22, a CDR2 region of SEQ ID NO:23, and a CDR3 region of SEQ ID NO:24; and (b) a light chain CDRs comprising a CDR1 region of SEQ ID NO:25, a CDR2 region of SEQ ID NO:26, and a CDR3 region of SEQ ID NO:27.

In another aspect, the invention is an antibody comprising a fragment or a region of the antibody A5 (interchangeably termed "A5" herein). In one embodiment, the fragment is a light chain of the antibody A5 as shown in SEQ ID NO:29. In another embodiment, the fragment is a heavy chain of the antibody A5 as shown in SEQ ID NO:28. In yet another embodiment, the fragment contains one or more variable regions from a light chain and/or a heavy chain of the antibody A5. In yet another embodiment, the fragment contains one or more CDRs from a light chain and/or a heavy chain of the antibody A5 as shown in FIGS. 1A and 1B.

In another aspect, the invention is an antibody comprising a light chain that is encoded by a polynucleotide that is produced by a host cell with a deposit number of ATCC No. PTA-5682. In another aspect, the invention is an antibody comprising a heavy chain that is encoded by a polynucleotide that is produced by a host cell with a deposit number of ATCC No. PTA-5683. In another aspect, the invention is an antibody comprising (a) a light chain that is encoded by a polynucleotide that is produced by a host cell with a deposit number of ATCC No. PTA-5682; and (b) a heavy chain that is encoded by a polynucleotide that is produced by a host cell with a deposit number of ATCC No. PTA-5683 (for convenience herein, the polynucleotide(s) produced by a deposited host cell are referred to as having a deposit number of ATCC NOs. PTA-5682 and PTA-5683). In another aspect, the invention is an antibody comprising a light chain variable region encoded by a polynucleotide that is produced by a host cell with a deposit number of ATCC No. PTA-5682. In another aspect, the invention is an antibody comprising a heavy chain variable region encoded by a polynucleotide that is produced by a host cell with a deposit number of ATCC No. PTA-5683. In another aspect, the invention is an antibody comprising (a) a heavy chain variable region encoded by a polynucleotide that is produced by a host cell with a deposit number of ATCC No. PTA-5683 and (b) a light chain variable region encoded by a polynucleotide that is produced by a host cell with a deposit number of ATCC No. PTA-5682. In still another aspect, the invention is an antibody comprising one or more CDR(s) encoded by (a) a polynucleotide that is produced by a host cell with a deposit number of ATCC No. PTA-5682; and/or (b) a heavy chain that is encoded by a polynucleotide that is produced by a host cell with a deposit number of ATCC No. PTA-5683.

In some embodiments, the antibody comprises a modified constant region, such as a constant region that is immunologically inert, e.g., does not trigger complement mediated lysis, or does not stimulate antibody-dependent cell mediated cytotoxicity (ADCC). In other embodiments, the constant region is modified as described in *Eur. J. Immunol.* (1999) 29:2613-2624; PCT Application No. PCT/GB99/01441; and/or UK Patent Application No. 9809951.8. In still other embodiments, the antibody comprises a human heavy chain IgG2a constant region comprising the following mutations: A330P331 to S330S331 (amino acid numbering with reference to the wildtype IgG2a sequence). Eur. J. Immunol. (1999) 29:2613-2624.

In another aspect, the invention provides polypeptides (which may or may not be an antibody) comprising any one or more of the following: a) one or more CDR(s) of antibody A5 shown in FIGS. 1A and 1B; b) CDR H3 from the heavy chain of antibody A5 shown in FIG. 1A; c) CDR L3 from the light chain of antibody A5 shown in FIG. 11B; d) three CDRs from the light chain of antibody A5 shown in FIG. 1B; e) three CDRs from the heavy chain of antibody A5 shown in FIG. 1A; and f) three CDRs from the light chain and three CDRs from the heavy chain, of antibody A5 shown in FIGS. 1A and 1B. The invention further provides polypeptides (which may or may not be an antibody) comprising any one or more of the following: a) one or more (one, two, three, four, five, or six) CDR(s) derived from antibody A5 shown in FIGS. 1A and 1B; b) a CDR derived from CDR H3 from the heavy chain of antibody A5 shown in FIG. 1A; and/or c) a CDR derived from CDR L3 from the light chain of antibody A5 shown in FIG. 1B.

The invention also provides polypeptides (which may or may not be an antibody) comprising any one or more of the following: (a) a sequence of the formula GYTFTSYXaaXaaH (SEQ ID NO: 16), wherein Xaa at position 8 is R or W; and Xaa at position 9 is I, L, R, or M; wherein the sequence is not GYTFTSYWMH (SEQ ID NO:22); (b) a sequence of the formula GYTFTSYXaaXaaH (SEQ ID NO:16), wherein Xaa at position 8 is R; and Xaa at position 9 is I, L, or R; (c) a sequence of the formula EIYPSNXaaRTNYNEKFXaaS (SEQ ID NO: 17), wherein Xaa at position 7 is A, T, S, or G; and Xaa at position 16 is K or E; wherein the sequence is not EIYPSNGRTNYNEKFKS (SEQ ID NO:23); (d) a sequence of the formula EIYPSNXaaRTNYNEKFXaaS (SEQ ID NO:17), wherein Xaa at position 7 is A, T, or S; and Xaa at position 16 is K or E; (e) a sequence of the formula KYYYGNXaaXaaRSWYFDV (SEQ ID NO: 18), wherein Xaa at position 7 is T or S; wherein Xaa at position 8 is R, Q, K, S, or Y; wherein the sequence is not KYYYGNSYRSWYFDV (SEQ ID NO:24); (f) a sequence of the formula KYYYGNXaaXaaRSWYFDV (SEQ ID NO:18), wherein Xaa at position 7 is T; wherein Xaa at position 8 is R, Q, K, or S; (g) a sequence of the formula RASESXaaDXaaYGISFXaaXaa (SEQ ID NO: 19), wherein Xaa at position 6 is I or V; Xaa at position 8 is N or S; Xaa at position 14 is L or M; Xaa at position 15 is A, T, or N; wherein the sequence is not RASESVDNYGISFMN (SEQ ID NO:25); (h) a sequence of the formula RASESXaaDXaaYGISFXaaXaa (SEQ ID NO:19), wherein Xaa at position 6 is I; Xaa at position 8 is N or S; Xaa at position 14 is L; Xaa at position 15 is A or T; (i) a sequence of the formula AASNXaaGS (SEQ ID NO:20), wherein Xaa at position 5 is R or L; (j) a sequence of the formula QQSKXaaVPRT (SEQ ID NO:21), wherein Xaa at position 5 is T, A, or S.

In some embodiments, the invention provides any of the above antibodies, further wherein the antibody is human. In other embodiments, the invention provides any of the above antibodies, further wherein the antibody is humanized. In some embodiments, the antibody is a monoclonal antibody. In some embodiments, the antibody binds human trkC. In some embodiments, the antibody binds preferentially to human trkC. In some embodiments, the antibody binds to human trkC with a $K_D$ of less than about 5 nM. In some embodiments, the antibody further binds rodent trkc.

It is understood that embodiments (polynucleotide or polypeptide) that consist of the identical sequence (polynucleotide or amino acid) to the sequence of mouse monoclonal antibody, 2256, are specifically excluded. The amino acid sequence of 2256 variable regions (including CDR regions) are shown in FIGS. 2A and 2B.

In another aspect, the invention provides an isolated polynucleotide comprising a polynucleotide encoding a fragment or a region of the antibody A5 (interchangeably termed "A5" herein). In one embodiment, the fragment is a light chain of the antibody A5 as shown in FIG. 1B. In another embodiment, the fragment is a heavy chain of the antibody A5 as shown in FIG. 1A. In yet another embodiment, the fragment contains one or more variable regions from a light chain and/or a heavy chain of the antibody A5. In yet another embodiment, the fragment contains one or more complementarity determining regions (CDRs) from a light chain and/or a heavy chain of the antibody A5 as shown in FIGS. 1A and 1B.

In another aspect, the invention is an isolated polynucleotide comprising a polynucleotide that encodes for antibody A5. In some embodiments, the polynucleotide comprises either or both of the polynucleotide shown in SEQ ID NOS:11 and 13. In another embodiment, the polynucleotide comprises either or both of the polynucleotide shown in SEQ ID NOS:10 and 12.

In another aspect, the invention is an isolated polynucleotide that encodes for an A5 light chain with a deposit number of ATCC No. PTA-5682. In another aspect, the invention is an isolated polynucleotide that encodes for an A5 heavy chain with a deposit number of ATCC No. PTA-5683. In yet another aspect, the invention is an isolated polynucleotide comprising (a) a variable region encoded in the polynucleotide with a deposit number of ATCC No. PTA-5682 and (b) a variable region encoded in the polynucleotide with a deposit number of ATCC No. PTA-5683. In another aspect, the invention is an isolated polynucleotide comprising (a) one or more CDR encoded in the polynucleotide with a deposit number of ATCC No. PTA-5682; and/or (b) one or more CDR encoded in the polynucleotide with a deposit number of ATCC No. PTA-5683.

In another aspect, the invention provides polynucleotides encoding any of the antibodies (including antibody fragments) or polypeptides described herein.

In another aspect, the invention provides vectors (including expression and cloning vectors) and host cells comprising any of the polynucleotide disclosed herein.

In another aspect, the invention is a host cell comprising a polynucleotide encoding A5 light chain and a polynucleotide encoding A5 heavy chain, wherein the polynucleotide(s) encoding A5 light chain has a deposit number of ATCC No. PTA-5682, and the polynucleotide encoding A5 heavy chain has a deposit number of ATCC No. PTA-5683 (for convenience herein, the polynucleotide(s) produced by a deposited host cell are referred to as having a deposit number of ATCC Nos. PTA-5682 and PTA-5683). In some embodiments, the host cell comprises polynucleotide comprising (a) a variable region encoded in the polynucleotide with a deposit number of ATCC No. PTA-5682 and/or (b) a variable region encoded in the polynucleotide with a deposit number of ATCC No. PTA-5683. In some embodiments, the host cell comprises a polynucleotide encoding (a) one or more CDR encoded in the polynucleotide with a deposit number of ATCC No. PTA-5682; and/or (b) one or more CDR encoded in the polynucleotide with a deposit number of ATCC No. PTA-5683. In some embodiments, the host cell is a mammalian cell.

In another aspect, the invention provides a polynucleotide deposited at the ATCC as deposit number ATCC No. PTA-5683. In another aspect, the invention provides a polynucleotide deposited at the ATCC as deposit number ATCC PTA-5682.

In another aspect, the invention is a complex of trkC bound by antibody A5. In some aspects, the complex is isolated. In some embodiments, the trkC is human.

In another aspect, the invention is a complex of trkC bound by any of the antibodies or polypeptides described herein. In some aspects, the complex is isolated.

In another aspect, the invention is a pharmaceutical composition comprising any of the polypeptides (including antibodies such as antibody A5) or polynucleotides described herein, such as pharmaceutical compositions comprising the antibody A5 or an antibody comprising a fragment of the antibody A5, and a pharmaceutically acceptable excipient.

In another aspect, the invention is a method of generating antibody A5 comprising preparing a host cell comprising an expression vector that encodes for antibody A5; culturing the host cell or progeny thereof under conditions that allow production of antibody A5; and purifying the antibody A5. In some embodiments, the polynucleotide comprises either or both of the polynucleotide shown in SEQ ID NOS:11 and 13.

In another embodiment, the polynucleotide comprises either or both of the polynucleotide shown in SEQ ID NOS:10 and 12.

In another aspect, the invention is a method of generating antibody A5 comprising expressing a polynucleotide encoding A5 light chain and a polynucleotide encoding A5 heavy chain in a suitable cell, wherein the polynucleotide encoding A5 light chain has a deposit number of ATCC No. PTA-5682, and the polynucleotide encoding A5 heavy chain has a deposit number of ATCC No. PTA-5683; generally followed by recovering and/or isolating the antibody.

In another aspect, the invention provides methods of generating any of the antibodies described herein by expressing one or more polynucleotides encoding the antibody (which may be separately expressed as a single light or heavy chain, or both a light and a heavy chain are expressed from one vector) in a suitable cell, generally followed by recovering and/or isolating the antibody or polypeptides of interest.

In another aspect, the invention is a method of activating human trkC or other mammalian trkC biological activity using any of the polypeptides (including antibodies such as antibody A5) disclosed herein. In one embodiment, the method comprises contacting human trkC with any of the polypeptides (including antibody A5) describe herein, whereby human trkC activity is activated.

In another aspect, the invention is a method of detecting trkC using any of the polypeptides (including antibodies, such as the antibody A5) described herein. The presence of trkC is detected by detecting a complex between trkC and any of the polypeptides described herein (such as antibody A5). The term "detection" as used herein includes qualitative and/or quantitative detection (measuring levels) with or without reference to a control.

In another aspect, the invention is a method of treating sensory neuropathy, such as a large fiber sensory neuropathy, by administering an effective amount of a composition comprising the antibody A5 or any of the polypeptide (including antibody) or polynucleotide embodiments described herein. In some embodiments, the sensory neuropathy is taxol-induced sensory neuropathy. In some embodiments, the sensory neuropathy is cisplatin-induced sensory neuropathy. In some embodiments, the sensory neuropathy is pyridoxine-induced sensory neuropathy.

In another aspect, the invention provides kits and compositions comprising any one or more of the compositions described herein. These kits, generally in suitable packaging and provided with appropriate instructions, are useful for any of the methods described herein.

The invention also provides any of the compositions described herein (such as antibodies, polypeptides, polynucleotides) for any of the uses described herein, whether in the context (for example) of use as a medicament and/or manufacture of a medicament.

In some embodiments, the polypeptides or antibodies of the invention do not include the exclusions described herein. With respect to the formulae herein, as is evident to the one skilled in the art, each amino acid substituent may be independently selected. The invention also provides formulae in one or more amino acid substituents are eliminated.

BRIEF DESCRIPTION OF THE FIGURES

FIG. 1A: shows the amino acid sequence of the heavy chain variable region of the A5 antibody (labeled A5-H)(SEQ ID NO:1). The extended CDR is boxed, and the Chothia CDRs and Kabat CDRs are depicted by italic text and bold text, respectively. Variable region amino acid residues are numbered sequentially.

FIG. 1B: shows the amino acid sequence of the light chain variable region of the A5 antibody (labeled A5-L)(SEQ ID NO:2). The extended CDR is boxed, and the Chothia CDRs and Kabat CDRs are depicted by italic text and bold text, respectively. Variable region amino acid residues are numbered sequentially.

FIG. 2A: shows the amino acid sequence of the heavy chain variable region of the mouse monoclonal agonist anti-trkC antibody 2256 (labeled 2256H). The extended CDR is boxed, and the Chothia CDRs and Kabat CDRs are depicted by italic text and bold text, respectively. Variable region amino acid residues are numbered sequentially.

FIG. 2B: shows the amino acid sequence of the light chain variable region of the mouse monoclonal agonist anti-trkC antibody 2256 (labeled 2256L). The extended CDR is boxed, and the Chothia CDRs and Kabat CDRs are depicted by italic text and bold text, respectively. Variable region amino acid residues are numbered sequentially.

DETAILED DESCRIPTION OF THE INVENTION

Figure 3:
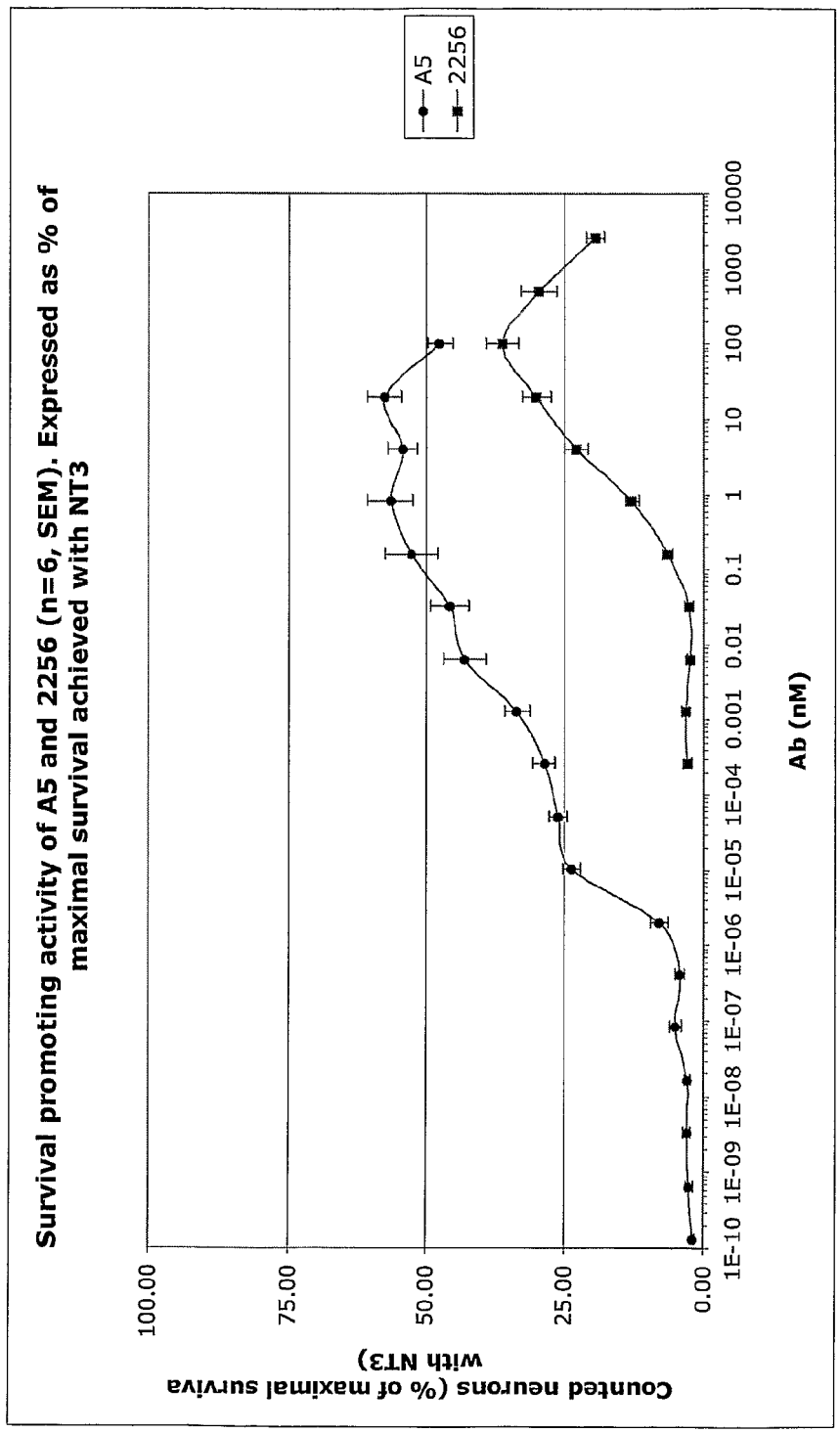
FIG. 3: is a graph showing agonist activity of mouse monoclonal agonist anti-trkC antibody 2256 and antibody A5 in rat E20 trigeminal neuronal survival assay.

The invention disclosed herein provides antibodies and polypeptides (such as A5) that bind trkc, and methods of making and using these antibodies. In some embodiments, the invention provides a humanized antibody, A5, which binds to trkC receptor ("trkC"), and methods of making and using this antibody. The invention also provides A5 polypeptides (including antibodies) that bind trkc, and polynucleotides encoding A5 antibody and/or polypeptide.

The invention disclosed herein also provides methods for preventing and/or treating sensory neuropathy (such as taxol-induced sensory neuropathy) in an individual by administration of a therapeutically effective amount of an agonist anti-trkC antibody.

General Techniques

The practice of the present invention will employ, unless otherwise indicated, conventional techniques of molecular biology (including recombinant techniques), microbiology, cell biology, biochemistry and immunology, which are within the skill of the art. Such techniques are explained fully in the literature, such as, Molecular Cloning: A Laboratory Manual, second edition (Sambrook et al., 1989) Cold Spring Harbor Press; Oligonucleotide Synthesis (M. J. Gait, ed., 1984);

*Methods in Molecular Biology*, Humana Press; *Cell Biology: A Laboratory Notebook* (J. E. Cellis, ed., 1998) Academic Press; Animal Cell Culture (R. I. Freshney, ed., 1987); *Introduction to Cell and Tissue Culture* (J. P. Mather and P. E. Roberts, 1998) *Plenum Press; Cell and Tissue Culture: Laboratory Procedures* (A. Doyle, J. B. Griffiths, and D. G. Newell, eds., 1993-1998) J. Wiley and Sons; *Methods in Enzymology* (Academic Press, Inc.); *Handbook of Experimental Immunology* (D. M. Weir and C. C. Blackwell, eds.); *Gene Transfer Vectors for Mammalian Cells* (J. M. Miller and M. P. Calos, eds., 1987); *Current Protocols in Molecular Biology* (F. M. Ausubel et al., eds., 1987); *PCR: The Polymerase Chain Reaction*, (Mullis et al., eds., 1994); *Current Protocols in Immunology* (J. E. Coligan et al., eds., 1991); *Short Protocols in Molecular Biology* (Wiley and Sons, 1999); *Immunobiology* (C. A. Janeway and P. Travers, 1997); *Antibodies* (P. Finch, 1997); *Antibodies: a practical approach* (D. Catty., ed., IRL Press, 1988-1989); *Monoclonal antibodies: a practical approach* (P. Shepherd and C. Dean, eds., Oxford University Press, 2000); *Using antibodies: a laboratory manual* (E. Harlow and D. Lane (Cold Spring Harbor Laboratory Press, 1999); *The Antibodies* (M. Zanetti and J. D. Capra, eds., Harwood Academic Publishers, 1995).

DEFINITIONS

An "antibody" is an immunoglobulin molecule capable of specific binding to a target, such as a carbohydrate, polynucleotide, lipid, polypeptide, etc., through at least one antigen recognition site, located in the variable region of the immunoglobulin molecule. As used herein, the term encompasses not only intact polyclonal or monoclonal antibodies, but also fragments thereof (such as Fab, Fab', F(ab')$_2$, Fv), single chain (ScFv), mutants thereof, fusion proteins comprising an antibody portion, and any other modified configuration of the immunoglobulin molecule that comprises an antigen recognition site. An antibody includes an antibody of any class, such as IgG, IgA, or IgM (or sub-class thereof), and the antibody need not be of any particular class. Depending on the antibody amino acid sequence of the constant domain of its heavy chains, immunoglobulins can be assigned to different classes. There are five major classes of immunoglobulins: IgA, IgD, IgE, IgG, and IgM, and several of these may be further divided into subclasses (isotypes), e.g., IgG1, IgG2, IgG3, IgG4, IgA1 and IgA2. The heavy-chain constant domains that correspond to the different classes of immunoglobulins are called alpha, delta, epsilon, gamma, and mu, respectively. The subunit structures and three-dimensional configurations of different classes of immunoglobulins are well known.

As used herein, "monoclonal antibody" refers to an antibody obtained from a population of substantially homogeneous antibodies, i.e., the individual antibodies comprising the population are identical except for possible naturally-occurring mutations that may be present in minor amounts. Monoclonal antibodies are highly specific, being directed against a single antigenic site. Furthermore, in contrast to polyclonal antibody preparations, which typically include different antibodies directed against different determinants (epitopes), each monoclonal antibody is directed against a single determinant on the antigen. The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by recombinant DNA methods such as described in U.S. Pat. No. 4,816,567. The monoclonal antibodies may also be isolated from phage libraries generated using the techniques described in McCafferty et al., 1990, *Nature*, 348:552-554, for example.

As used herein, "human antibody" means an antibody having an amino acid sequence corresponding to that of an antibody produced by a human and/or has been made using any of the techniques for making human antibodies known in the art or disclosed herein. This definition of a human antibody includes antibodies comprising at least one human heavy chain polypeptide or at least one human light chain polypeptide. One such example is an antibody comprising murine light chain and human heavy chain polypeptides. Human antibodies can be produced using various techniques known in the art. In one embodiment, the human antibody is selected from a phage library, where that phage library expresses human antibodies (Vaughan et al., 1996, *Nature Biotechnology*, 14:309-314; Sheets et al., 1998, *PNAS*, (USA) 95:6157-6162; Hoogenboom and Winter, 1991, *J. Mol. Biol.*, 227:381; Marks et al., 1991, *J. Mol. Biol.*, 222:581). Human antibodies can also be made by introducing human immunoglobulin loci into transgenic animals, e.g., mice in which the endogenous immunoglobulin genes have been partially or completely inactivated. This approach is described in U.S. Pat. Nos. 5,545,807; 5,545,806; 5,569,825; 5,625,126; 5,633,425; and 5,661,016. Alternatively, the human antibody may be prepared by immortalizing human B lymphocytes that produce an antibody directed against a target antigen (such B lymphocytes may be recovered from an individual or may have been immunized in vitro). See, e.g. Cole et al., *Monoclonal Antibodies and Cancer Therapy*, Alan R. Liss, p. 77 (1985); Boerner et al., 1991, *J. Immunol.*, 147 (1):86-95; and U.S. Pat. No. 5,750,373.

As used herein, the terms "A5" and "antibody A5" are used interchangeably to refer to an antibody comprising the amino acid sequence of the heavy chain and light chain variable regions shown in FIGS. 1A and 1B. The CDR portions of antibody A5 (including Chothia and Kabat CDRs) are diagrammatically depicted in FIGS. 1A and 1B. SEQ ID NOS: 11 and 13 show polynucleotides encoding the heavy and light chain variable regions of A5, respectively. The characterization of A5 is described in the Examples. Different biological functions are associated with A5, including, but not limited to, ability to bind to and activate a trkC receptor and/or downstream pathways mediated by the trkC signaling function. In some embodiments, the term "A5" refers to immunoglobulin encoded by (a) a polynucleotide encoding A5 light chain that has a deposit number of ATCC No. PTA-5682, and (b) a polynucleotide encoding A5 heavy chain that has a deposit number of ATCC No. PTA-5683.

The terms "polypeptide", "oligopeptide", "peptide" and "protein" are used interchangeably herein to refer to polymers of amino acids of any length. The polymer may be linear or branched, it may comprise modified amino acids, and it may be interrupted by non-amino acids. The terms also encompass an amino acid polymer that has been modified naturally or by intervention; for example, disulfide bond formation, glycosylation, lipidation, acetylation, phosphorylation, or any other manipulation or modification, such as conjugation with a labeling component. Also included within the definition are, for example, polypeptides containing one or more analogs of an amino acid (including, for example, unnatural amino acids, etc.), as well as other modifications known in the art. It is understood that, because the polypeptides of this invention are based upon an antibody, the polypeptides can occur as single chains or associated chains.

"Polynucleotide," or "nucleic acid," as used interchangeably herein, refer to polymers of nucleotides of any length, and include DNA and RNA. The nucleotides can be deoxyribonucleotides, ribonucleotides, modified nucleotides or bases, and/or their analogs, or any substrate that can be incorporated into a polymer by DNA or RNA polymerase. A polynucleotide may comprise modified nucleotides, such as methylated nucleotides and their analogs. If present, modification to the nucleotide structure may be imparted before or after assembly of the polymer. The sequence of nucleotides may be interrupted by non-nucleotide components. A polynucleotide may be further modified after polymerization, such as by conjugation with a labeling component. Other types of modifications include, for example, "caps", substitution of one or more of the naturally occurring nucleotides with an analog, internucleotide modifications such as, for example, those with uncharged linkages (e.g., methyl phosphonates, phosphotriesters, phosphoamidates, cabamates, etc.) and with charged linkages (e.g., phosphorothioates, phosphorodithioates, etc.), those containing pendant moieties, such as, for example, proteins (e.g., nucleases, toxins, antibodies, signal peptides, ply-L-lysine, etc.), those with intercalators (e.g., acridine, psoralen, etc.), those containing chelators (e.g., metals, radioactive metals, boron, oxidative metals, etc.), those containing alkylators, those with modified linkages (e.g., alpha anomeric nucleic acids, etc.), as well as unmodified forms of the polynucleotide(s). Further, any of the hydroxyl groups ordinarily present in the sugars may be replaced, for example, by phosphonate groups, phosphate groups, protected by standard protecting groups, or activated to prepare additional linkages to additional nucleotides, or may be conjugated to solid supports. The 5' and 3' terminal OH can be phosphorylated or substituted with amines or organic capping group moieties of from 1 to 20 carbon atoms. Other hydroxyls may also be derivatized to standard protecting groups. Polynucleotides can also contain analogous forms of ribose or deoxyribose sugars that are generally known in the art, including, for example, 2'-O-methyl-, 2'-O-allyl, 2'-fluoro- or 2'-azido-ribose, carbocyclic sugar analogs, α-anomeric sugars, epimeric sugars such as arabinose, xyloses or lyxoses, pyranose sugars, furanose sugars, sedoheptuloses, acyclic analogs and abasic nucleoside analogs such as methyl riboside. One or more phosphodiester linkages may be replaced by alternative linking groups. These alternative linking groups include, but are not limited to, embodiments wherein phosphate is replaced by P(O)S("thioate"), P(S)S ("dithioate"), "(O)NR$_2$ ("amidate"), P(O)R, P(O)OR', CO or CH$_2$ ("formacetal"), in which each R or R' is independently H or substituted or unsubstituted alkyl (1-20 C) optionally containing an ether (—O—) linkage, aryl, alkenyl, cycloalkyl, cycloalkenyl or araldyl. Not all linkages in a polynucleotide need be identical. The preceding description applies to all polynucleotides referred to herein, including RNA and DNA.

A "variable region" of an antibody refers to the variable region of the antibody light chain or the variable region of the antibody heavy chain, either alone or in combination. The variable regions of the heavy and light chain each consist of four framework regions (FR) connected by three complementarity determining regions (CDRs) also known as hypervariable regions. The CDRs in each chain are held together in close proximity by the FRs and, with the CDRs from the other chain, contribute to the formation of the antigen-binding site of antibodies. There are at least two techniques for determining CDRs: (1) an approach based on cross-species sequence variability (i.e., Kabat et al. *Sequences of Proteins of Immunological Interest*, (5th ed., 1991, National Institutes of Health, Bethesda Md.)); and (2) an approach based on crystallographic studies of antigen-antibody complexes (Al-lazikani et al (1997) *J. Molec. Biol.* 273:927-948)). As used herein, a CDR may refer to CDRs defined by either approach or by a combination of both approaches.

A "constant region" of an antibody refers to the constant region of the antibody light chain or the constant region of the antibody heavy chain, either alone or in combination.

As used herein, "trkC" refers to the trkC receptor polypeptide, a member of the tyrosine kinase superfamily. trkC encompasses the native trkC receptor of any mammalian species, including but not limited to, human, canine, feline, bovine, equine, primate, and rodent (including mouse and rat). The extracellular domain of full-length native trkC has been defined with reference to homologous or otherwise similar structures identified in various other proteins. The domains have been designated starting at the N-terminus of the mature trkC receptor as: 1) a first cysteine-rich domain extending from amino acid 1 to amino acid 48; 2) a leucine-rich domain extending from amino acid 49 to amino acid 120; 3) a second cysteine-rich domain extending from amino acid 121 to amino acid 177; 4) a first immunoglobulin-like domain extending from about amino acid 196 to amino acid 257; and 5) a second immunoglobulin-like domain extending from about amino acid 288 to amino acid 351. See, e.g., PCT Publication No. WO 0198361. The domain structure of the extracellular domain of trkC receptor has also been designated by reference to a crystal structure as follows: domain 1 from amino acid 1 to amino acid 47; domain 2 from amino acid 48 to amino acid 130; domain 3 from amino acid 131 to amino acid 177; domain 4 from amino acid 178 to amino acid 165; and domain 5 from amino acid 166 to amino acid 381. See, e.g., PCT WO 01/98361; Urfer et al. *J. Biol. Chem.* 273: 5829-5840 (1998). Also included are variants of trkC, examples of which include, but are not limited to, variants without a kinase domain (Shelton, et al., *J. Neurosci.* 15(1): 477-491, 1995), and variants with a modified kinase domain (Shelton, et al., *J. Neurosci.* 15(1):477-491, 1995).

An "agonist anti-trkc antibody" (interchangeably termed "anti-trkC agonist antibody" or "anti-trkC antibody") refers to an antibody that is able to bind to and activate a trkC receptor and/or downstream pathway(s) mediated by the trkC signaling function. For example, the agonist antibody may bind to the extracellular domain of a trkC receptor and thereby cause dimerization of the receptor, resulting in activation of the intracellular catalytic kinase domain. Consequently, this may result in stimulation of growth and/or differentiation of cells expressing the receptor in vitro and/or in vivo. In some embodiments, an agonist anti-trkC antibody binds to trkC and activates a trkC biological activity. In some embodiments, an agonist antibody useful in the methods of the invention recognizes domain V and/or domain IV of trkC. See Urfer et al., *J. Biol. Chem.* 273: 5829-5840 (1998). Examples of agonist anti-trkC antibodies are provided herein.

"Biological activity", when used in conjunction with the agonist anti-trkC antibodies of the present invention, generally refers to having the ability to bind and activate the trkC receptor tyrosine kinase and/or a downstream pathway mediated by the trkC signaling function. As used herein, "biological activity" encompasses one or more effector functions in common with those induced by action of NT-3, the native ligand of trkC, on a trkC-expressing cell. A "biological activity" of trkC can also encompass downstream signaling pathway(s) or effector functions that are different than those induced by action of NT-3. Without limitation, biological activities include any one or more of the following: ability to bind and activate trkc; ability to promote trkC receptor dimerization and activating trkc; the ability to promote the development, survival, function, maintenance and/or regeneration of cells (including damaged cells), in particular neurons in vitro or in vivo, including peripheral (sympathetic, sensory, and enteric) neurons, and central (brain and spinal cord) neurons, and non-neuronal cells, e.g. peripheral blood leukocytes. As evident by this disclosure to one skilled in the art, these principles apply to polypeptide embodiments.

An epitope that "preferentially binds" or "specifically binds" (used interchangeably herein) to an antibody or a polypeptide is a term well understood in the art, and methods to determine such specific or preferential binding are also well known in the art. A molecule is said to exhibit "specific binding" or "preferential binding" if it reacts or associates more frequently, more rapidly, with greater duration and/or with greater affinity with a particular cell or substance than it does with alternative cells or substances. An antibody "specifically binds" or "preferentially binds" to a target if it binds with greater affinity, avidity, more readily, and/or with greater duration than it binds to other substances. For example, an antibody that specifically or preferentially binds to a trkc epitope is an antibody that binds this trkc epitope with greater affinity, avidity, more readily, and/or with greater duration than it binds to other trkC epitopes or non-trkC epitopes. It is also understood by reading this definition that, for example, an antibody (or moiety or epitope) that specifically or preferentially binds to a first target may or may not specifically or preferentially bind to a second target. As such, "specific binding" or "preferential binding" does not necessarily require (although it can include) exclusive binding. Generally, but not necessarily, reference to binding means preferential binding.

As used herein, "immunospecific" binding of antibodies refers to the antigen specific binding interaction that occurs between the antigen-combining site of an antibody and the specific antigen recognized by that antibody (i.e., the antibody reacts with the protein in an ELISA or other immunoassay, and does not react detectably with unrelated proteins).

As used herein, "substantially pure" refers to material which is at least 50% pure (i.e., free from contaminants), more preferably at least 90% pure, more preferably at least 95% pure, more preferably at least 98% pure, more preferably at least 99% pure.

A "host cell" includes an individual cell or cell culture that can be or has been a recipient for vector(s) for incorporation of polynucleotide inserts. Host cells include progeny of a single host cell, and the progeny may not necessarily be completely identical (in morphology or in genomic DNA complement) to the original parent cell due to natural, accidental, or deliberate mutation. A host cell includes cells transfected in vivo with a polynucleotide(s) of this invention.

As used herein, "Fc receptor" and "FcR" describe a receptor that binds to the Fc region of an antibody. The preferred FcR is a native sequence human FcR. Moreover, a preferred FcR is one which binds an IgG antibody (a gamma receptor) and includes receptors of the FcγRI, FcγRII, and FcγRIII subclasses, including allelic variants and alternatively spliced forms of these receptors. FcγRII receptors include FcγRIIA (an "activating receptor") and FcγRIIB (an "inhibiting receptor"), which have similar amino acid sequences that differ primarily in the cytoplasmic domains thereof. FcRs are reviewed in Ravetch and Kinet, 1991, *Ann. Rev. Immunol.*, 9:457-92; Capel et al., 1994, *Immunomethods*, 4:25-34; and de Haas et al., 1995, *J. Lab. Clin. Med.*, 126:330-41. "FcR" also includes the neonatal receptor, FcRn, which is responsible for the transfer of maternal IgGs to the fetus (Guyer et al., 1976, *J. Immunol.*, 117:587; and Kim et al., 1994, *J. Immunol.*, 24:249).

"Complement dependent cytotoxicity" and "CDC" refer to the lysing of a target in the presence of complement. The complement activation pathway is initiated by the binding of the first component of the complement system (C1q) to a molecule (e.g. an antibody) complexed with a cognate antigen. To assess complement activation, a CDC assay, e.g. as described in Gazzano-Santoro et al., *J. Immunol. Methods*, 202:163 (1996), may be performed.

A "functional Fc region" possesses at least one effector function of a native sequence Fc region. Exemplary "effector functions" include C1q binding; complement dependent cytotoxicity (CDC); Fc receptor binding; antibody-dependent cell-mediated cytotoxicity (ADCC); phagocytosis; down-regulation of cell surface receptors (e.g. B cell receptor; BCR), etc. Such effector functions generally require the Fc region to be combined with a binding domain (e.g. an antibody variable domain) and can be assessed using various assays known in the art for evaluating such antibody effector functions.

A "native sequence Fc region" comprises an amino acid sequence identical to the amino acid sequence of an Fc region found in nature. A "variant Fc region" comprises an amino acid sequence which differs from that of a native sequence Fc region by virtue of at least one amino acid modification, yet retains at least one effector function of the native sequence Fc region. Preferably, the variant Fc region has at least one amino acid substitution compared to a native sequence Fc region or to the Fc region of a parent polypeptide, e.g. from about one to about ten amino acid substitutions, and preferably from about one to about five amino acid substitutions in a native sequence Fc region or in the Fc region of the parent polypeptide. The variant Fc region herein will preferably possess at least about 80% sequence identity with a native sequence Fc region and/or with an Fc region of a parent polypeptide, and most preferably at least about 90% sequence identity therewith, more preferably at least about 95% sequence identity therewith.

As used herein "antibody-dependent cell-mediated cytotoxicity" and "ADCC" refer to a cell-mediated reaction in which nonspecific cytotoxic cells that express Fc receptors (FcRs) (e.g. natural killer (NK) cells, neutrophils, and macrophages) recognize bound antibody on a target cell and subsequently cause lysis of the target cell. ADCC activity of a molecule of interest can be assessed using an in vitro ADCC assay, such as that described in U.S. Pat. No. 5,500,362 or 5,821,337. Useful effector cells for such assays include peripheral blood mononuclear cells (PBMC) and NK cells. Alternatively, or additionally, ADCC activity of the molecule of interest may be assessed in vivo, e.g., in a animal model such as that disclosed in Clynes et al., 1998, *PNAS* (USA), 95:652-656.

As used herein, "treatment" is an approach for obtaining beneficial or desired clinical results. For purposes of this invention, beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total), whether detectable or undetectable. "Treatment" can also mean prolonging survival as compared to expected survival if not receiving treatment. "Treatment" is an intervention performed with the intention of preventing the development or altering the pathology of a disorder. Accordingly, "treatment" refers to both therapeutic treatment and prophylactic or preventative measures. Those in need of treatment include those already with the disorder as well as those in which the disorder is to be prevented. Specifically, the treatment may directly prevent, slow down or otherwise decrease the pathology of cellular degeneration of damage, such as the pathology of nerve cells, or may render cells, e.g., neurons, more susceptible to treatment by other therapeutic agents.

A "taxol-induced sensory neuropathy" is a neurological disorder resulting from treatment with the chemotherapeutic agent taxol or other taxanes. As used herein, "taxol-induced sensory neuropathy" refers to and includes any one or more symptoms associated with this neurological disorder. Taxol-induced sensory neuropathy may affect primary sensory neurons of various types, autonomic neurons comprising sympathetic neurons, and neurons of specialized sensation, such as gustatory, olfactory, acoustic, and vestibular. As used herein, a "taxol-induced sensory neuropathy" refers to a neurological disorder affecting the sensory neurons associated with or present in an individual during or following administration of the agent, taxol, or related taxanes. In some embodiments, "taxol-induced sensory neuropathy" is characterized by degeneration of peripheral sensory neurons (including large-fiber sensory neurons). In some embodiments, "taxol-induced sensory neuropathy" is characterized by any of the following: distal symmetrical paraesthesia, pall-hypaesthesia, loss of joint position sense, painful dysaesthesia, Lhermitte's sign, pain, progressive distal and/or proximal paresis, myalgia, paralytic ileus, orthostatic hypotension, and arrhythmia; and degeneration of peripheral sensory neurons (including large-fiber sensory neurons). These may be determined by a standard neurological examination, patient interview, or more specialized quantitative testing. These more specialized quantitative tests may include, but are not limited to, determination of conduction velocity of the affected neurons by, e.g. use of microneurography or other electrophysiological testing; quantitative and/or quantitative determination of ability to sense cutaneous stimulation, including, but not limited to, heat, light touch, vibration, or two point discrimination; tests of hearing; specialized tests of balance; specialized tests of proprioception, or kinesthetic sense; tests of autonomic function, including, but not limited to, test of blood pressure control; and tests of heart rate response to various physiological and pharmacological stimuli. These tests may also include tests of motor skill.

As used herein, "taxol" refers to paclitaxel (TAXOL®, Bristol-Myers Squibb Oncology, Princeton, N.J.), docetaxel (TAXOTERE®, Rhône-Poulenc Rorer, Antony, France), and other taxanes. Taxol (including other taxanes) may be administered either alone, or in combination with other drugs. Taxol is approved for and commonly used for treating various malignancies, including Kaposi's sarcoma and those of the breast, ovary, and lung. Taxol is also used to treat other malignancies of the prostate, head and neck, as well as various hematological malignancies. Taxol is also given during bone marrow transplants.

An "effective amount" (for example, in the taxol-induced sensory neuropathy context) is an amount sufficient to effect beneficial or desired clinical results including clinical results or delaying the onset of the disease. An effective amount can be administered in one or more administrations. For purposes of this invention, an effective amount of an agonist anti-trkC antibody described herein is an amount sufficient to ameliorate, stabilize, reverse, slow and/or delay progression of or prevent sensory neuropathy, such as a large-fiber sensory neuropathy, such as taxol-induced sensory neuropathy. An effective amount of an agonist anti-trkC antibody also encompasses an amount of an agonist anti-trkC antibody sufficient to enhance taxol treatment (therapeutic effect) of cancer (which can, in turn, mean that taxol dosage is increased and/or some other beneficial effect is observed such as reduction of side-effects of taxol treatment), as described herein. As is understood in the art, an effective amount of an agonist anti-trkC antibody may vary, depending on, inter alia, patient history as well as other factors such as the type (and/or dosage) of an agonist anti-trkc antibody used. As evident by this disclosure to one skilled in the art, these principles apply to polypeptide embodiments.

As used herein, administration "in conjunction" includes simultaneous administration and/or administration at different times. Administration in conjunction also encompasses administration as a co-formulation (e.g., an agonist anti-trkC antibody and taxol are present in the same composition) or administration as separate compositions. As used herein, administration in conjunction is meant to encompass any circumstance wherein an agonist anti-trkC antibody and taxol are administered to an individual, which can occur simultaneously and/or separately. As further discussed herein, it is understood that an agonist anti-trkC antibody and taxol can be administered at different dosing frequencies or intervals. For example, an agonist anti-trkC antibody can be administered weekly, while taxol can be administered less frequently. It is understood that the agonist anti-trkC antibody and taxol can be administered using the same route of administration or different routes of administration.

A "biological sample" encompasses a variety of sample types obtained from an individual and can be used in a diagnostic or monitoring assay. The definition encompasses blood and other liquid samples of biological origin, solid tissue samples such as a biopsy specimen or tissue cultures or cells derived therefrom, and the progeny thereof. The definition also includes samples that have been manipulated in any way after their procurement, such as by treatment with reagents, solubilization, or enrichment for certain components, such as proteins or polynucleotides, or embedding in a semi-solid or solid matrix for sectioning purposes. The term "biological sample" encompasses a clinical sample, and also includes cells in culture, cell supernatants, cell lysates, serum, plasma, biological fluid, and tissue samples.

An "individual" is a vertebrate, preferably a mammal, more preferably a human. Mammals include, but are not limited to, farm animals (such as cows), sport animals, pets (such as cats, dogs, and horses), primates, mice and rats.

As used herein, "vector" means a construct, which is capable of delivering, and preferably expressing, one or more gene(s) or sequence(s) of interest in a host cell. Examples of vectors include, but are not limited to, viral vectors, naked DNA or RNA expression vectors, plasmid, cosmid or phage vectors, DNA or RNA expression vectors associated with cationic condensing agents, DNA or RNA expression vectors encapsulated in liposomes, and certain eukaryotic cells, such as producer cells.

As used herein, "expression control sequence" means a nucleic acid sequence that directs transcription of a nucleic acid. An expression control sequence can be a promoter, such as a constitutive or an inducible promoter, or an enhancer. The expression control sequence is operably linked to the nucleic acid sequence to be transcribed.

As used herein, "pharmaceutically acceptable carrier" includes any material which, when combined with an active ingredient, allows the ingredient to retain biological activity and is non-reactive with the subject's immune system and non-toxic to the subject when delivered. Examples include, but are not limited to, any of the standard pharmaceutical carriers such as a phosphate buffered saline solution, water, emulsions such as oil/water emulsion, and various types of wetting agents. Preferred diluents for aerosol or parenteral administration are phosphate buffered saline or normal (0.9%) saline.

Compositions comprising such carriers are formulated by well known conventional methods (see, for example, *Remington's Pharmaceutical Sciences*, 18th edition, A. Gennaro, ed., Mack Publishing Co., Easton, Pa., 1990; and *Remington, The Science and Practice of Pharmacy* 20th Ed. Mack Publishing, 2000).

The term "$k_{off}$", as used herein, is intended to refer to the off rate constant for dissociation of an antibody from the antibody/antigen complex.

The term "$K_D$", as used herein, is intended to refer to the dissociation constant of an antibody-antigen interaction.

Compositions and Methods of Making the Compositions

This invention encompasses compositions, including pharmaceutical compositions, comprising an anti-trkC agonist antibody (such as an A5 antibody) or polypeptide described herein; and polynucleotides comprising sequences encoding the antibody (such as an A5 antibody) or polypeptide. As used herein, compositions comprise one or more antibodies or polypeptides (which may or may not be an antibody) that bind to trkC, and/or one or more polynucleotides comprising sequences encoding one or more antibodies or polypeptides that bind to trkC. These compositions may further comprise suitable excipients, such as pharmaceutically acceptable excipients including buffers, which are well known in the art.

The invention also encompasses isolated antibody, polypeptide and polynucleotide embodiments. The invention also encompasses substantially pure antibody, polypeptide and polynucleotide embodiments.

The antibodies and polypeptides of the invention are characterized by any (one or more) of the following characteristics: (a) binds to trkC receptor; (b) binds to one or more epitopes of trkC receptor; (c) binds to trkC receptor to activate trkC receptor and/or one or more downstream pathways mediated by the trkC signaling function; (d) binds to trkC receptor to activate trkC receptor and treat, prevent, reverse, or ameliorate one or more symptoms of sensory neuropathy (such as taxol-induced sensory neuropathy); (e) does not bind to and/or activate trkB or trkA; (f) displays favorable pharmacokinetic and bioavailability properties.

The binding properties of antibody A5, which binds human trkC with high affinity and slow dissociation kinetics, compared with murine anti-trkC antibody 2256 ("Mab 2256"), are summarized below. The amino acid sequences of A5 heavy and light chain variable regions are shown in FIG. 1. The amino acid sequences of Mab 2256 heavy and light chain variable regions are shown in FIG. 2.

| antibody | $K_D$ (nM) | $k_{off}$ (s−1) | $k_{on}$ (s−1) |
|---|---|---|---|
| 2256 (Fab) | 40 | 0.02 | 5.30e$^5$ |
| A5 (Fab) | 0.28 | 3.70e$^{-4}$ | 1.33e$^6$ |

"me$^m$" in the table means: m × 10$^n$.

Figure 4:
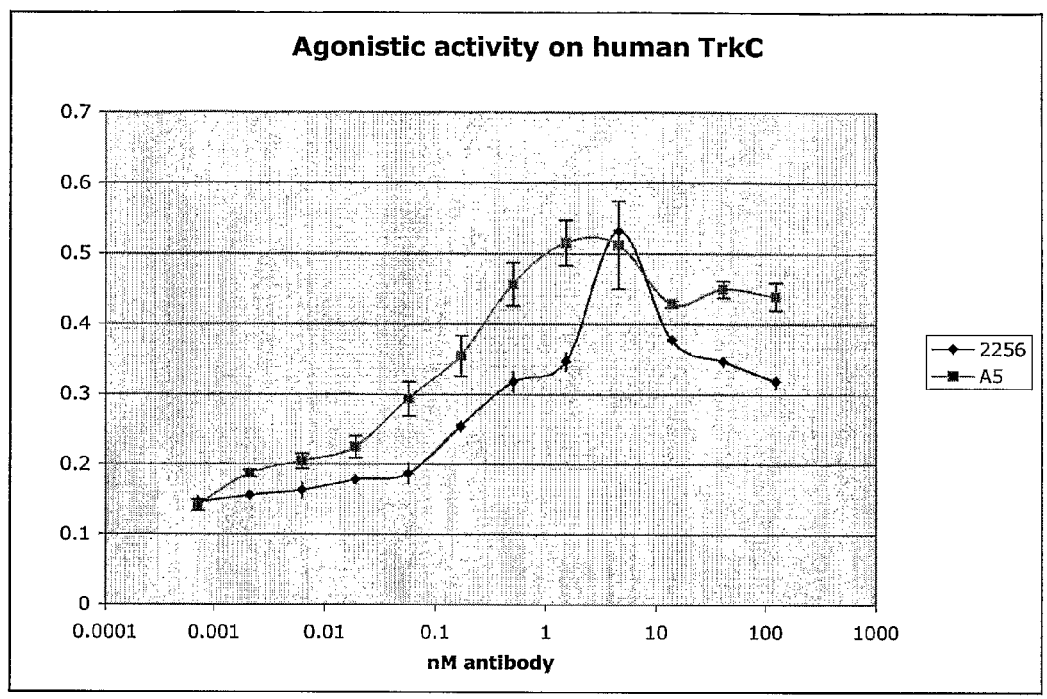
FIG. 4: is a graph comparing the activity of mouse monoclonal agonist anti-trkC antibody 2256 and antibody A5 as assayed using KIRA.

The A5 antibody and related antibodies (described herein) also exhibit a strong capacity to activate human trkc, as assessed by kinase receptor activation assay (KIRA) as described in Sadick et al, Exp. Cell Res. (1997) 234: 354-361, and to activate rat trkc, as assessed by in vitro neuronal survival assay. As shown in FIGS. 3 and 4, A5 is a potent agonist for both human and rodent trkC.

Accordingly, in some embodiments, the antibodies and polypeptides of the invention are further identified and characterized by: (g) high affinity binding to human trkC with slow dissociation kinetics (in some embodiments, with a $K_D$ of less than about 10 nM and/or a $k_{off}$ of slower than about 0.01 s$^{-1}$) and/or (h) ability to activate trkC-dependent survival of rat E12 trigeminal neurons with an EC50 of about 100 pM or less.

In some embodiments, the invention is an antibody comprising a light chain that is encoded by a polynucleotide that is produced by a host cell with a deposit number of ATCC No. PTA-5682. In another aspect, the invention is an antibody comprising a heavy chain that is encoded by a polynucleotide that is produced by a host cell with a deposit number of ATCC No. PTA-5683. The present invention also encompasses various formulations of A5 and equivalent antibody fragments (e.g., Fab, Fab', F(ab')$_2$, Fv, Fc, etc.), single chain (ScFv), mutants thereof, fusion proteins comprising an antibody portion, and any other modified configuration of A5 that comprises an antigen (trkC) recognition site of the required specificity. The equivalent antibodies of A5, including antibody and polypeptide fragments (which may or may not be antibodies) of A5, and polypeptides comprising polypeptide fragments of A5 are identified and characterized by any (one or more) of the criteria described above.

Accordingly, the invention provides any of the following, or compositions (including pharmaceutical compositions) comprising any of the following: (a) antibody A5; (b) a fragment or a region of the antibody A5; (c) a light chain of the antibody A5 as shown in SEQ ID NO:29; (c) a heavy chain of the antibody A5 as shown in SEQ ID NO:28; (d) one or more variable region(s) from a light chain and/or a heavy chain of the antibody A5; (e) one or more CDR(s) (one, two, three, four, five or six CDRs) of antibody A5 shown in FIGS. 1A and 1B; (f) CDR H3 from the heavy chain of antibody A5 shown in FIG. 1A; (g) CDR L3 from the light chain of antibody A5 shown in FIG. 1B; (h) three CDRs from the light chain of antibody A5 shown in FIG. 1B; (i) three CDRs from the heavy chain of antibody A5 shown in FIG. 1A; (j) three CDRs from the light chain and three CDRs from the heavy chain, of antibody A5 shown in FIGS. 1A and 1B; and (k) an antibody comprising any one of (b) through (j). The invention also provides polypeptides of any one or more of (a) through (j). In some embodiments, antibody A5 further comprises the human heavy chain IgG2a constant region containing the following mutations: A330P331 to S330S331 (amino acid numbering with reference to the wildtype IgG2a sequence; see Eur. J. Immunol. (1999) 29:2613-2624); and the human light chain kappa constant region.

The CDR portions of antibody A5 (including Chothia and Kabat CDRs) are diagrammatically depicted in FIGS. 1A and 1B. Determination of CDR regions is well within the skill of the art. It is understood that in some embodiments, CDRs can be a combination of the Kabat and Chothia CDR (also termed "combined CDRs" or "extended CDRs"). In some embodiments, the CDRs are the Kabat CDRs. In other embodiments, the CDRs are the Chothia CDRs.

In some embodiments, the invention provides an antibody which comprises at least one CDR that is substantially homologous to at least one CDR, at least two, at least three, at least four, at least 5 CDRs of A5 (or, in some embodiments substantially homologous to all 6 CDRs of A5, or derived from A5). Other embodiments include antibodies which have at least two, three, four, five, or six CDR(s) that are substantially homologous to at least two, three, four, five or six CDRs of A5 or derived from A5. It is understood that, for purposes of this invention, binding specificity and/or overall activity (which may be in terms of treating and/or preventing sensory neuropathy (such as large fiber sensory neuropathy, such as taxol-induced sensory neuropathy), or activating trkC-dependent survival of E12 rat trigeminal neurons) is generally retained, although the extent of activity may vary compared to A5 (may be greater or lesser). In some embodiments, one or more CDRs substantially homologous to at least one CDR, at least two, at least three, at least four, at least five or six CDRs of A5 are at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99% identical to at least one, at least two, at least three, at least four, at least five, or six CDRs of A5.

The invention also provides a polypeptide (which may or may not be an antibody) which comprises an amino acid sequence of A5 (shown in FIGS. 1A and 1B) that has any of the following: at least 5 contiguous amino acids, at least 8 contiguous amino acids, at least about 10 contiguous amino acids, at least about 15 contiguous amino acids, at least about 20 contiguous amino acids, at least about 25 contiguous amino acids, at least about 30 contiguous amino acids of a sequence of A5, wherein at least 3 of the amino acids are from a variable region of A5, with the understanding that embodiments that consist of the identical amino acid sequence to the amino acid sequence of mouse monoclonal antibody, 2256, are specifically excluded. The amino acid sequence of 2256 variable regions (including CDR regions) are shown in FIGS. 2A and 2B. In one embodiment, the variable region is from a light chain of A5. In another embodiment, the variable region is from a heavy chain of A5. In another embodiment, the 5 (or more) contiguous amino acids are from a complementarity determining region (CDR) of A5 shown in FIGS. 1A and 1B.

In another embodiment, the invention provides a polypeptide which comprises an amino acid sequence of A5 that has any of the following: at least 5 contiguous amino acids, at least 8 contiguous amino acids, at least about 10 contiguous amino acids, at least about 15 contiguous amino acids, at least about 20 contiguous amino acids, at least about 25 contiguous amino acids, at least about 30 contiguous amino acids of a sequence of A5, wherein the A5 sequence comprises any one or more of: amino acid residue R33 and/or I34 of CDR H1; A56 of CDR H2; T105 and/or R106 of CDR H3; I29, L37 and/or A38 of CDR L1; R58 of CDR L2; and/or T97 of CDR L3.

The binding affinity of an anti-trkC antibody to trkC (such as htrkC) can be about 0.10 to about 0.80 nM, about 0.15 to about 0.75 nM and about 0.18 to about 0.72 nM. In some embodiments, the binding affinity is about 2 pM, about 5 pM, about 10 pM, about 15 pM, about 20 pM, about 40 pM, or greater than about 40 pM. In one embodiment, the binding affinity is between about 2 pM and 22 pM. In other embodiments, the binding affinity is less than about 10 nM, about 5 nM, about 1 nM, about 900 pM, about 800 pM, about 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM. In some embodiments, the binding affinity is about 10 nM. In other embodiments, the binding affinity is less than about 10 nM. In other embodiments, the binding affinity is about 0.1 nM or about 0.07 nM. In other embodiments, the binding affinity is less than about 0.1 nM or less than about 0.07 nM. In other embodiments, the binding affinity is any of about 10 nM, about 5 nM, about 1 nM, about 900 pM, about 800 pM, about 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM to any of about 2 pM, about 5 pM, about 10 pM, about 15 pM, about 20 pM, or about 40 pM. In some embodiments, the binding affinity is any of about 10 nM, about 5 nM, about 1 nM, about 900 pM, about 800 pM, about 700 pM, about 600 pM, about 500 pM, about 400 pM, about 300 pM, about 200 pM, about 150 pM, about 100 pM, about 90 pM, about 80 pM, about 70 pM, about 60 pM, about 50 pM, about 40 pM, about 30 pM, about 10 pM. In still other embodiments, the binding affinity is about 2 pM, about 5 pM, about 10 pM, about 15 pM, about 20 pM, about 40 pM, or greater than about 40 pM.

The binding affinity of the antibody to trkC can be determined using methods well known in the art. One way of determining binding affinity of antibodies to trkC is by measuring affinity of monofunctional Fab fragments of the antibody, as described in the Examples. To obtain monofunctional Fab fragments, an antibody (for example, IgG) can be cleaved with papain or expressed recombinantly. The affinity of an anti-trkC Fab fragment of an antibody can be determined by surface plasmon resonance (BIAcore 3000™ surface plasmon resonance (SPR) system, BIAcore, INC, Piscaway N.J.), as described in the Examples. This protocol is suitable for use in determining binding affinity of an antibody to trkC of any species, including human trkC, trkC of another vertebrate (in some embodiments, mammalian) (such as mouse trkC, rat trkC, or primate trkC).

Other polypeptide and antibody embodiments of the invention are provided herein, including in the Summary of the Invention. The polypeptide of the invention may also be used as synthesis intermediates.

The invention also provides methods of making any of these antibodies or polypeptides. The antibodies of this invention can be made by procedures known in the art. The polypeptides can be produced by proteolytic or other degradation of the antibodies, by recombinant methods (i.e., single or fusion polypeptides) as described above or by chemical synthesis. Polypeptides of the antibodies, especially shorter polypeptides up to about 50 amino acids, are conveniently made by chemical synthesis. Methods of chemical synthesis are known in the art and are commercially available. For example, an A5 antibody could be produced by an automated polypeptide synthesizer employing the solid phase method. See also, U.S. Pat. Nos. 5,807,715; 4,816,567; and 6,331,415.

In another alternative, the antibodies can be made recombinantly using procedures that are well known in the art. In one embodiment, a polynucleotide encoding the variable and light chain regions of antibody A5 (SEQ ID NOS: 10 and 12) is cloned into a vector for expression or propagation. In another embodiment, the polynucleotide sequences shown in SEQ ID NOS:11 and 13 are cloned into one or more vectors for expression or propagation. The sequence encoding the antibody of interest may be maintained in a vector in a host cell and the host cell can then be expanded and frozen for future use. Vectors (including expression vectors) and host cells are further described herein.

The invention encompasses humanized antibodies, which refer to forms of non-human (e.g. murine) antibodies that are specific chimeric immunoglobulins, immunoglobulin chains, or fragments thereof (such as Fv, Fab, Fab', F(ab')$_2$ or other antigen-binding subsequences of antibodies) that contain minimal sequence derived from non-human immunoglobulin. For the most part, humanized antibodies are human immunoglobulins (recipient antibody) in which residues from a complementary determining region (CDR) of the recipient are replaced by residues from a CDR of a non-human species (donor antibody) such as mouse, rat, or rabbit having the desired specificity, affinity, and capacity. In some instances, Fv framework region (FR) residues of the human immunoglobulin are replaced by corresponding non-human residues. Furthermore, the humanized antibody may comprise residues that are found neither in the recipient antibody nor in the imported CDR or framework sequences, but are included to further refine and optimize antibody performance. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region or domain (Fc), typically that of a human immunoglobulin. Preferred are antibodies having Fc regions modified as described in WO 99/58572. Other forms of humanized antibodies have one or more CDRs (one, two, three, four, five, six) which are altered with respect to the original antibody, which are also termed one or more CDRs "derived from" one or more CDRs from the original antibody.

The invention also encompasses single chain variable region fragments ("scFv") of antibodies of this invention, such as A5. Single chain variable region fragments are made by linking light and/or heavy chain variable regions by using a short linking peptide. Bird et al. (1988) Science 242:423-426. An example of a linking peptide is (GGGGS)$_3$ (SEQ ID NO:3), which bridges approximately 3.5 nm between the carboxy terminus of one variable region and the amino terminus of the other variable region. Linkers of other sequences have been designed and used. Bird et al. (1988). Linkers can in turn be modified for additional functions, such as attachment of drugs or attachment to solid supports. The single chain variants can be produced either recombinantly or synthetically. For synthetic production of scFv, an automated synthesizer can be used. For recombinant production of scFv, a suitable plasmid containing polynucleotide that encodes the scFv can be introduced into a suitable host cell, either eukaryotic, such as yeast, plant, insect or mammalian cells, or prokaryotic, such as *E. coli*. Polynucleotides encoding the scFv of interest can be made by routine manipulations such as ligation of polynucleotides. The resultant scFv can be isolated using standard protein purification techniques known in the art.

Other forms of single chain antibodies, such as diabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites (see e.g., Holliger, P., et al. (1993) *Proc. Natl. Acad Sci. USA* 90:6444-6448; Poljak, R. J., et al. (1994) *Structure* 2:1121-1123).

For example, bispecific antibodies, monoclonal antibodies that have binding specificities for at least two different antigens, can be prepared using the antibodies disclosed herein. Methods for making bispecific antibodies are known in the art (see, e.g., Suresh et al., 1986, Methods in Enzymology 121: 210). Traditionally, the recombinant production of bispecific antibodies was based on the coexpression of two immunoglobulin heavy chain-light chain pairs, with the two heavy chains having different specificities (Millstein and Cuello, 1983, *Nature* 305, 537-539).

According to one approach to making bispecific antibodies, antibody variable domains with the desired binding specificities (antibody-antigen combining sites) are fused to immunoglobulin constant domain sequences. The fusion preferably is with an immunoglobulin heavy chain constant domain, comprising at least part of the hinge, CH2 and CH3 regions. It is preferred to have the first heavy chain constant region (CH1), containing the site necessary for light chain binding, present in at least one of the fusions. DNAs encoding the immunoglobulin heavy chain fusions and, if desired, the immunoglobulin light chain, are inserted into separate expression vectors, and are cotransfected into a suitable host organism. This provides for great flexibility in adjusting the mutual proportions of the three polypeptide fragments in embodiments when unequal ratios of the three polypeptide chains used in the construction provide the optimum yields. It is, however, possible to insert the coding sequences for two or all three polypeptide chains in one expression vector when the expression of at least two polypeptide chains in equal ratios results in high yields or when the ratios are of no particular significance.

In one approach, the bispecific antibodies are composed of a hybrid immunoglobulin heavy chain with a first binding specificity in one arm, and a hybrid immunoglobulin heavy chain-light chain pair (providing a second binding specificity) in the other arm. This asymmetric structure, with an immunoglobulin light chain in only one half of the bispecific molecule, facilitates the separation of the desired bispecific compound from unwanted immunoglobulin chain combinations. This approach is described in PCT Publication No. WO 94/04690, published Mar. 3, 1994.

Heteroconjugate antibodies, comprising two covalently joined antibodies, are also within the scope of the invention. Such antibodies have been used to target immune system cells to unwanted cells (U.S. Pat. No. 4,676,980), and for treatment of HIV infection (PCT application publication Nos. WO 91/00360 and WO 92/200373; and EP 03089). Heteroconjugate antibodies may be made using any convenient cross-linking methods. Suitable cross-linking agents and techniques are well known in the art, and are described in U.S. Pat. No. 4,676,980.

Chimeric or hybrid antibodies also may be prepared in vitro using known methods of synthetic protein chemistry, including those involving cross-linking agents. For example, immunotoxins may be constructed using a disulfide exchange reaction or by forming a thioether bond. Examples of suitable reagents for this purpose include iminothiolate and methyl-4-mercaptobutyrimidate.

Humanized antibody comprising one or more CDRs of antibody A5 or one or more CDRs derived from antibody A5 can be made using any methods known in the art. For example, four general steps may be used to humanize a monoclonal antibody. These are: (1) determining the nucleotide and predicted amino acid sequence of the starting antibody light and heavy variable domains (2) designing the humanized antibody, i.e., deciding which antibody framework region to use during the humanizing process (3) the actual humanizing methodologies/techniques and (4) the transfection and expression of the humanized antibody. See, for example, U.S. Pat. Nos. 4,816,567; 5,807,715; 5,866,692; 6,331,415; 5,530,101; 5,693,761; 5,693,762; 5,585,089; 6,180,370; 5,225,539; 6,548,640.

In the recombinant humanized antibodies, the Fc portion can be modified to avoid interaction with Fcγ receptor and the complement immune system. This type of modification was designed by Dr. Mike Clark from the Department of Pathology at Cambridge University, and techniques for preparation of such antibodies are described in PCT Publication No. WO 99/58572, published Nov. 18, 1999.

For example, the constant region may be engineered to more resemble human constant regions to avoid immune response if the antibody is used in clinical trials and treatments in humans. See, for example, U.S. Pat. Nos. 5,997,867 and 5,866,692.

The invention encompasses modifications to antibodies (such as antibody A5) or polypeptides described herein, including functionally equivalent antibodies which do not significantly affect their properties and variants which have enhanced or decreased activity. Modification of polypeptides is routine practice in the art and need not be described in detail herein. Modification of polypeptides is exemplified in the Examples. Examples of modified polypeptides include polypeptides with conservative substitutions of amino acid residues, one or more deletions or additions of amino acids which do not significantly deleteriously change the functional activity, or use of chemical analogs.

Amino acid sequence insertions or additions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue or the antibody fused to an epitope tag. Other insertional variants of the antibody molecule include the fusion to the N- or C-terminus of the antibody of an enzyme or a polypeptide which increases the serum half-life of the antibody.

Substitution variants have at least one amino acid residue in the antibody molecule removed and a different residue inserted in its place. The sites of greatest interest for substitutional mutagenesis include the hypervariable regions, but FR alterations are also contemplated. Conservative substitutions are shown in Table 1 under the heading of "conservative substitutions". If such substitutions result in a change in biological activity, then more substantial changes, denominated "exemplary substitutions" in Table 1, or as further described below in reference to amino acid classes, may be introduced and the products screened.

TABLE 1

Amino Acid Substitutions

| Original Residue | Conservative Substitutions | Exemplary Substitutions |
|---|---|---|
| Ala (A) | Val | Val; Leu; Ile |
| Arg (R) | Lys | Lys; Gln; Asn |
| Asn (N) | Gln | Gln; His; Asp, Lys; Arg |
| Asp (D) | Glu | Glu; Asn |
| Cys (C) | Ser | Ser; Ala |
| Gln (Q) | Asn | Asn; Glu |
| Glu (E) | Asp | Asp; Gln |
| Gly (G) | Ala | Ala |
| His (H) | Arg | Asn; Gln; Lys; Arg |
| Ile (I) | Leu | Leu; Val; Met; Ala; Phe; Norleucine |
| Leu (L) | Ile | Norleucine; Ile; Val; Met; Ala; Phe |
| Lys (K) | Arg | Arg; Gln; Asn |
| Met (M) | Lea | Leu; Phe; Ile |
| Phe (F) | Tyr | Leu; Val; Ile; Ala; Tyr |
| Pro (P) | Ala | Ala |
| Ser (S) | Thr | Thr |
| Thr (T) | Ser | Ser |
| Trp (W) | Tyr | Tyr; Phe |
| Tyr (Y) | Phe | Trp; Phe; Thr; Ser |
| Val (V) | Leu | Ile; Leu; Met; Phe; Ala; Norleucine |

Substantial modifications in the biological properties of the antibody are accomplished by selecting substitutions that differ significantly in their effect on maintaining (a) the structure of the polypeptide backbone in the area of the substitution, for example, as a sheet or helical conformation, (b) the charge or hydrophobicity of the molecule at the target site, or (c) the bulk of the side chain. Naturally occurring residues are divided into groups based on common side-chain properties:

(1) Hydrophobic: Norleucine, Met, Ala, Val, Leu, Ile;
(2) Neutral hydrophilic: Cys, Ser, Thr;
(3) Acidic: Asp, Glu;
(4) Basic: Asn, Gln, His, Lys, Arg;
(5) Residues that influence chain orientation: Gly, Pro; and
(6) Aromatic: Trp, Tyr, Phe.

Non-conservative substitutions are made by exchanging a member of one of these classes for another class.

Any cysteine residue not involved in maintaining the proper conformation of the antibody also may be substituted, generally with serine, to improve the oxidative stability of the molecule and prevent aberrant cross-linking. Conversely, cysteine bond(s) may be added to the antibody to improve its stability, particularly where the antibody is an antibody fragment such as an Fv fragment.

Amino acid modifications can range from changing or modifying one or more amino acids to complete redesign of a region, such as the variable region. Changes in the variable region can alter binding affinity and/or specificity. In some embodiments, no more than one to five conservative amino acid substitutions are made within a CDR domain. In other embodiments, no more than one to three conservative amino acid substitutions are made within a CDR3 domain. In still other embodiments, the CDR domain is CDRH3 and/or CDR L3.

Modifications also include glycosylated and nonglycosylated polypeptides, as well as polypeptides with other post-translational modifications, such as, for example, glycosylation with different sugars, acetylation, and phosphorylation. Antibodies are glycosylated at conserved positions in their constant regions (Jefferis and Lund, 1997, *Chem. Immunol.* 65:111-128; Wright and Morrison, 1997, *TibTECH* 15:26-32). The oligosaccharide side chains of the immunoglobulins affect the protein's function (Boyd et al., 1996, *Mol. Immunol.* 32:1311-1318; Wittwe and Howard, 1990, *Biochem.* 29:4175-4180) and the intramolecular interaction between portions of the glycoprotein, which can affect the conformation and presented three-dimensional surface of the glycoprotein (Hefferis and Lund, supra; Wyss and Wagner, 1996, *Current Opin. Biotech.* 7:409-416). Oligosaccharides may also serve to target a given glycoprotein to certain molecules based upon specific recognition structures. Glycosylation of antibodies has also been reported to affect antibody-dependent cellular cytotoxicity (ADCC). In particular, CHO cells with tetracycline-regulated expression of β (1,4)-N-acetyl-glucosaminyltransferase III (GnTIII), a glycosyltransferase catalyzing formation of bisecting GlcNAc, was reported to have improved ADCC activity (Umana et al., 1999, *Nature Biotech.* 17:176-180).

Glycosylation of antibodies is typically either N-linked or O-linked. N-linked refers to the attachment of the carbohydrate moiety to the side chain of an asparagine residue. The tripeptide sequences asparagine-X-serine, asparagine-X-threonine, and asparagine-X-cysteine, where X is any amino acid except proline, are the recognition sequences for enzymatic attachment of the carbohydrate moiety to the asparagine side chain. Thus, the presence of either of these tripeptide sequences in a polypeptide creates a potential glycosylation site. O-linked glycosylation refers to the attachment of one of the sugars N-acetylgalactosamine, galactose, or xylose to a hydroxyamino acid, most commonly serine or threonine, although 5-hydroxyproline or 5-hydroxylysine may also be used.

Addition of glycosylation sites to the antibody is conveniently accomplished by altering the amino acid sequence such that it contains one or more of the above-described tripeptide sequences (for N-linked glycosylation sites). The alteration may also be made by the addition of, or substitution by, one or more serine or threonine residues to the sequence of the original antibody (for O-linked glycosylation sites).

The glycosylation pattern of antibodies may also be altered without altering the underlying nucleotide sequence. Glycosylation largely depends on the host cell used to express the antibody. Since the cell type used for expression of recombinant glycoproteins, e.g. antibodies, as potential therapeutics is rarely the native cell, variations in the glycosylation pattern of the antibodies can be expected (see, e.g. Hse et al., 1997, *J. Biol. Chem.* 272:9062-9070).

In addition to the choice of host cells, factors that affect glycosylation during recombinant production of antibodies include growth mode, media formulation, culture density, oxygenation, pH, purification schemes and the like. Various methods have been proposed to alter the glycosylation pattern achieved in a particular host organism including introducing or overexpressing certain enzymes involved in oligosaccharide production (U.S. Pat. Nos. 5,047,335; 5,510,261 and 5,278,299). Glycosylation, or certain types of glycosylation, can be enzymatically removed from the glycoprotein, for example using endoglycosidase H (Endo H). In addition, the recombinant host cell can be genetically engineered to be defective in processing certain types of polysaccharides. These and similar techniques are well known in the art.

Other methods of modification include using coupling techniques known in the art, including, but not limited to, enzymatic means, oxidative substitution and chelation. Modifications can be used, for example, for attachment of labels for immunoassay. Modified polypeptides (such as A5) are made using established procedures in the art and can be screened using standard assays known in the art, some of which are described below and in the Examples.

Other antibody modifications include antibodies that have been modified as described in PCT Publication No. WO 99/58572, published Nov. 18, 1999. These antibodies comprise, in addition to a binding domain directed at the target molecule, an effector domain having an amino acid sequence substantially homologous to all or part of a constant domain of a human immunoglobulin heavy chain. These antibodies are capable of binding the target molecule without triggering significant complement dependent lysis, or cell-mediated destruction of the target. In some embodiments, the effector domain is capable of specifically binding FcRn and/or FcγRIIb. These are typically based on chimeric domains derived from two or more human immunoglobulin heavy chain $C_H2$ domains. Antibodies modified in this manner are particularly suitable for use in chronic antibody therapy, to avoid inflammatory and other adverse reactions to conventional antibody therapy.

The invention includes affinity matured embodiments. For example, affinity matured antibodies can be produced by procedures known in the art (Marks et al., 1992, Bio/Technology, 10:779-783; Barbas et al., 1994, Proc Nat. Acad. Sci, USA 91:3809-3813; Schier et al., 1995, Gene, 169:147-155; Yelton et al., 1995, J. Immunol., 155:1994-2004; Jackson et al., 1995, J. Immunol., 154(7):3310-9; Hawkins et al, 1992, J. Mol. Biol., 226:889-896; and WO2004/058184).

The following methods may be used for adjusting the affinity of an antibody and for characterizing a CDR. One way of characterizing a CDR of an antibody and/or altering (such as improving) the binding affinity of a polypeptide, such as an antibody, termed "library scanning mutagenesis". Generally, library scanning mutagenesis works as follows. One or more amino acid positions in the CDR are replaced with two or more (such as 3, 4, 5, 6, 7, 8, 9, 10, 11, 12, 13, 14, 15, 16, 17, 18, 19, or 20) amino acids using art recognized methods. This generates small libraries of clones (in some embodiments, one for every amino acid position that is analyzed), each with a complexity of two or more members (if two or more amino acids are substituted at every position). Generally, the library also includes a clone comprising the native (unsubstituted) amino acid. A small number of clones, e.g., about 20-80 clones (depending on the complexity of the library), from each library are screened for binding affinity to the target polypeptide (or other binding target), and candidates with increased, the same, decreased or no binding are identified. Methods for determining binding affinity are well-known in the art. Binding affinity may be determined using BIAcore surface plasmon resonance analysis, which detects differences in binding affinity of about 2-fold or greater. BIAcore is particularly useful when the starting antibody already binds with a relatively high affinity, for example a $K_D$ of about 10 nM or lower. Screening using BIAcore surface plasmon resonance is described in the Examples, herein.

Binding affinity may be determined using Kinexa Biocensor, scintillation proximity assays, ELISA, ORIGEN immunoassay (IGEN), fluorescence quenching, fluorescence transfer, and/or yeast display. Binding affinity may also be screened using a suitable bioassay.

In some embodiments, every amino acid position in a CDR is replaced (in some embodiments, one at a time) with all 20 natural amino acids using art recognized mutagenesis methods (some of which are described herein). This generates small libraries of clones (in some embodiments, one for every amino acid position that is analyzed), each with a complexity of 20 members (if all 20 amino acids are substituted at every position).

In some embodiments, the library to be screened comprises substitutions in two or more positions, which may be in the same CDR or in two or more CDRs. Thus, the library may comprise substitutions in two or more positions in one CDR. The library may comprise substitution in two or more positions in two or more CDRs. The library may comprise substitution in 3, 4, 5, or more positions, said positions found in two, three, four, five or six CDRs. The substitution may be prepared using low redundancy codons. See, e.g., Table 2 of Balint et al., (1993) Gene 137(1):109-18).

The CDR may be CDRH3 and/or CDRL3. The CDR may be one or more of CDRL1, CDRL2, CDRL3, CDRH1, CDRH2, and/or CDRH3. The CDR may be a Kabat CDR, a Chothia CDR, or an extended CDR.

Candidates with improved binding may be sequenced, thereby identifying a CDR substitution mutant which results in improved affinity (also termed an "improved" substitution). Candidates that bind may also be sequenced, thereby identifying a CDR substitution which retains binding. Sequences of non-binders may also be sequenced in order to know which antibody abolish binding.

Multiple rounds of screening may be conducted. For example, candidates (each comprising an amino acid substitution at one or more position of one or more CDR) with improved binding are also useful for the design of a second library containing at least the original and substituted amino acid at each improved CDR position (i.e., amino acid position in the CDR at which a substitution mutant showed improved binding). Preparation, and screening or selection of this library is discussed further below.

Library scanning mutagenesis also provides a means for characterizing a CDR, in so far as the frequency of clones with improved binding, the same binding, decreased binding or no binding also provide information relating to the importance of each amino acid position for the stability of the antibody-antigen complex. For example, if a position of the CDR retains binding when changed to all 20 amino acids, that position is identified as a position that is unlikely to be required for antigen binding. Conversely, if a position of CDR retains binding in only a small percentage of substitutions, that position is identified as a position that is important to CDR function. Thus, the library scanning mutagenesis methods generate information regarding positions in the CDRs that can be changed to many different amino acid (including all 20 amino acids), and positions in the CDRs which cannot be changed or which can only be changed to a few amino acids.

Candidates with improved affinity may be combined in a second library, which includes the improved amino acid, the original amino acid at that position, and may further include additional substitutions at that position, depending on the complexity of the library that is desired, or permitted using the desired screening or selection method. In addition, if desired, adjacent amino acid position can be randomized to at least two or more amino acids. Randomization of adjacent amino acids may permit additional conformational flexibility in the mutant CDR, which may in turn, permit or facilitate the introduction of a larger number of improving mutations. The library may also comprise substitution at positions that did not show improved affinity in the first round of screening.

The second library is screened or selected for library members with improved and/or altered binding affinity using any method known in the art, including screening using BIAcore surface plasmon resonance analysis, and selection using any method known in the art for selection, including phage display, yeast display, and ribosome display.

The invention also encompasses fusion proteins comprising one or more fragments or regions from the antibodies (such as A5) or polypeptides of this invention. In one embodiment, a fusion polypeptide is provided that comprises at least 10 contiguous amino acids of the variable light chain region shown in FIG. 1B and/or at least 10 amino acids of the variable heavy chain region shown in FIG. 1A. In another embodiment, the fusion polypeptide comprises a light chain variable region and/or a heavy chain variable region of A5, as shown in FIGS. 1A and 1B. In another embodiment, the fusion polypeptide comprises one or more CDR(s) of A5. In still other embodiments, the fusion polypeptide comprises CDR H3 and/or CDR L3 of antibody A5. In another embodiment, the fusion polypeptide comprises any one or more of: amino acid residue R33 and/or I34 of CDR H1; A56 of CDR H2; T105 and/or R106 of CDR H3; I29, L37 and/or A38 of CDR L1; R58 of CDR L2; and/or T97 of CDR L3. For purposes of this invention, an A5 fusion protein contains one or more A5 antibodies and another amino acid sequence to which it is not attached in the native molecule, for example, a heterologous sequence or a homologous sequence from another region. Exemplary heterologous sequences include, but are not limited to a "tag" such as a FLAG tag or a 6His tag. Tags are well known in the art.

A fusion polypeptide can be created by methods known in the art, for example, synthetically or recombinantly. Typically, the A5 fusion proteins of this invention are made by preparing an expressing a polynucleotide encoding them using recombinant methods described herein, although they may also be prepared by other means known in the art, including, for example, chemical synthesis.

This invention also provides compositions comprising antibodies (such as A5) or polypeptides conjugated (for example, linked) to an agent that facilitate coupling to a solid support (such as biotin or avidin). For simplicity, reference will be made generally to A5 or antibodies with the understanding that these methods apply to any of the trkC binding embodiments described herein. Conjugation generally refers to linking these components as described herein. The linking (which is generally fixing these components in proximate association at least for administration) can be achieved in any number of ways. For example, a direct reaction between an agent and an antibody is possible when each possesses a substituent capable of reacting with the other. For example, a nucleophilic group, such as an amino or sulfhydryl group, on one may be capable of reacting with a carbonyl-containing group, such as an anhydride or an acid halide, or with an alkyl group containing a good leaving group (e.g., a halide) on the other.

An antibody or polypeptide of this invention may be linked to a labeling agent (alternatively termed "label") such as a fluorescent molecule, a radioactive molecule or any others labels known in the art. Labels are known in the art which generally provide (either directly or indirectly) a signal. Accordingly, the invention includes labeled antibodies and polypeptides.

The ability of the antibodies and polypeptides of this invention, such as binding trkC, activating trkC biological activity; and/or enhancing trkC-induced survival of E12 rat trigeminal neurons, may be tested using methods known in the art, some of which are described in the Examples.

The invention also provides compositions (including pharmaceutical compositions) and kits comprising antibody A5, and, as this disclosure makes clear, any or all of the antibodies and/or polypeptides described herein.

Polynucleotides, Vectors and Host Cells

The invention also provides isolated polynucleotides encoding the antibodies and polypeptides of the invention (including an antibody comprising the polypeptide sequences of the light chain and heavy chain variable regions shown in FIGS. 1A and 1B), and vectors and host cells comprising the polynucleotide.

Accordingly, the invention provides polynucleotides (or compositions, including pharmaceutical compositions), comprising polynucleotides encoding any of the following: (a) antibody A5; (b) a fragment or a region of the antibody A5; (c) a light chain of the antibody A5 as shown in FIG. 1B; (d) a heavy chain of the antibody A5 as shown in FIG. 1A; (e) one or more variable region(s) from a light chain and/or a heavy chain of the antibody A5; (f) one or more CDR(s) (one, two, three, four, five or six CDRs) of antibody A5 shown in FIGS. 1A and 1B; (g) CDR H3 from the heavy chain of antibody A5 shown in FIG. 1A; (h) CDR L3 from the light chain of antibody A5 shown in FIG. 1B; (i) three CDRs from the light chain of antibody A5 shown in FIG. 1B; (j) three CDRs from the heavy chain of antibody A5 shown in FIG. 1A; (k) three CDRs from the light chain and three CDRs from the heavy chain, of antibody A5 shown in FIGS. 1A and 1B; or (l) an antibody comprising any of (b) to (k). In some embodiments, the polynucleotide comprises either or both of the polynucleotide(s) shown in SEQ ID NO: 10 and 12. In other embodiments, the polynucleotide comprises either or both of the polynucleotide(s) shown in SEQ ID NO:11 and 13. In other embodiments, the polynucleotide comprises either or both of the polynucleotide(s) shown in SEQ ID NO: 10 and 13. In other embodiments, the polynucleotide comprises either or both of the polynucleotide(s) shown in SEQ ID NOS:11 and 12.

In another aspect, the invention is an isolated polynucleotide that encodes for an A5 light chain with a deposit number of ATCC No. PTA-5682. In another aspect, the invention is an isolated polynucleotide that encodes for an A5 heavy chain with a deposit number of ATCC No. PTA-5683. In yet another aspect, the invention is an isolated polynucleotide comprising (a) a variable region encoded in the polynucleotide with a deposit number of ATCC No. PTA-5682 and (b) a variable region encoded in the polynucleotide with a deposit number of ATCC No. PTA-5683. In another aspect, the invention is an isolated polynucleotide comprising (a) one or more CDR encoded in the polynucleotide with a deposit number of ATCC No. PTA-5682; and/or (b) one or more CDR encoded in the polynucleotide with a deposit number of ATCC No. PTA-5683.

In another aspect, the invention provides polynucleotides encoding any of the antibodies (including antibody fragments) and polypeptides described herein. Polynucleotides can be made by procedures known in the art.

In another aspect, the invention provides compositions (such as a pharmaceutical compositions) comprising any of the polynucleotides of the invention. In some embodiments, the composition comprises an expression vector comprising a polynucleotide encoding the A5 antibody as described herein. In other embodiment, the composition comprises an expression vector comprising a polynucleotide encoding any of the antibodies or polypeptides described herein. In still other embodiments, the composition comprises either or both of the polynucleotide(s) shown in SEQ ID NOS:10 and 12. In other embodiments, the composition comprises either or both of the polynucleotide(s) shown in SEQ ID NOS:11 and 13. In other embodiments, the composition comprises either or both of the polynucleotide(s) shown in SEQ ID NOS:10 and 13. In other embodiments, the composition comprises either or both of the polynucleotide(s) shown in SEQ ID NOS:11 and 12. Expression vectors, and administration of polynucleotide compositions are further described herein.

In another aspect, the invention provides a method of making any of the polynucleotides described herein.

Polynucleotides complementary to any such sequences are also encompassed by the present invention. Polynucleotides may be single-stranded (coding or antisense) or double-stranded, and may be DNA (genomic, cDNA or synthetic) or RNA molecules. RNA molecules include HnRNA molecules, which contain introns and correspond to a DNA molecule in a one-to-one manner, and mRNA molecules, which do not contain introns. Additional coding or non-coding sequences may, but need not, be present within a polynucleotide of the present invention, and a polynucleotide may, but need not, be linked to other molecules and/or support materials.

Polynucleotides may comprise a native sequence (i.e., an endogenous sequence that encodes an antibody or a portion thereof) or may comprise a variant of such a sequence. Polynucleotide variants contain one or more substitutions, additions, deletions and/or insertions such that the immunoreactivity or efficacy of the encoded polypeptide is not diminished, relative to a native immunoreactive molecule. The effect on the immunoreactivity of the encoded polypeptide may generally be assessed as described herein. Variants preferably exhibit at least about 70% identity, more preferably at least about 80% identity and most preferably at least about 90% identity to a polynucleotide sequence that encodes a native antibody or a portion thereof.

Two polynucleotide or polypeptide sequences are said to be "identical" if the sequence of nucleotides or amino acids in the two sequences is the same when aligned for maximum correspondence as described below. Comparisons between two sequences are typically performed by comparing the sequences over a comparison window to identify and compare local regions of sequence similarity. A "comparison window" as used herein, refers to a segment of at least about 20 contiguous positions, usually 30 to about 75, 40 to about 50, in which a sequence may be compared to a reference sequence of the same number of contiguous positions after the two sequences are optimally aligned.

Optimal alignment of sequences for comparison may be conducted using the Megalign program in the Lasergene suite of bioinformatics software (DNASTAR, Inc., Madison, Wis.), using default parameters. This program embodies several alignment schemes described in the following references: Dayhoff, M. O. (1978) A model of evolutionary change in proteins—Matrices for detecting distant relationships. In Dayhoff, M. O. (ed.) *Atlas of Protein Sequence and Structure*, National Biomedical Research Foundation, Washington D.C. Vol. 5, Suppl. 3, pp. 345-358; Hein J., 1990, *Unified Approach to Alignment and Phylogenes* pp. 626-645 *Methods in Enzymology* vol. 183, Academic Press, Inc., San Diego, Calif.; Higgins, D. G. and Sharp, P. M., 1989, *CABIOS* 5:151-153; Myers, E. W. and Muller W., 1988, *CABIOS* 4:11-17; Robinson, E. D., 1971, *Comb. Theor.* 11:105; Santou, N., Nes, M., 1987, *Mol. Biol. Evol.* 4:406-425; Sneath, P. H. A. and Sokal, R. R., 1973, *Numerical Taxonomy the Principles and Practice of Numerical Taxonomy*, Freeman Press, San Francisco, Calif.; Wilbur, W. J. and Lipman, D. J., 1983, *Proc. Natl. Acad. Sci.* USA 80:726-730.

Preferably, the "percentage of sequence identity" is determined by comparing two optimally aligned sequences over a window of comparison of at least 20 positions, wherein the portion of the polynucleotide or polypeptide sequence in the comparison window may comprise additions or deletions (i.e. gaps) of 20 percent or less, usually 5 to 15 percent, or 10 to 12 percent, as compared to the reference sequences (which does not comprise additions or deletions) for optimal alignment of the two sequences. The percentage is calculated by determining the number of positions at which the identical nucleic acid bases or amino acid residue occurs in both sequences to yield the number of matched positions, dividing the number of matched positions by the total number of positions in the reference sequence (i.e. the window size) and multiplying the results by 100 to yield the percentage of sequence identity.

Variants may also, or alternatively, be substantially homologous to a native gene, or a portion or complement thereof. Such polynucleotide variants are capable of hybridizing under moderately stringent conditions to a naturally occurring DNA sequence encoding a native antibody (or a complementary sequence).

Suitable "moderately stringent conditions" include pre-washing in a solution of 5×SSC, 0.5% SDS, 1.0 mM EDTA (pH 8.0); hybridizing at 50° C.-65° C., 5×SSC, overnight; followed by washing twice at 65° C. or 42° C. for 20 minutes with each of 2×, 0.5× and 0.2×SSC containing 0.1% SDS.

As used herein, "highly stringent conditions" or "high stringency conditions" are those that: (1) employ low ionic strength and high temperature for washing, for example 0.015 M sodium chloride/0.0015 M sodium citrate/0.1% sodium dodecyl sulfate at 50° C.; (2) employ during hybridization a denaturing agent, such as formamide, for example, 50% (v/v) formamide with 0.1% bovine serum albumin/0.1% Ficoll/0.1% polyvinylpyrrolidone/50 mM sodium phosphate buffer at pH 6.5 with 750 mM sodium chloride, 75 mM sodium citrate at 42° C.; or (3) employ 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% SDS, and 10% dextran sulfate at 42° C., with washes at 42° C. in 0.2×SSC (sodium chloride/sodium citrate) and 50% formamide at 55° C., followed by a high-stringency wash consisting of 0.1×SSC containing EDTA at 55° C. or 68° C. The skilled artisan will recognize how to adjust the temperature, ionic strength, etc. as necessary to accommodate factors such as probe length and the like.

It will be appreciated by those of ordinary skill in the art that, as a result of the degeneracy of the genetic code, there are many nucleotide sequences that encode a polypeptide as described herein. Some of these polynucleotides bear minimal homology to the nucleotide sequence of any native gene. Nonetheless, polynucleotides that vary due to differences in codon usage are specifically contemplated by the present invention. Further, alleles of the genes comprising the polynucleotide sequences provided herein are within the scope of the present invention. Alleles are endogenous genes that are altered as a result of one or more mutations, such as deletions, additions and/or substitutions of nucleotides. The resulting mRNA and protein may, but need not, have an altered structure or function. Alleles may be identified using standard techniques (such as hybridization, amplification and/or database sequence comparison).

The polynucleotides of this invention can be obtained using chemical synthesis, recombinant methods, or PCR. Methods of chemical polynucleotide synthesis are well known in the art and need not be described in detail herein. One of skill in the art can use the sequences provided herein and a commercial DNA synthesizer to produce a desired DNA sequence.

For preparing polynucleotides using recombinant methods, a polynucleotide comprising a desired sequence can be inserted into a suitable vector, and the vector in turn can be introduced into a suitable host cell for replication and amplification, as further discussed herein. Polynucleotides may be inserted into host cells by any means known in the art. Cells are transformed by introducing an exogenous polynucleotide by direct uptake, endocytosis, transfection, F-mating or electroporation. Once introduced, the exogenous polynucleotide can be maintained within the cell as a non-integrated vector (such as a plasmid) or integrated into the host cell genome. The polynucleotide so amplified can be isolated from the host cell by methods well known within the art. See, e.g., Sambrook et al. (1989).

Alternatively, PCR allows reproduction of DNA sequences. PCR technology is well known in the art and is described in U.S. Pat. Nos. 4,683,195, 4,800,159, 4,754,065 and 4,683,202, as well as PCR: *The Polymerase Chain Reaction*, Mullis et al. eds., Birkauswer Press, Boston (1994).

RNA can be obtained by using the isolated DNA in an appropriate vector and inserting it into a suitable host cell. When the cell replicates and the DNA is transcribed into RNA, the RNA can then be isolated using methods well known to those of skill in the art, as set forth in Sambrook et al., (1989), for example.

Suitable cloning vectors may be constructed according to standard techniques, or may be selected from a large number of cloning vectors available in the art. While the cloning vector selected may vary according to the host cell intended to be used, useful cloning vectors will generally have the ability to self-replicate, may possess a single target for a particular restriction endonuclease, and/or may carry genes for a marker that can be used in selecting clones containing the vector. Suitable examples include plasmids and bacterial viruses, e.g., pUC18, pUC19, Bluescript (e.g., pBS SK+) and its derivatives, mp18, mp19, pBR322, pMB9, ColE1, pCR1, RP4, phage DNAs, and shuttle vectors such as pSA3 and pAT28. These and many other cloning vectors are available from commercial vendors such as BioRad, Stratagene, and Invitrogen.

Expression vectors generally are replicable polynucleotide constructs that contain a polynucleotide according to the invention. It is implied that an expression vector must be replicable in the host cells either as episomes or as an integral part of the chromosomal DNA. Suitable expression vectors include but are not limited to plasmids, viral vectors, including adenoviruses, adeno-associated viruses, retroviruses, cosmids, and expression vector(s) disclosed in PCT Publication No. WO 87/04462. Vector components may generally include, but are not limited to, one or more of the following: a signal sequence; an origin of replication; one or more marker genes; suitable transcriptional controlling elements (such as promoters, enhancers and terminator). For expression (i.e., translation), one or more translational controlling elements are also usually required, such as ribosome binding sites, translation initiation sites, and stop codons.

The vectors containing the polynucleotides of interest can be introduced into the host cell by any of a number of appropriate means, including electroporation, transfection employing calcium chloride, rubidium chloride, calcium phosphate, DEAE-dextran, or other substances; microprojectile bombardment; lipofection; and infection (e.g., where the vector is an infectious agent such as vaccinia virus). The choice of introducing vectors or polynucleotides will often depend on features of the host cell.

The invention also provides host cells comprising any of the polynucleotides or polypeptides or antibodies described herein. Any host cells capable of expressing (including overexpressing) heterologous DNAs can be used for the purpose of isolating the genes encoding the antibody, polypeptide or protein of interest. Non-limiting examples of mammalian host cells include but not limited to COS, HeLa, and CHO cells. See also PCT Publication No. WO 87/04462. Suitable non-mammalian host cells include prokaryotes (such as *E. coli* or *B. subtilis*) and yeast (such as *S. cerevisae, S. pombe*; or *K. lactis*). Preferably, the host cells express the cDNAs at a level of about 5 fold higher, more preferably 10 fold higher, even more preferably 20 fold higher than that of the corresponding endogenous antibody or protein of interest, if present, in the host cells. Screening the host cells for production of a polypeptide with specific binding to trkC is effected by an immunoassay or FACS. A cell overexpressing the antibody or protein of interest can be identified.

Methods Using Antibodies or Polypeptides

Antibody A5 which binds trkC may be used to identify or detect the presence or absence of trkC or fragment of trkC. For simplicity, reference will be made generally to A5 or antibodies with the understanding that these methods apply to any of the trkC binding embodiments (such as polypeptides) described herein. Detection generally involves contacting a biological sample with an antibody described herein that binds to trkC and the formation of a complex between trkC and an antibody (e.g., A5) which binds specifically to trkc. The formation of such a complex can be in vitro or in vivo. The term "detection" as used herein includes qualitative and/ or quantitative detection (measuring levels) with or without reference to a control.

Any of a variety of known methods can be used for detection, including, but not limited to, immunoassay, using antibody that binds the polypeptide, e.g. by enzyme-linked immunosorbent assay (ELISA), radioimmunoassay (RIA) and the like; and functional assay for the encoded polypeptide, e.g. binding activity or enzymatic assay. In some embodiments, the antibody is detectably labeled. Other embodiments are known in the art and described herein.

Diagnostic Uses of the Antibodies

Antibodies and polypeptides of the invention can be used in the detection, diagnosis and monitoring of a disease, condition, or disorder associated with altered or aberrant trkC expression (in some embodiments, increased or decreased trkC expression (relative to a normal sample), and/or inappropriate expression, such as presence of expression in tissue(s) and/or cell(s) that normally lack trkC expression, or absence of trkC expression in tissue(s) or cell(s) that normally possess trkC expression). For example, trkC expressing tumors are known in the art, and include primitive neuroectodermal tumor (PNET), Ewings sarcoma cells, pancreatic cancer and medullary thyroid cancers. The antibodies and polypeptides of the invention are further useful for detection of trkC expression, for example, in a disease associated with altered or aberrant sensitivity or responsiveness to trkC. Thus, in some embodiments, the invention provides methods comprises contacting a specimen (sample) of an individual suspected of having altered or aberrant trkC expression with an antibody or polypeptide of the invention and determining whether the level of trkC differs from that of a control or comparison specimen.

In other embodiments, the invention provides methods comprises contacting a specimen (sample) of an individual and determining level of trkC expression. In some embodiments, the individual is suspected of having a disease, disorder featuring or associated with an altered or aberrant sensitivity or responsiveness to trkC expression.

For diagnostic applications, the antibody may be labeled with a detectable moiety including but not limited to radioisotopes, fluorescent labels, and various enzyme-substrate labels. Methods of conjugating labels to an antibody are known in the art. In other embodiment of the invention, antibodies of the invention need not be labeled, and the presence thereof can be detected using a labeled antibody which binds to the antibodies of the invention.

The antibodies of the present invention may be employed in any known assay method, such competitive binding assays, direct and indirect sandwich assays, and immunoprecipitation assays. Zola, *Monoclonal Antibodies: A Manual of Techniques*, pp. 147-158 (CRC Press, Inc. 1987).

The antibodies may also be used for in vivo diagnostic assays, such as in vivo imaging. Generally, the antibody is labeled with a radionuclide (such as $^{111}$In, $^{99}$Tc, $^{14}$C, $^{131}$I, $^{125}$I, or $^{3}$H) so that the cells or tissue of interest can be localized using immunoscintiography.

The antibody may also be used as staining reagent in pathology, following techniques well known in the art.

Methods of Using Antibodies or Polypeptides (Such as A5) for Therapeutic Purposes Antibody A5 is useful for activating the biological activity of trkC. This agonist activity is believed to be useful in the treatment of pathological conditions associated with a sensory neuropathy or neurodegenerative disease, or repairing a damaged nerve cell. The neuropathy may, for example, be a peripheral neuropathy, including, without limitation, large fiber sensory neuropathies. In some embodiments, an individual with sensory neuropathy, such as large fiber sensory neuropathy, such as taxol-induced sensory neuropathy, cisplatin-induced sensory neuropathy, or pyridoxine-induced neuropathy, is given treatment with A5 or other antibodies or polypeptides described herein. Generally, in these embodiments an effective amount is administered to an individual.

For simplicity, reference will be made generally to A5 or antibody with the understanding that these methods apply to any of the trkC binding embodiments described herein.

Various formulations of A5 or fragments of A5 (e.g., Fab, Fab', F(ab')$_2$, Fv, Fc, etc.), such as single chain (ScFv), mutants thereof, fusion proteins comprising an antibody portion, and any other modified configuration of A5 that comprises an antigen trkC recognition site of the required specificity, may be used for administration. In some embodiments, A5 antibodies or various formulations of A5 thereof may be administered neat. In other embodiments, A5 or various formulations of A5 (including any composition embodiment described herein) thereof and a pharmaceutically acceptable excipient are administered, and may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in Remington, *The Science and Practice of Pharmacy* 20th Ed. Mack Publishing (2000).

In some embodiments, these agents are formulated for administration by injection (e.g., intraperitoneally, intrathecally, intravenously, subcutaneously, intramuscularly, etc.), although other forms of administration (e.g., oral, mucosal, via inhalation, sublingually, etc) can be also used. Accordingly, A5 antibody and equivalents thereof are preferably combined with pharmaceutically acceptable vehicles such as saline, Ringer's solution, dextrose solution, and the like. The particular dosage regimen, i.e., dose, timing and repetition, will depend on the particular individual and that individual's medical history. Generally, a dose of less than about 1 ug/kg body weigh, at least about 1 ug/kg body weight; at least about 2 ug/kg body weight, at least about 5 ug/kg body weight, at least about 10 ug/kg body weight, at least about 20 ug/kg body weight, at least about 50 ug/kg body weight, at least about 100 ug/kg body weight, at least about 200 ug/kg body weight, at least about 500 ug/kg body weight, at least about 1 mg/kg, body weight, at least about 2 mg/kg body weight, at least about 5 mg/kg body weight, at least about 10 mg/kg body weight, at least about 30 mg/kg body weight, or more (such as about 50 mg/kg, about 100 mg/kg, about 200 mg/kg or about 500 mg/kg) is administered. For repeated administrations over several days or longer, depending on the condition, the treatment is sustained until a desired suppression of disease symptoms occurs. An exemplary dosing regimen comprises administering an initial dose of about 2 mg/kg, followed by a weekly maintenance dose of about 1 mg/kg of the anti-trkC antibody, or followed by a maintenance dose of about 1 mg/kg every other week. However, other dosage regimens may be useful, depending on the pattern of pharmacokinetic decay that the practitioner wishes to achieve. Empirical considerations, such as the half-life, generally will contribute to determination of the dosage. The progress of this therapy is easily monitored by conventional techniques and assays.

In some individuals, more than one dose may be required. Frequency of administration may be determined and adjusted over the course of therapy. For example, frequency of administration may be determined or adjusted based on the type and severity of the symptoms to be treated, whether the agent is administered for preventive or therapeutic purposes, previous therapy, the patient's clinical history and response to the agent, and the discretion of the attending physician. Typically the clinician will administer an agonist anti-TrkC antibody (such as A5), until a dosage is reached that achieves the desired result. In some cases, sustained continuous release formulations of A5 antibodies may be appropriate. Various formulations and devices for achieving sustained release are known in the art.

In one embodiment, dosages for A5 antibodies (or polypeptides) may be determined empirically in individuals who have been given one or more administration(s). Individuals are given incremental dosages of A5. To assess efficacy of A5 or other equivalent antibody, markers of the disease symptoms (such as pain) can be monitored.

Administration of an antibody (such as A5) or polypeptide in accordance with the method in the present invention can be continuous or intermittent, depending, for example, upon the recipient's physiological condition, whether the purpose of the administration is therapeutic or prophylactic, and other factors known to skilled practitioners. The administration of an antibody may be essentially continuous over a preselected period of time or may be in a series of spaced dose, e.g., either before, during, or after developing symptoms, before, during, before and after, during and after, or before, during, and after developing symptoms. Administration can be before, during and/or after wound, incision, trauma, surgery, and any other event likely to give rise to symptoms (such as sensory neuropathy, such as taxol-induced sensory neuropathy).

Other formulations include suitable delivery forms known in the art including, but not limited to, carriers such as liposomes. See, for example, Mahato et al. (1997) *Pharm. Res.* 14:853-859. Liposomal preparations include, but are not limited to, cytofectins, multilamellar vesicles and unilamellar vesicles.

In some embodiments, more than one antibody or polypeptide may be present. The antibodies can be monoclonal or polyclonal. Such compositions may contain at least one, at least two, at least three, at least four, at least five different antibodies. A mixture of antibodies, as they are often denoted in the art, may be particularly useful in treating a broader range of population or individuals.

A polynucleotide encoding any of the antibodies or polypeptides of the invention (such as antibody A5) may also be used for delivery and expression of any of the antibodies or polypeptides of the invention (such as antibody A5) in a desired cell. It is apparent that an expression vector can be used to direct expression of an A5 antibody or polypeptide. The expression vector can be administered by any means known in the art, such as intraperitoneally, intravenously, intramuscularly, subcutaneously, intrathecally, intraventricularly, orally, enterally, parenterally, intranasally, dermally, sublingually, or by inhalation. For example, administration of expression vectors includes local or systemic administration, including injection, oral administration, particle gun or catheterized administration, and topical administration. One skilled in the art is familiar with administration of expression vectors to obtain expression of an exogenous protein in vivo. See, e.g., U.S. Pat. Nos. 6,436,908; 6,413,942; and 6,376,471.

Targeted delivery of therapeutic compositions comprising a polynucleotide encoding any of the antibodies or polypeptides of the invention (such as antibody A5) can also be used. Receptor-mediated DNA delivery techniques are described in, for example, Findeis et al., *Trends Biotechnol.* (1993) 11:202; Chiou et al., *Gene Therapeutics: Methods And Applications Of Direct Gene Transfer* (J. A. Wolff, ed.) (1994); Wu et al., *J. Biol. Chem.* (1988) 263:621; Wu et al., *J. Biol. Chem.* (1994) 269:542; Zenke et al., *Proc. Natl. Acad. Sci.* (USA) (1990) 87:3655; Wu et al., *J. Biol. Chem.* (1991) 266:338. Therapeutic compositions containing a polynucleotide are administered in a range of about 100 ng to about 200 mg of DNA for local administration in a gene therapy protocol. Concentration ranges of about 500 ng to about 50 mg, about 1 µg to about 2 mg, about 5 µg to about 500 µg, and about 20 µg to about 100 µg of DNA can also be used during a gene therapy protocol. The therapeutic polynucleotides and polypeptides of the present invention can be delivered using gene delivery vehicles. The gene delivery vehicle can be of viral or non-viral origin (see generally, Jolly, *Cancer Gene Therapy* (1994) 1:51; Kimura, *Human Gene Therapy* (1994) 5:845; Connelly, *Human Gene Therapy* (1995) 1:185; and Kaplitt, *Nature Genetics* (1994) 6:148). Expression of such coding sequences can be induced using endogenous mammalian or heterologous promoters. Expression of the coding sequence can be either constitutive or regulated.

Viral-based vectors for delivery of a desired polynucleotide and expression in a desired cell are well known in the art. Exemplary viral-based vehicles include, but are not limited to, recombinant retroviruses (see, e.g., PCT Publication Nos. WO 90/07936; WO 94/03622; WO 93/25698; WO 93/25234; WO 93/11230; WO 93/10218; WO 91/02805; U.S. Pat. Nos. 5,219,740; 4,777,127; GB Patent No. 2,200,651; and EP Patent No. 0 345 242), alphavirus-based vectors (e.g., Sindbis virus vectors, Semliki forest virus (ATCC VR-67; ATCC VR-1247), Ross River virus (ATCC VR-373; ATCC VR-1246) and Venezuelan equine encephalitis virus (ATCC VR-923; ATCC VR-1250; ATCC VR 1249; ATCC VR-532)), and adeno-associated virus (AAV) vectors (see, e.g., PCT Publication Nos. WO 94/12649, WO 93/03769; WO 93/19191; WO 94/28938; WO 95/11984 and WO 95/00655). Administration of DNA linked to killed adenovirus as described in Curiel, *Hum. Gene Ther.* (1992) 3:147 can also be employed.

Non-viral delivery vehicles and methods can also be employed, including, but not limited to, polycationic condensed DNA linked or unlinked to killed adenovirus alone (see, e.g., Curiel, *Hum. Gene Ther.* (1992) 3:147); ligand-linked DNA (see, e.g., Wu, *J. Biol. Chem.* (1989) 264:16985); eukaryotic cell delivery vehicles cells (see, e.g., U.S. Pat. No. 5,814,482; PCT Publication Nos. WO 95/07994; WO 96/17072; WO 95/30763; and WO 97/42338) and nucleic charge neutralization or fusion with cell membranes. Naked DNA can also be employed. Exemplary naked DNA introduction methods are described in PCT Publication No. WO 90/11092 and U.S. Pat. No. 5,580,859. Liposomes that can act as gene delivery vehicles are described in U.S. Pat. No. 5,422,120; PCT Publication Nos. WO 95/13796; WO 94/23697; WO 91/14445; and EP Patent No. 0 524 968. Additional approaches are described in Philip, *Mol. Cell. Biol.* (1994) 14:2411 and in Woffendin, *Proc. Natl. Acad. Sci.* (1994) 91:1581.

With respect to all methods described herein, reference to agonist anti-trkC antibodies (or polypeptides) also include compositions comprising one or more of these agents. These compositions may further comprise suitable excipients, such as pharmaceutically acceptable excipients including buffers, which are well known in the art. The present invention can be used alone or in combination with other conventional methods of treatment.

Agonist anti-trkC antibody (or polypeptides) may be administered to an individual via any suitable route. Examples of different administration route are described herein.

Administration of an Agonist Anti-trkC Antibody

The agonist anti-trkC antibody (or polypeptides) can be administered to an individual via any suitable route. It should be apparent to a person skilled in the art that the examples described herein are not intended to be limiting but to be illustrative of the techniques available. For simplicity, reference will be made generally to A5 or antibody with the understanding that these methods apply to any of the trkC binding embodiments. Accordingly, in some embodiments, the agonist anti-trkC antibody is administered to a individual in accord with known methods, such as intravenous administration, e.g., as a bolus or by continuous infusion over a period of time, by intramuscular, intraperitoneal, intracerebrospinal, subcutaneous, intra-articular, sublingually, intrasynovial, via insufflation, intrathecal, oral, inhalation or topical routes. Administration can be systemic, e.g., intravenous administration, or localized. Commercially available nebulizers for liquid formulations, including jet nebulizers and ultrasonic nebulizers are useful for administration. Liquid formulations can be directly nebulized and lyophilized powder can be nebulized after reconstitution. Alternatively, agonist anti-trkC antibody can be aerosolized using a fluorocarbon formulation and a metered dose inhaler, or inhaled as a lyophilized and milled powder.

In one embodiment, an agonist anti-trkC antibody is administered via site-specific or targeted local delivery techniques. Examples of site-specific or targeted local delivery techniques include various implantable depot sources of the agonist anti-trkC antibody or local delivery catheters, such as infusion catheters, an indwelling catheter, or a needle catheter, synthetic grafts, adventitial wraps, shunts and stents or other implantable devices, site specific carriers, direct injection, or direct application. See, e.g., PCT Publication No. WO 00/53211 and U.S. Pat. No. 5,981,568.

Various formulations of an agonist anti-trkC antibody may be used for administration. In some embodiments, the agonist anti-trkC antibody may be administered neat. In some embodiments, agonist anti-trkC antibody and a pharmaceutically acceptable excipient may be in various formulations. Pharmaceutically acceptable excipients are known in the art, and are relatively inert substances that facilitate administration of a pharmacologically effective substance. For example, an excipient can give form or consistency, or act as a diluent. Suitable excipients include but are not limited to stabilizing agents, wetting and emulsifying agents, salts for varying osmolarity, encapsulating agents, buffers, and skin penetration enhancers. Excipients as well as formulations for parenteral and nonparenteral drug delivery are set forth in *Remington, The Science and Practice of Pharmacy* 20th Ed. Mack Publishing (2000).

In some embodiments, these agents are formulated for administration by injection (e.g., intraperitoneally, intrathecally, intravenously, subcutaneously, intramuscularly, etc.). Accordingly, these agents can be combined with pharmaceutically acceptable vehicles such as saline, Ringer's solution, dextrose solution, and the like. The particular dosage regimen, i.e., dose, timing and repetition, will depend on the particular individual and that individual's medical history.

An anti-trkC antibody can be administered using any suitable method, including by injection (e.g., intraperitoneally, intrathecally, intravenously, subcutaneously, intramuscularly, etc.). Anti-trkC antibodies can also be administered via inhalation, as described herein. Generally, a dose of less than about 1 ug/kg body weigh, at least about 1 ug/kg body weight; at least about 2 ug/kg body weight, at least about 5 ug/kg body weight, at least about 10 ug/kg body weight, at least about 20 ug/kg body weight, at least about 50 ug/kg body weight, at least about 100 ug/kg body weight, at least about 200 ug/kg body weight, at least about 500 ug/kg body weight, at least about 1 mg/kg, body weight, at least about 2 mg/kg body weight, at least about 5 mg/kg body weight, at least about 10 mg/kg body weight, at least about 30 mg/kg body weight, or more (such as about 50 mg/kg, about 100 mg/kg, about 200 mg/kg or about 500 mg/kg) is administered. For repeated administrations over several days or longer, depending on the condition, the treatment is sustained until a desired suppression of symptoms occurs or until sufficient therapeutic levels are achieved to reduce symptoms, e.g. neuropathy. An exemplary dosing regimen comprises administering an initial dose of about 2 mg/kg, followed by a weekly maintenance dose of about 1 mg/kg of the anti-trkC antibody, or followed by a maintenance dose of about 1 mg/kg every other week. However, other dosage regimens may be useful, depending on the pattern of pharmacokinetic decay that the practitioner wishes to achieve. For example, in some embodiments, dosing from one-four times a week is contemplated. The progress of this therapy is easily monitored by conventional techniques and assays. The dosing regimen (including the trkC agonist(s) used) can vary over time.

For the purpose of the present invention, the appropriate dosage of an agonist anti-trkC antibody will depend on the agonist anti-trkC antibody (or compositions thereof) employed, the type and severity of the symptoms to be treated, whether the agent is administered for preventive or therapeutic purposes, previous therapy, the patient's clinical history and response to the agent, and the discretion of the attending physician. Typically the clinician will administer an agonist anti-trkC antibody, until a dosage is reached that achieves the desired result. Dose and/or frequency can vary over course of treatment.

Empirical considerations, such as the half-life, generally will contribute to the determination of the dosage. For example, antibodies that are compatible with the human immune system, such as humanized antibodies or fully human antibodies, may be used to prolong half-life of the antibody and to prevent the antibody being attacked by the host's immune system. Frequency of administration may be determined and adjusted over the course of therapy, and is generally, but not necessarily, based on treatment and/or suppression and/or amelioration and/or delay of symptoms (e.g. neuropathy). Alternatively, sustained continuous release formulations of agonist anti-trkC antibodies may be appropriate. Various formulations and devices for achieving sustained release are known in the art.

In one embodiment, dosages for an agonist anti-trkC antibody may be determined empirically in individuals who have been given one or more administration(s) of an agonist anti-trkC antibody. Individuals are given incremental dosages of an agonist anti-trkC antibody. To assess efficacy of an agonist anti-trkC antibody, an indicator of neuropathy (such as sensory neuropathy, including taxol-induced sensory neuropathy) can be followed.

Administration of an agonist anti-trkC antibody in accordance with the method in the present invention can be continuous or intermittent, depending, for example, upon the recipient's physiological condition, whether the purpose of the administration is therapeutic or prophylactic, and other factors known to skilled practitioners. The administration of an agonist anti-trkC antibody may be essentially continuous over a preselected period of time or may be in a series of spaced dose, e.g., either before, during, or after developing sensory neuropathy; before; during; before and after; during and after; before and during; or before, during, and after developing sensory neuropathy.

In some embodiments, more than one agonist anti-trkC antibody may be present. At least one, at least two, at least three, at least four, at least five different, or more agonist anti-trkC antibody can be present. Generally, those agonist anti-trkC antibodies have complementary activities that do not adversely affect each other. An agonist anti-trkC antibody can also be used in conjunction with other agents that serve to enhance and/or complement the effectiveness of the agents.

Therapeutic formulations of the agonist anti-trkC antibody used in accordance with the present invention are prepared for storage by mixing an antibody having the desired degree of purity with optional pharmaceutically acceptable carriers, excipients or stabilizers (*Remington, The Science and Practice of Pharmacy* 20th Ed. Mack Publishing (2000)), in the form of lyophilized formulations or aqueous solutions. Acceptable carriers, excipients, or stabilizers are nontoxic to recipients at the dosages and concentrations employed, and may comprise buffers such as phosphate, citrate, and other organic acids; salts such as sodium chloride; antioxidants including ascorbic acid and methionine; preservatives (such as octadecyldimethylbenzyl ammonium chloride; hexamethonium chloride; benzalkonium chloride, benzethonium chloride; phenol, butyl or benzyl alcohol; alkyl parabens, such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosacchandes, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as TWEEN™, PLURONICS™ or polyethylene glycol (PEG).

Liposomes containing the agonist anti-trkC antibody are prepared by methods known in the art, such as described in Epstein, et al., *Proc. Natl. Acad. Sci.* USA 82:3688 (1985); Hwang, et al., *Proc. Natl. Acad. Sci.* USA 77:4030 (1980); and U.S. Pat. Nos. 4,485,045 and 4,544,545. Liposomes with enhanced circulation time are disclosed in U.S. Pat. No. 5,013,556. Particularly useful liposomes can be generated by the reverse phase evaporation method with a lipid composition comprising phosphatidylcholine, cholesterol and PEG-derivatized phosphatidylethanolamine (PEG-PE). Liposomes are extruded through filters of defined pore size to yield liposomes with the desired diameter.

The active ingredients may also be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington, The Science and Practice of Pharmacy* 20th Ed. Mack Publishing (2000).

Sustained-release preparations may be prepared. Suitable examples of sustained-release preparations include semipermeable matrices of solid hydrophobic polymers containing the antibody, which matrices are in the form of shaped articles, e.g. films, or microcapsules. Examples of sustained-release matrices include polyesters, hydrogels (for example, poly(2-hydroxyethyl-methacrylate), or 'poly(v nylalcohol)), polylactides (U.S. Pat. No. 3,773,919), copolymers of L-glutamic acid and 7 ethyl-L-glutamate, non-degradable ethylene-vinyl acetate, degradable lactic acid-glycolic acid copolymers such as the LUPRON DEPOT™ (injectable microspheres composed of lactic acid-glycolic acid copolymer and leuprolide acetate), sucrose acetate isobutyrate, and poly-D-(−)-3-hydroxybutyric acid.

The formulations to be used for in vivo administration must be sterile. This is readily accomplished by, for example, filtration through sterile filtration membranes. Therapeutic agonist anti-trkC antibody compositions are generally placed into a container having a sterile access port, for example, an intravenous solution bag or vial having a stopper pierceable by a hypodermic injection needle, or a prefilled syringe.

The compositions according to the present invention may be in unit dosage forms such as tablets, pills, capsules, powders, granules, solutions or suspensions, or suppositories, for oral, parenteral or rectal administration, or administration by inhalation or insufflation.

For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preformulation composition containing a homogeneous mixture of a compound of the present invention, or a non-toxic pharmaceutically acceptable salt thereof. When referring to these preformulation compositions as homogeneous, it is meant that the active ingredient is dispersed evenly throughout the composition so that the composition may be readily subdivided into equally effective unit dosage forms such as tablets, pills and capsules. This solid preformulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer that serves to resist disintegration in the stomach and permits the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

Suitable surface-active agents include, in particular, non-ionic agents, such as polyoxyethylenesorbitans (e.g. Tween™ 20, 40, 60, 80 or 85) and other sorbitans (e.g. Span™ 20, 40, 60, 80 or 85). Compositions with a surface-active agent will conveniently comprise between 0.01 and 5% surface-active agent, and can be between 0.1 and 2.5%. It will be appreciated that other ingredients may be added, for example mannitol or other pharmaceutically acceptable vehicles, if necessary.

Suitable emulsions may be prepared using commercially available fat emulsions, such as Intralipid™, Liposyn™, Infonutrol™, Lipofundin™ and Lipiphysan™. The active ingredient may be either dissolved in a pre-mixed emulsion composition or alternatively it may be dissolved in an oil (e.g. soybean oil, safflower oil, cottonseed oil, sesame oil, corn oil or almond oil) and an emulsion formed upon mixing with a phospholipid (e.g. egg phospholipids, soybean phospholipids or soybean lecithin) and water. It will be appreciated that other ingredients may be added, for example gylcerol or glucose, to adjust the tonicity of the emulsion. Suitable emulsions will typically contain up to 20% oil, for example, between 5 and 20%. The fat emulsion can comprise fat droplets between 0.1 and 1.0 μm, particularly 0.1 and 0.5 μm, and have a pH in the range of 5.5 to 8.0.

The emulsion compositions can be those prepared by mixing a trkC agonist antibody with Intralipid™ or the components thereof (soybean oil, egg phospholipids, glycerol and water).

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as set out above. In some embodiments, the compositions are administered by the oral or nasal respiratory route for local or systemic effect. Compositions in preferably sterile pharmaceutically acceptable solvents may be nebulised by use of gases. Nebulised solutions may be breathed directly from the nebulising device or the nebulising device may be attached to a face mask, tent or intermittent positive pressure breathing machine. Solution, suspension or powder compositions may be administered, preferably orally or nasally, from devices which deliver the formulation in an appropriate manner.

Treatment efficacy can be assessed by methods well-known in the art.

Kits Comprising Antibodies, Polypeptides, and Polynucleotides of the Invention

The invention also provides kits comprising antibodies or polypeptides for use in detection and/or therapy. Accordingly, in some embodiments, the kits comprise an antibody A5. In some embodiments, the kit comprises any antibody or polypeptide described herein.

In other aspects, the kits may be used for any of the methods described herein, including, for example, to treat an individual with sensory neuropathy (in some embodiments, large-fiber sensory neuropathy), such as taxol-induced sensory neuropathy, pyridoxine-induced neuropathy, cisplatin-induced neuropathy. The kits of this invention are in suitable packaging, and may optionally provide additional components such as, buffers and instructions for use of the antibody in any of the methods described herein. In some embodiments, the kit comprises an agonist anti-trkC antibody described herein and an instruction for treating and/or preventing sensory neuropathy (such as taxol-induced sensory neuropathy, pyridoxine-induced neuropathy, or cisplatin-induced neuropathy) in an individual. In some of the embodiments, the agonist anti-trkC antibody is antibody A5.

In another aspect, the invention provides kits comprising a polynucleotide encoding an A5 polynucleotide as described herein. In some embodiments, the kits further comprise instructions for use of the polynucleotide in any of the methods described herein.

The following examples are provided to illustrate, but not to limit, the invention.

EXAMPLES

Example 1

Humanization and Affinity Maturation of Mouse Monoclonal Antibody 2256

A. General Methods

The following general methods were used in this example.

Expression Vector Used in Clone Characterization

Expression of the antibodies was under control of an IPTG inducible lacZ promotor similar to that described in Barbas (2001) *Phage display: a laboratory manual*, Cold Spring Harbor, N.Y., Cold Spring Harbor Laboratory Press pg 2.10. Vector pComb3X), however, modifications included addition and expression of the following additional domains: the human Kappa light chain constant domain and the CH1 constant domain of IgG2a human immunoglobulin. Ig gamma-2 chain C region, protein accession number P01859; Immunoglobulin kappa light chain (*homo sapiens*), protein accession number CAA09181.

Small Scale Fab Preparation

Small scale expression of Fab in 96 wells plates was carried out as follows. Starting from *E. coli* transformed with a Fab library, colonies were picked to inoculate both a master plate (agar LB+Ampicillin (50 μg/ml)+2% Glucose) and a working plate (2 ml/well, 96 well/plate containing 1.5 mL of LB+Ampicillin (50 μg/ml)+2% Glucose). Both plates were grown at 30° C. for 8-12 hours. The master plate was stored at 4° C. and the cells from the working plate were pelleted at 5000 rpm and resuspended with 1 mL of LB+Ampicillin (50 μg/ml)+1 mM IPTG to induce expression of Fabs. Cells were harvested by centrifugation after 5 h expression time at 30° C., then resuspended in 500 μL of buffer HBS-P (100 mM HEPES buffer pH 7.4, 150 mM NaCl, 0.005% P20). Lysis of HBS-P resuspended cells was attained by one cycle of freezing (−80° C.) then thawing at 37° C. Cell lysates were centrifuged at 5000 rpm for 30 min to separate cell debris from supernatants containing Fab. The supernatants were then injected into the BIAcore plasmon resonance apparatus to obtain affinity information for each Fab. Clones expressing Fab were rescued from the master plate to sequence the DNA and for large scale Fab production and detailed characterization as described below.

Large Scale Fab Preparation

To obtain detailed kinetic parameters, Fab was expressed and purified from large cultures. Erlenmeyer flasks containing 200 mL of LB+Ampicillin (50 μg/ml)+2% Glucose were inoculated with 5 mL of over night culture from a selected Fab-expressing *E. coli* clone. Clones were incubated at 30° C. until an $OD_{550nm}$ of 1.0 was attained and then induced by replacing the media for 200 ml, of LB+Ampicillin (50 μg/ml)+1 mM IPTG. After 5 h expression time at 30° C., cells were pelleted by centrifugation, then resuspended in 10 mL PBS (pH 8). Lysis of the cells was obtained by two cycles of freeze/thaw (at −80° C. and 37° C., respectively). Supernatant of the cell lysates were loaded onto Ni-NTA superflow sepharose (Qiagen, Valencia. Calif.) columns equilibrated with PBS, pH 8, then washed with 5 column volumes of PBS, pH 8. Individual Fab eluted in different fractions with PBS (pH 8)+300 mM imidazole. Fractions containing Fab were pooled and dialized in PBS, then quantified by ELISA prior to affinity characterization.

Full Antibody Preparation

For expression of full antibodies, heavy and light chain variable regions were cloned in mammalian expression vectors and transfected using lipofectamine into HEK 293 cells for transient expression. Antibodies were purified using protein A using standard methods.

Biacore Assay

Affinities of anti-trkC Fabs and monoclonal antibodies were determined using the BIAcore 3000™ surface plasmon resonance (SPR) system (BIAcore, INC, Piscaway N.J.). CM5 chips were activated with N-ethyl-N'-(3-dimethylaminopropyl)-carbodiimide hydrochloride (EDC) and N-hydroxysuccinimide (NHS) according to the supplier's instructions. Human or rat trkC-Fc fusion protein was diluted into 10 mM sodium acetate pH 5.0 and injected over the activated chip at a concentration of 0.005 mg/mL. Using variable flow time across the individual chip channels, two ranges of antigen density were achieved: 200-400 response units (RU) for detailed kinetic studies and 500-1000 RU for screening assays. The chip was blocked with ethanolamine. Regeneration studies showed that a mixture of Pierce elution buffer (Product No. 21004, Pierce Biotechnology, Rockford, Ill.) and 4 M NaCl (2:1) effectively removed the bound Fab while keeping the activity of htrkC on the chip for over 200 injections. HBS-EP buffer (0.01M HEPES, pH 7.4, 0.15 NaCl, 3 mM EDTA, 0.005% Surfactant P20) was used as running buffer for all the BIAcore assays. Serial dilutions (0.1-10× estimated $K_D$) of purified Fab samples are injected for 1 min at 100 µL/min and dissociation times of up to 2 h are allowed. The concentrations of the Fab proteins are determined by ELISA and/or SDS-PAGE electrophoresis using a Fab of known concentration (as determined by amino acid analysis) as a standard. Kinetic association rates ($k_{on}$) and dissociation rates ($k_{off}$) are obtained simultaneously by fitting the data to a 1:1 Langmuir binding model (Karlsson, R. Roos, H. Fagerstam, L. Petersson, B. (1994). Methods Enzymology 6. 99-110) using the BIAevaluation program. Equilibrium dissociation constant ($K_D$) values are calculated as $k_{off}/k_{on}$.

Screening Assay

A screening BIAcore assay was optimized to determine the affinity of Fab clones from libraries. Supernatants of small culture lysates were injected at 50 µl/min for 2 min. Dissociation times of 5 minutes were used for determination of a single exponential dissociation rate ($k_{off}$) using BIAevaluation software. Samples were injected for confirmation and dissociation times of up to 45 min were allowed to obtain better $k_{off}$ values. Clones showing improved (slower) $k_{off}$ values were expressed at large scale and full kinetic parameters, $k_{on}$ and $k_{off}$, were determined on purified protein. The assay was capable of detecting differences in affinity that were approximately 2-fold or larger.

B. Humanization and Affinity Maturation of Mouse Monoclonal Antibody 2256

Mouse monoclonal trkC agonistic antibody 2256 was selected for humanization and affinity maturation. See PTC/US01/20153 (WO 01/98361 A2). Mab 2256 has a binding affinity for human trkC of approximately 62 nM, as determined using BIAcore surface plasmon resonance. Mab 2256 has an EC50 of approximately 40 nM as assayed using the KIRA assay using human trkC, and an EC50 of approximately 5 nM as assayed using the rat trigeminal neuron survival assay as described herein.

The extended CDRs of mouse monoclonal agonist anti-trkC antibody 2256 (also termed "Mab 2256" or "2256") are shown in FIG. 2 (CDRs H2, H3, L1, L2, L3 correspond to Kabat and Chothia that are 100% coincident in these CDRs). Hi is a compromise between Kabat and Chothia and includes all the residues from both definitions). FIG. 2 also shown the Chothia and Kabat CDRs.

The following human germline acceptor sequences were used for humanizing and affinity maturing antibody 2256: human light chain acceptor germline sequence O8 (GenBank accession no. M64855; and human heavy chain acceptor germline sequence VH1-46 (GenBank accession No AB019438). The sequence of the framework region of VH1-46 and O8 is shown in FIG. 1 (in the context of antibody A5 amino acid sequences). Amino acid numbering is sequential. The following human J sequences are included in the humanized antibodies: (a) heavy chain: human JH4 (WQGTLVTVSS (SEQ ID NO:14); and (b) light chain: TFGQGTKLEIK (SEQ ID NO:15).

We prepared antibody clones bearing the CDR and/or framework region substitution mutations shown in Table 1 and determine $K_D$ and other kinetic parameters using BIAcore analysis as described herein. Substitution mutations shown in Table 1 are designated as follows: (a) for framework regions: the substitution mutation(s) are described relative to light chain acceptor germline sequence O8, or human heavy chain acceptor germline sequence VH1-46; and (b) for CDR regions: the substitution mutation(s) are described relative to the corresponding CDR sequence of Mab 2256. In Table 2, binding affinity (including $K_D$) of mutant Fabs was determined to human trkC.

Table 3 summarizes the results of kinetic analysis of Fab A5, Fab 2256 (parent), and other clones of selected mutants to rat and human trkC, as determined using BIAcore analysis.

Antibody A5 (also termed clone 129(T8)(H8xE10)(10B) (A5)) was selected for further characterization. The sequence of A5 heavy and light chain variable regions is shown in SEQ ID NOS: 1 and 2. The affinity of A5 for human trkC is 200 fold improved (with respect to the affinity of parent antibody 2256) and the affinity of A5 to rat TrkC was increased to 19 nM, a value suitable for animal studies (as compared to uM range affinity for parent antibody 2256).

TABLE 2

AMINO ACID SEQUENCES AND KINETIC DATA FOR ANTIBODY 2256 MUTANTS. BINDING TO HUMAN TRKC WAS TESTED USING BIACORE ANALYSIS.

| Clone | Light Chain Framework[2] | CDR L1 | CDR L2 | CDR L3 | Heavy Chain Framework[3] | CDR H1 | CDR H2 | CDR H3 | $k_{on}$ ($Ms^{-1}$) | $k_{off}$ ($s^{-1}$) | $K_D$ (nM) |
|---|---|---|---|---|---|---|---|---|---|---|---|
| 129(T26) | A47P | | | E97A | R72L, T74K, E82Q | | | Y106R | | $1.20E^{-3}$ | $2.3^1$ |
| 129(T34) | K46Q, A47P | | | E97T | E82Q | | | Y106R | | $1.20E^{-3}$ | $2.3^1$ |
| 129(T8) | | | | E97T | V68A, R72G, T74K | | | Y106R | | $1.60E^{-3}$ | $3.0^1$ |
| 129(C36) | A47P | | | E97A | R72L, T74K, E82Q | | | Y106R | | $2.00E^{-3}$ | $3.8^1$ |
| 129(C28) | K46Q | | | E97T | V68A, R72G, E82Q | | | Y106Q | | $1.90E^{-3}$ | $3.6^1$ |
| 129(C14) | K46Q | | | | T74K, E82H | | | Y106R | | $1.70E^{-3}$ | $3.2^1$ |
| 129(T6) | K46Q | | | | R72G, E82Q | | | Y106K | | $3.40E^{-3}$ | $6.4^1$ |
| 129(C2) | K46Q, A47P, S69T | | | | R72G, E82Q | | | Y106K | | $2.50E^{-3}$ | $4.7^1$ |
| 129(C16) | A47P, I52M | | | | R72L, E82Q | | | Y106K | | $2.50E^{-3}$ | $4.7^1$ |
| 129(C26) | K46Q | | | E97S | R72G, T74K | | | Y106S | | $7.00E^{-3}$ | $13.2^1$ |

TABLE 2-continued

AMINO ACID SEQUENCES AND KINETIC DATA FOR ANTIBODY 2256 MUTANTS.
BINDING TO HUMAN TRKC WAS TESTED USING BIACORE ANALYSIS.

| Clone | Light Chain Framework[2] | CDR L1 | CDR L2 | CDR L3 | Heavy Chain Framework[3] | CDR H1 | CDR H2 | CDR H3 | $k_{on}$ (Ms$^{-1}$) | $k_{off}$ (s$^{-1}$) | $K_D$ (nM) |
|---|---|---|---|---|---|---|---|---|---|---|---|
| 129(T8) (H8) | | N38T | Q58L | E97T | V68A, R72G, T74K | W33R, M34I | G56S | Y106R | | 6.0E$^{-4}$ | 1.2[1] |
| 129(T8) (E12) | | N31S | Q58L | E97T | V68A, R72G, T74K | M34L | G56S | Y106R | | 9.0E$^{-4}$ | 1.8[1] |
| 129(T8) (E10) | V29I, M37L, N38A | | Q58R | E97T | V68A, R72G, T74K | W33R, M34L | K65E | Y106R | | 1.6E$^{-3}$ | 3.2[1] |
| 129(T8) (H9) | | | Q58R | E97T | V68A, R72G, T74K | M34R | | Y106R | | 1.5E$^{-3}$ | 3.0[1] |
| 129(T8) (H8xE10) | V29I, M37L, N38A | | Q58R | E97T | V68A, R72G, T74K | W33R, M34I | G56S | Y106R | | 1.0E$^{-3}$ | 2.0[1] |
| 129(T8) (H8xE10) (9A) | V29I, M37L, N38A | | Q58R | E97T | V68A, T74K | W33R, M34I | G56S | Y106R | | 3.0E$^{-4}$ | 0.6[1] |
| 129(T8) (H8xE10) (4B) | V29I, M37L, N38A | | Q58R | E97T | R72G | W33R, M34I | G56S | Y106R | | 2.0E$^{-3}$ | 4.0[1] |
| 129(T8) (H8xE10) (10B) | V29I, M37L, N38A | | Q58R | E97T | | W33R, M34I | G56S | Y106R | | 8.0E$^{-4}$ | 1.6[1] |
| 129(T8) (H8xE10) (10B) (A5) | V29I, M37L, N38A | | Q58R | E97T | | W33R, M34I | G56A | S105T, Y106R | 1.3E$^6$ | 3.70E$^{-4}$ | 0.28 |
| 129(T8) (H8xE10) (10B) (C7) | V29I, M37L, N38A | | Q58R | E97T | | W33R, M34I | G56T | S105T, Y106R | 4.2E$^5$ | 4.70E$^{-4}$ | 1.1 |
| 129(T8) (H8xE10) (10B) (E2) | V29I, M37L, N38A | | Q58R | E97T | | W33R, M34I | | S105T, Y106R | 1.4E$^6$ | 3.60E$^{-4}$ | 0.25 |

[1] = $K_D$ calculated using BIAcore determined $k_{off}$ and using 2256 $k_{on}$ = 5E$^5$ 1/Ms
[2] = substitution mutants are indicated relative to the framework sequence of human light chain acceptor germline sequence O8.
The sequence of the framework region of O8 is shown in FIG. 1. Amino acid numbering is sequential.
[3] = substitution mutants are indicated relative to the framework sequence of human heavy chain acceptor germline sequence VH1-46.
The sequence of the framework region of VH1-46 is shown in FIG. 1. Amino acid numbering is sequential.
"mE$^n$" in the table means: m × 10$^n$.

TABLE 3

KINETIC DATA FOR ANTIBODY 2256 MUTANTS.
BINDING AFFINITY WAS TESTED TO RAT TRKC

| Clone | $K_{on}$ (Ms$^{-1}$) | $k_{off}$ (s$^{-1}$) | $K_D$ (nM) |
|---|---|---|---|
| 2256 (PARENT) | | | >1000 |
| 129(T8)(H8xE10) | | 9.00E$^{-2}$ | |
| 129(T8)(H8xE10)(4B) | | 0.0289 | |
| 129(T8)(H8xE10)(4B) | | 0.0627 | |
| 129(T8)(H8xE10)(10B) | | 0.01 | |
| 129(T8)(H8xE10)(10B)(A5) | 1.30E$^6$ | 0.0267 | 19 |
| 129(T8)(H8xE10)(10B)(C7) | 7.80E$^5$ | 0.03 | 39 |
| 129(T8)(H8xE10)(10B)(E2) | 1.50E$^6$ | 9.40E$^{-3}$ | 6 |

"mE$^n$" in the table means: m × 10$^n$.

C. Characterization of Humanized and Affinity Matured Antibody A5.

Antibody A5, was expressed as full IgG and its agonistic activity for human TrkC is measured by KIRA as described in Sadick et al, Exp. Cell Res. (1997) 234: 354-361, and its agonistic activity for rat TrkC was measured by neuron survival assay performed as described in the following protocol. FIGS. 3 and 4 show that antibody A5 was a potent agonist for human and rodent TrkC. EC50 for A5 in neuron survival on rodent TrkC is 0.001 nM, while for 2256 was 5 nM, in good agreement with the difference of affinity between these antibodies.

In another experiment, specificity of antibody A5 for trkC was tested by determining the binding affinity of the A5 antibody for human and rat trkA and trkB using BIAcore assay essentially as described above for trkC binding affinity. No binding of A5 was detected to human trkA, rat trkA, human trkB, or rat trkB, in contrast to the positive control (for human trkA, an anti-human trkA antibody was used; for rat trkA, human NGF was used; for human trkB, an anti-human trkB antibody was used; for rat trkB, human NT-4/5 was used).

E12 Trigeminal Rat Neuron Survival Assay

The trigeminal ganglion is comprised of cutaneous sensory neurons that innervate the facial region. These neurons are supported by BDNF and NT3 at early stages of gangliogenesis and by NGF at later stages. The trigeminal ganglion neurons obtained from E12 embryos are supported by NT3, so that at saturating concentrations of the neurotrophic factor the survival is close to 100% by 48 hours in culture. In absence of NT3, less than 5% of the neurons survive by 48 hours. Therefore, the survival of E12 trigeminal neurons is a sensitive assay to evaluate the agonistic activity of TrkC agonistic antibodies.

Time-mated pregnant Sprague Dawley female rats were euthanised by CO2 inhalation. The uterine horns were removed and the embryos at embryonic stage E12 were extracted and decapitated. The trigeminal ganglia were dissected using electrolytically sharpened tungsten needles. The ganglia were then trypsinized, mechanically dissociated and plated at a density of 200-300 cells per well in defined, serum-free medium in 96-well plates coated with poly-L-ornithine and laminin. The agonistic activity of anti TrkC antibodies was evaluated in a dose-response manner in triplicates. After 48 hours in culture the cells were subjected to an automated immunocytochemistry protocol performed on a Biomek FX liquid handling workstation (Beckman Coulter). The protocol included fixation (4% formaldehyde, 5% sucrose, PBS), permeabilization (0.3% Triton X-100 in PBS), blocking of unspecific binding sites (5% normal goat serum, 0.1% BSA, PBS) and sequential incubation with a primary and secondary antibodies to detect neurons. A rabbit polyclonal antibody against the protein gene product 9.5 (PGP9.5, Chemicon), which is an established neuronal phenotypic marker, was used as primary antibody. Alexa Fluor 488 goat anti-rabbit (Molecular Probes) was used as secondary reagent together with the nuclear dye Hoechst 33342 (Molecular Probes) to label the nuclei of all the cells present in the culture. Image acquisition and image analysis were performed on a Discovery-1/GenII Imager (Universal Imaging Corporation). Images were automatically acquired at two wavelengths for Alexa Fluor 488 and Hoechst 33342, with the nuclear staining being used as reference point, since it is present in all the wells, for the image-based auto focus-system of the Imager. Appropriate objectives and number of sites imaged per well were selected to cover the entire surface of each well. Automated image analysis was set up to count the number of neurons present in each well after 48 hours in culture based on their specific staining with the anti-PGP9.5 antibody. Careful thresholding of the image and application of morphology and fluorescence intensity based selectivity filters resulted in an accurate count of neurons per well.

Example 2

Effect of Antibody A5 on Pyridoxine-induced Neuropathy

Treatment protocol. The experiments were carried out on adult male Sprague-Dawley rats weighing 150 to 200 g at the start of the experiment, and in compliance with approved institutional animal care and use protocols. Six to eight animals were used for each treatment group. Neuropathy was induced by the injection of pyridoxine (PDX, Sigma, St. Louis, Mo.) at 100 mg/ml in distilled water immediately before injection, and administration was performed at 400 mg/kg intraperitoneally twice a day for 8 days. A5-treated animals received A5 (5 mg/kg) by intraperitoneal injection 3 days before the start of PDX treatment, and again at 1 week after the initial dose of A5. Vector-treated animals received a single subcutaneous inoculation of 25 ul of vector QL2HNT3 ($1 \times 10^9$ pfu/ml) in the plantar surface of both hind feet 3 days prior to the start of intoxication. Vector QL2HNT3 is a replication-incompetent, genomic herpes simplex virus-based vector containing coding sequence for NT-3 and is capable of transducing sensory neurons of the rat dorsal root ganglion in vivo and expressing NT-3 in these neurons. Chattopadhyay et al., *Ann. Neurol.* 51:19-27 (2002). Controls included untreated animals (control) and animals intoxicated with PDX (PDX) but receiving no other treatment.

Electrophysiological measurements. All recordings were made at day 15 after the initial does of pyridoxine. using a standard clinical electromyography device (Viking II, Nicolet Biomedical, Madison, Wis.) and Grass needle electrodes. Rats were anesthetized with chloral hydrate (400 mg/kg IP), with hindlimbs secured at an angle of 30 to 45 degrees relative to the long axis of the body, subcutaneous temperature maintained at 36 to 37 degrees, and a ground electrode inserted into the tail. Motor nerve conduction velocity and amplitude in the sciatic nerve were determined with a recording electrode inserted in the gastrocnemicus muscle. The stimulating electrode pair was placed proximal to the sciatic notch or the knee and a reference-recording electrode inserted subcutaneously into the fifth digit of the hindlimb. Both latencies and amplitudes were determined and conduction velocity was calculated. The H wave was recorded after stimulating at the sciatic notch and recording from a clip electrode placed proximal to the fifth digit. At least eight responses were obtained and the maximal H-wave amplitude was determined. For sensory nerve recordings, the electrode placed in the sciatic notch was used as the recording electrode; a stimulating electrode was placed at the ankle and the reference electrode placed at the first digit. The statistical significance of the difference between groups was determined by analysis of variance (ANOVA) (Systat 9), using Bonferroni's correction for the multiple post hoc analyses performed.

Behavioral Evaluation of Neuropathy. In order to assess the proprioceptive function, the rats were trained before intoxication to traverse a 3 cm-diameter dowel 185 cm in length. A pair of black lines 0.6 cm in width was painted along the length of the dowel, 1.05 cm lateral to the midline on each side. At 8 days after the conclusion of PDX intoxication, each rat was given five trials to cross the beam. The placement of the paw (metatarsophalangeal joint) in relation to the score line, and the number of slips from the dowel were counted from a videotape recording played at slow speed. The statistical significance of the difference between groups was determined by ANOVA (Systat 9) using Bonferroni's correction for the multiple post hoc analyses performed.

Figure 5A:
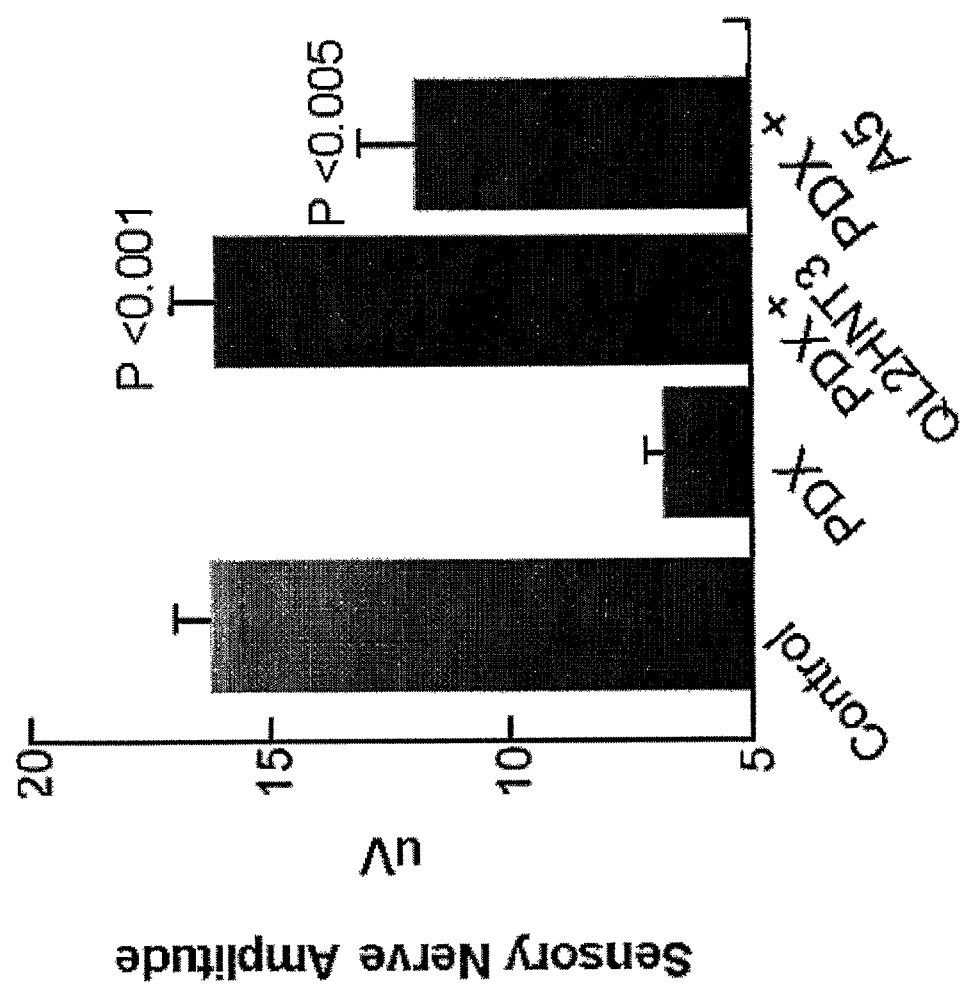
FIG. 5A: is a graph showing sensory nerve amplitude measured in control, PDX, PDX+QL2HNT3, and PDX+A5 treated animals.
Figure 5B:
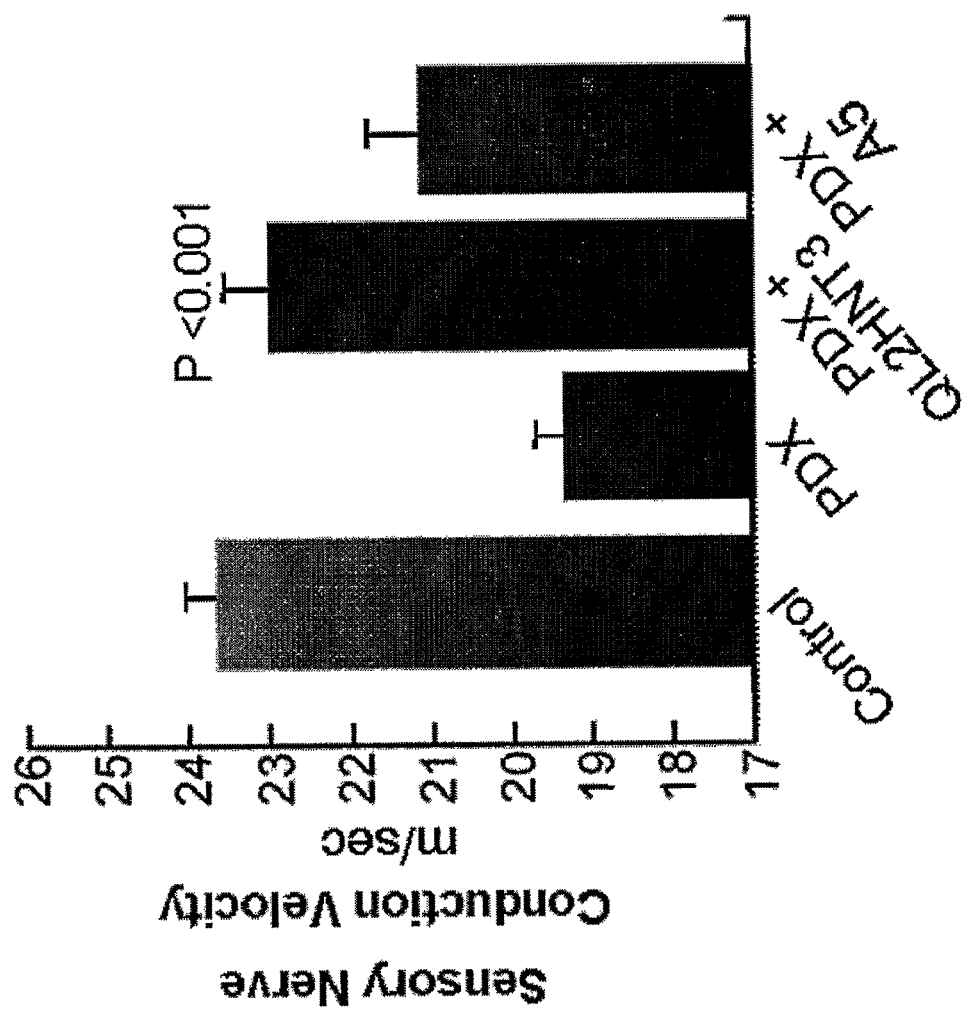
FIG. 5B: is a graph showing sensory nerve conduction velocity measured in control, PDX, PDX+QL2HNT3, and PDX+A5 treated animals.
Figure 5C:
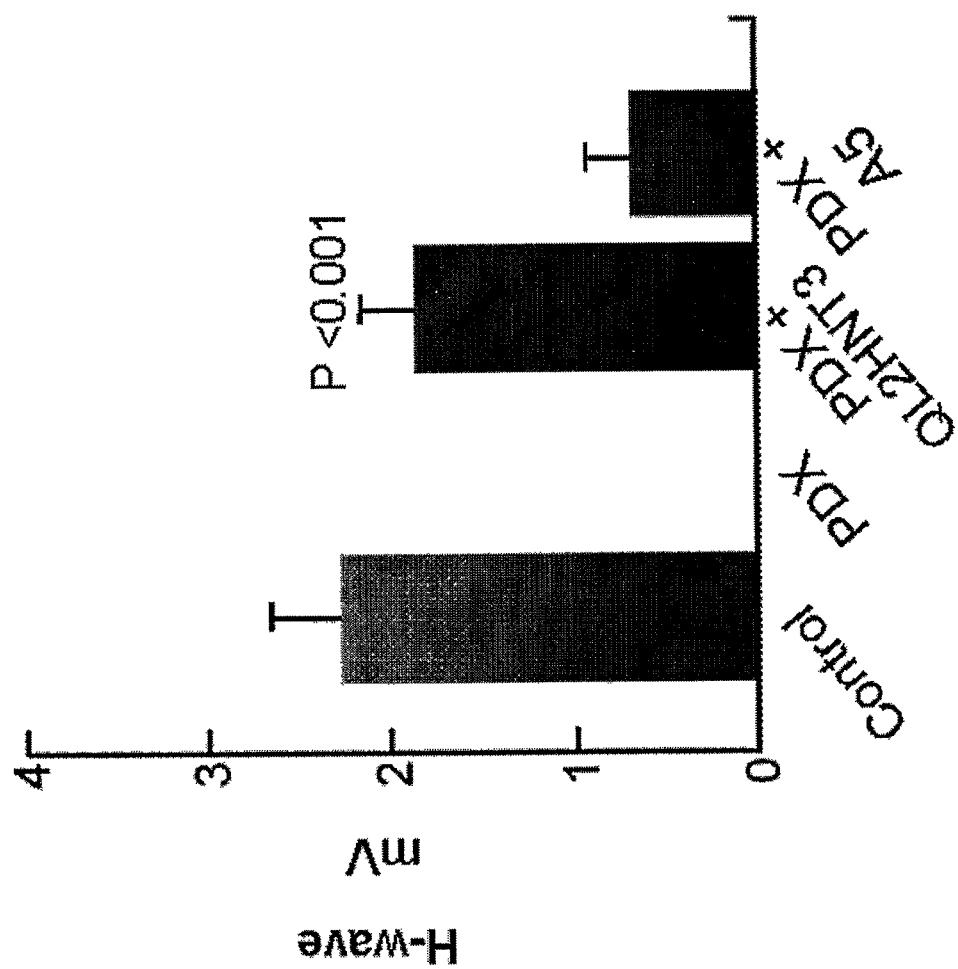
FIG. 5C: is a graph showing H-wave measured in control, PDX, PDX+QL2HNT3, and PDX+A5 treated animals.

Protection against neuropathy by antibody A5 measured by electrophysiology. As shown in FIGS. 5A and 5B, measurement of the evoked sensory nerve action potential revealed a marked decrease in amplitude and slowing of the foot sensory nerve conduction velocity in rats intoxicated with PDX compared with control. Sensory nerve amplitude was reduced from 16.2±1 μV in control animals to 6.8±0.6 μV in PDX intoxicated animals (P<0.001, ANOVA), and the conduction velocity reduced from 23.6 m/sec to 19.3 m/sec (P<0.001, ANOVA). In animals transduced with QL2HNT3 three days before intoxication with PDX, the sensory nerve amplitude was 16.1±2.4 μV (P<0.001 compared with PDX alone, ANOVA). Animals treated with A5 showed significant preservation of sensory nerve amplitude (11.9±3 μV, P<0.005, ANOVA) compared to the PDX group. Similarly, PDX-intoxicated QL2HNT3-treated animals had a sensory nerve conduction velocity (23 m/sec) that was identical to control (P<0.001 compared with PDX alone, ANOVA). PDX intoxicated animals treated with A5 had a sensory nerve conduction velocity (21.1 m/sec) that was not significantly different from the PDX-treatment group. As shown in FIG. 5C, the H reflex was severely attenuated in rats receiving PDX compared with control, while the direct M response was unattenuated as previously reported. Animals intoxicated with PDX had essentially no detectable H reflex. Animals intoxicated with PDX and treated with QL2HNT3 shows a substantial though incomplete preservation of the H wave (1.84±0.8 mV, P<0.001 PDX+QL2HNT3 compared with PDX alone, ANOVA). Animals intoxicated with PDX treated with A5 showed some preservation of H-wave (0.6±0.5 mV) but the difference was not significant compared with the PDX-intoxicated group.

Figure 5D:
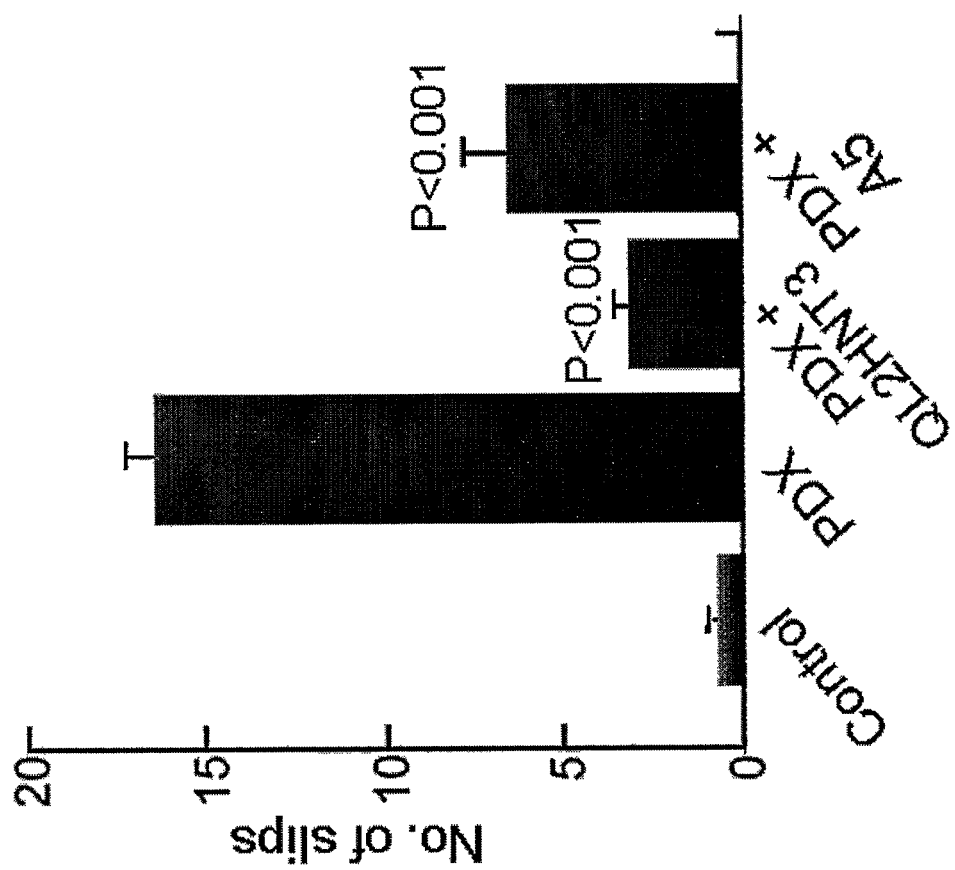
FIG. 5D: is a graph showing number of slips measured in control, PDX, PDX+QL2HNT3, and PDX+A5 treated animals.

Protection against neuropathy by antibody AS measured by behavioral performance. In order to test proprioceptive sensory function, rats were trained before PDX intoxication to walk on a 3.0 cm diameter beam, and tested at 7 days after completion of PDX treatment (15 days after the start of treatment and 18 days after vector or initial antibody inoculation) on the same beam. As shown in FIG. 5D, control animals had no difficulty traversing the beam, indicated by no slips below the score line. Animals intoxicated with PDX experienced substantial difficulty, recording an average of 16 slips from the beam during the test period. Rats transduced with QL2HNT3 3 days before PDX intoxication performed substantially better than PDX-only animals both qualitatively and quantitatively. Animals treated with QL2HNT3 recorded an average of 3 slips (P<0.001 compared with PDX-only, ANOVA). Animals that had received A5 recorded an average of 6.5 slips from the bar during the trial period, a difference that was statistically significant but smaller in magnitude than the vector-treated PDX intoxicated animals (P<0.001 compared to PDX alone).

Example 3

Effect of Antibody A5 on Ciplatin-induced Neuropathy

Treatment protocol. The experiments were carried out on female Wistar rats weighing 180-200 g (Harlan, Correzzana, Italy) at the start of the experiment. Animals were divided by computer-generated random selection into the different groups and eight animals were used for each treatment group. Neuropathy was induced by intraperitoneally (ip) injection of cisplatin (CDDP) (Bristol Meyer Squibbs, at 0.5 mg/ml in sterile saline) at 2 mg/kg twice weekly for four weeks. Group 1 animals (controls) were untreated. Group 2 animals were injected with CDDP at 2 mg/kg ip twice weekly for four weeks. Group 3 animals were injected with CDDP at 2 mg/kg ip twice weekly for four weeks and subcutaneously (sc) injected with antibody 2256 at 2 mg/kg once every 7 days. Group 4 animals were injected with CDDP at 2 mg/kg ip twice weekly for four weeks and subcutaneously injected with antibody 2256 at 10 mg/kg once every 7 days. Group 5 animals were injected with CDDP at 2 mg/kg ip twice weekly for four weeks and subcutaneously injected with antibody A5 at 2 mg/kg once every 7 days. Group 6 animals were injected with CDDP at 2 mg/kg ip twice weekly for four weeks and subcutaneously injected with antibody A5 at 10 mg/kg once every 7 days.

Neurophysiology determination. Before starting the experiment and at the end of the treatment period (4 weeks), each animal was undergone the determination of the sensory nerve conduction velocity in the tail. These methods are described in details by Pisano et al., *Clin. Cancer Res.* 9:5756-67 (2003); and Tredici et al., *Exp. Neurol.* 159:551-8 (1999). Briefly, the antidromic nerve conduction in the tail nerve was assessed by placing recording ring electrodes distally in the tail, while the stimulating ring electrodes were placed 5 cm and 10 cm proximally with respect to the recording point. The latencies of the potentials recorded at the 2 sites after nerve stimulation were determined (peak-to-peak) and nerve conduction velocity was calculated accordingly. All the neurophysiological determinations were performed under standard conditions in a temperature-controlled room adjacent to the animal housing room. The differences in nerve conduction velocity obtained in the different groups during the experiment were statistically evaluated using the analysis of variance (ANOVA) and the Tukey-Kramer post-test (significance level set at $p<0.05$).

Pathology determination. Sciatic nerve and dorsal root ganglia specimens were obtained at the study site from 4 rats from each group at the end of the treatment period (4 weeks) and pathological examination was performed as described by Tredici et al., *Exp. Neurol.* 159:551-8 (1999).

Figure 6:
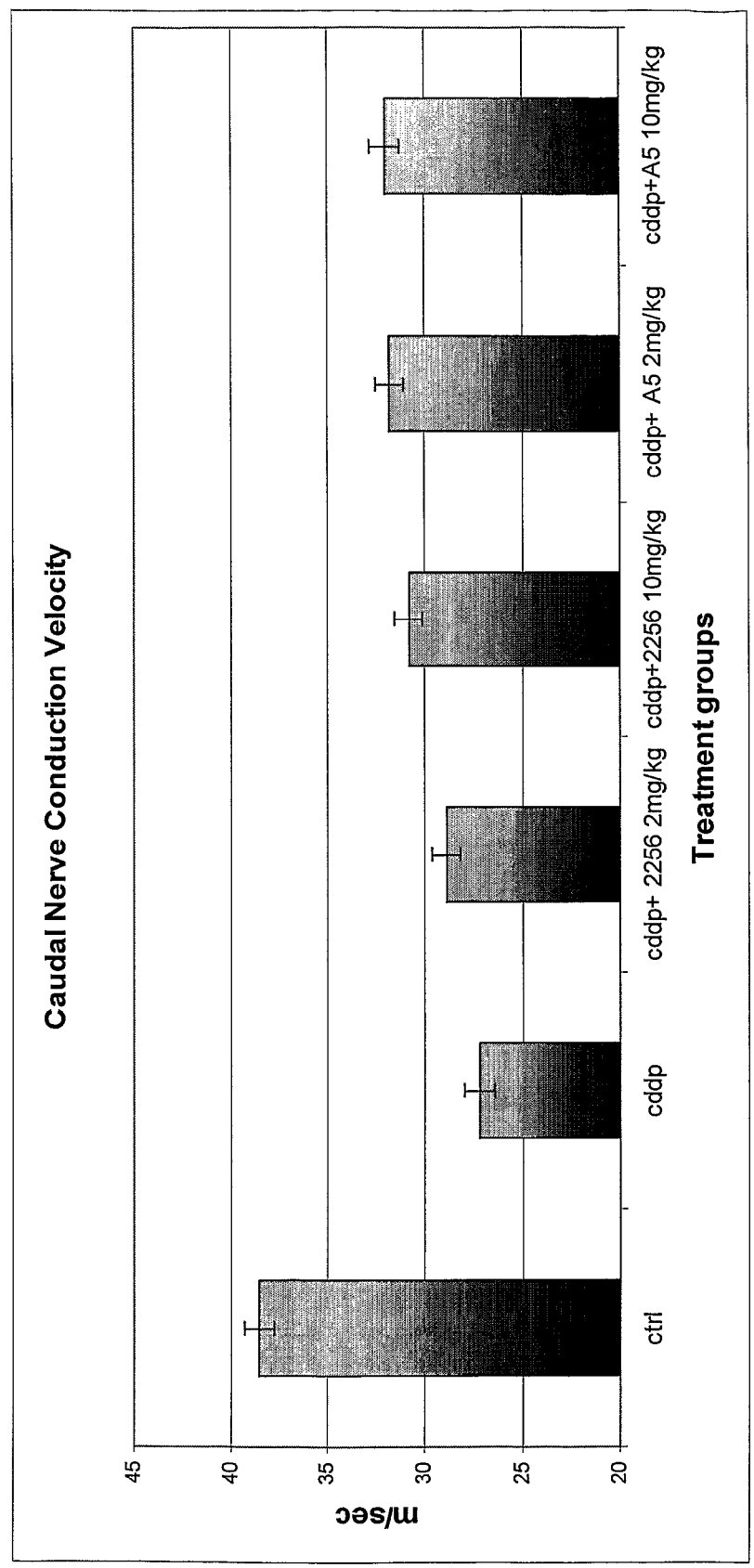
FIG. 6: is a graph showing caudal nerve conduction velocity measured in control, CDDP, CDDP+2256 (2 mg/kg), CDDP+2256 (10 mg/kg), CDDP+A5 (2 mg/kg), and CDDP+A5 (10 mg/kg) treated animals.

Effect of AS on cisplatin-induced neuropathy. As shown in FIG. 6 and Table 4 below, CDDP injection significantly ($P<0.001$) reduced caudal nerve conduction velocity by about 30% as compared to the control group. Antibody A5 at both 2 mg/kg and 10 mg/kg significantly improved caudal nerve conduction velocity. CDDP administration induced significant morphological changes with respect to the soma size, nuclear size and the area of nucleoli of the DRG neurons relative to the control group as described previously. Pisano et al., *Clin. Cancer Res.* 9:5756-67 (2003); and Tredici et al., *Exp. Neurol.* 159:551-8 (1999). However, no significant change was observed in the 2256 or A5 treated CDDP-injected rats relative to the CDDP-injected rats regarding the soma size, nuclear size or the area of nucleoli of the DRG neurons.

TABLE 4

Summary of caudal nerve conduction velocity in different treatment groups

| Treatment Groups | Control | CDDP | CDDP + 2256 (2 mg/kg) | CDDP + 2256 (10 mg/kg) | CDDP + A5 (2 mg/kg) | CDDP + A5 (10 mg/kg) |
|---|---|---|---|---|---|---|
| Mean | 38.56 | 27.22 | 28.87 | 30.8 | 31.79 | 32.02 |
| SEM | 0.7338 | 0.2056 | 0.2555 | 0.3733 | 0.4777 | 0.2934 |
| Statistics |  | P < 0.001 (compared to control group) | P > 0.05 (compared to CDDP group) | P < 0.001 (compared to CDDP group) | P < 0.001 (compared to CDDP group) | P < 0.001 (compared to CDDP group) |

One-way ANOVA (Tukey post-test) was used for statistical analysis.

Deposit of Biological Material

The following materials have been deposited with the American Type Culture Collection, 10801 University Boulevard, Manassas, Va., USA (ATCC):

| Material | | ATCC Accession No. | Date of Deposit |
|---|---|---|---|
| Eb.pur.2256.A5 | A5 light chain | PTA-5682 | Dec. 5, 2003 |
| Db.2256.A5 | A5 heavy chain | PTA-5683 | Dec. 5, 2003 |

Vector Eb.pur.2256.A5 is a polynucleotide encoding the A5 light chain variable region and the human light chain kappa constant region; and vector Db.2256.A5 is a polynucleotide encoding the A5 heavy chain variable region and the human heavy chain IgG2a constant region containing the following mutations: A330P331 to S330S331 (amino acid numbering with reference to the wildtype IgG2a sequence; see Eur. J. Immunol. (1999) 29:2613-2624).

This deposit was made under the provisions of the Budapest Treaty on the International Recognition of the Deposit of Microorganisms for the Purpose of Patent Procedure and the Regulations thereunder (Budapest Treaty). This assures maintenance of a viable culture of the deposit for 30 years from the date of deposit. The deposit will be made available by ATCC under the terms of the Budapest Treaty, and subject to an agreement between Rinat Neuroscience Corp. and ATCC, which assures permanent and unrestricted availability of the progeny of the culture of the deposit to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 USC Section 122 and the Commissioner's rules pursuant thereto (including 37 CFR Section 1.14 with particular reference to 886 OG 638).

The assignee of the present application has agreed that if a culture of the materials on deposit should die or be lost or destroyed when cultivated under suitable conditions, the materials will be promptly replaced on notification with another of the same. Availability of the deposited material is not to be construed as a license to practice the invention in contravention of the rights granted under the authority of any government in accordance with its patent laws.

Antibody Sequences

```
A5 heavy chain variable region amino acid sequence
                                                        (SEQ ID NO: 1)
QVQLVQSGAEVKKPGASVKVSCKASGYTFTSYRIHWVRQAPGQGLEWMGEIYPSNAR

TNYNEKFKSRVTMTRDTSTSTVYMELSSLRSEDTAVYYCARKYYYGNTRRSWYFDVW

GQGTTVTVS

A5 heavy chain amino acid sequence
                                                       (SEQ ID NO: 28)
QVQLVQSGAEVKKPGASVKVSCKASGYTFTSYRIHWVRQAPGQGLEWMGEIYPSNAR

TNYNEKFKSRVTMTRDTSTSTVYMELSSLRSEDTAVYYCARKYYYGNTRRSWYFDVW

GQGTTVTVSSASTKGPSVFPLAPCSRSTSESTAALGCLVKDYFPEPVTVSWNSGALTSGV

HTFPAVLQSSGLYSLSSVVTVPSSNFGTQTYTCNVDHKPSNTKVDKTVERKCCVECPPC

PAPPVAGPSVFLFPPKPKDTLMISRTPEVTCVVVDVSHEDPEVQFNWYVDGVEVHNAK

TKPREEQFNSTFRVVSVLTVVHQDWLNGKEYKCKVSNKGLPSSIEKTISKTKGQPREPQ

VYTLPPSREEMTKNQVSLTCLVKGFYPSDIAVEWESNGQPENNYKTTPPMLDSDGSFFL

YSKLTVDKSRWQQGNVFSCSVMHEALHNHYTQKSLSLSPGK

A5 light chain variable region amino acid sequence
                                                        (SEQ ID NO: 2)
DIQMTQSPSSLSASVGDRVTITCRASESIDNYGISFLAWYQQKPGKAPKLLIYAASNRGS

GVPSRFSGSGSGTDFTFTISSLQPEDIATYYCQQSKTVPRTFGQGTKLEIKRT

A5 light chain amino acid sequence
                                                       (SEQ ID NO: 29)
DIQMTQSPSSLSASVGDRVTITCRASESIDNYGISFLAWYQQKPGKAPKLLIYAASNRGS

GVPSRFSGSGSGTDFTFTISSLQPEDIATYYCQQSKTVPRTFGQGTKLEIKRTVAAPSVFIF

PPSDEQLKSGTASVVCLLNNFYPREAKVQWKVDNALQSGNSQESVTEQDSKDSTYSLS

STLTLSKADYEKHKVYACEATHQGLSSPVTKSFNRGEC

A5 CDR H1 (extended CDR)
                                                        (SEQ ID NO: 4)
GYTFTSYRIH A5 CDR H2 (extended CDR)
                                                        (SEQ ID NO: 5)
EIYPSNARTNYNEKFKS A5 CDR H3 (extended CDR)
                                                        (SEQ ID NO: 6)
KYYYGNTRRSWYFDV A5 CDR L1 (extended CDR)
```

-continued

A5 CDR L1 (extended CDR)

(SEQ ID NO: 7)
RASESIDNYGISFLA

A5 CDR L2 (extended CDR)

(SEQ ID NO: 8)
AASNRGS

A5 CDR L3 (extended CDR)

(SEQ ID NO: 9)
QQSKTVPRT

A5 Light variable domain nucleotide sequence (SEQ ID NO: 10)
GATATCCAGATGACACAGTCCCCATCCTCCCTGTCTGCCTCTGTGGGTGACCGCGTC

ACCATCACCTGCCGCGCAAGTGAGAGCATCGACAACTATGGCATTTCCTTCCTGGCC

TGGTATCAGCAGAAGCCGGGCAAAGCACCAAAACTCCTGATCTATGCTGCATCCAA

TCGGGGTTCAGGTGTCCCATCACGCTTCAGTGGCAGTGGCTCTGGTACAGATTTCAC

CTTCACCATTAGCAGCCTGCAACCAGAAGATATTGCCACTTATTACTGCCAACAGAG

TAAGACTGTGCCACGCACTTTCGGTCAAGGCACCAAGCTGGAGATCAAACGCACT

A5 Light chain full nucleotide sequence (SEQ ID NO: 11)
GATATCCAGATGACACAGTCCCCATCCTCCCTGTCTGCCTCTGTGGGTGACCGCGTC

ACCATCACCTGCCGCGCAAGTGAGAGCATCGACAACTATGGCATTTCCTTCCTGGCC

TGGTATCAGCAGAAGCCGGGCAAAGCACCAAAACTCCTGATCTATGCTGCATCCAA

TCGGGGTTCAGGTGTCCCATCACGCTTCAGTGGCAGTGGCTCTGGTACAGATTTCAC

CTTCACCATTAGCAGCCTGCAACCAGAAGATATTGCCACTTATTACTGCCAACAGAG

TAAGACTGTGCCACGCACTTTCGGTCAAGGCACCAAGCTGGAGATCAAACGCACTG

TGGCTGCACCATCTGTCTTCATCTTCCCTCCATCTGATGAGCAGTTGAAATCCGGAA

CTGCCTCTGTTGTGTGCCTGCTGAATAACTTCTATCCACGCGAGGCCAAAGTACAGT

GGAAGGTGGATAACGCCCTCCAATCCGGTAACTCCCAGGAGAGTGTCACAGAGCAG

GACAGCAAGGACAGCACCTACAGCCTCAGCAGCACCCTGACCCTGAGCAAAGCAG

ACTACGAGAAACACAAAGTCTACGCCTGCGAAGCCACCCATCAGGGCCTGAGTTCT

CCAGTCACAAAGAGCTTCAACCGCGGTGAGTGC

A5 heavy chain variable domain nucleotide sequence (SEQ ID NO: 12)
CAGGTGCAGCTGGTGCAGTCTGGTGCTGAGGTGAAGAAGCCTGGCGCTTCCGTGAA

GGTTTCCTGCAAAGCATCTGGTTACACCTTTACCAGCTATCGGATCCACTGGGTGCG

CCAAGCCCCTGGTCAAGGCCTGGAGTGGATGGGCGAAATCTACCCAAGCAACGCGC

GCACTAACTACAACGAGAAGTTCAAATCCCGGGTGACCATGACTCGCGATACCTCC

ACCAGCACTGTCTACATGGAACTGAGCTCTCTGCG-CTCTGAGGACACTGCTGTGTAT

TACTGTGCCCGCAAGTACTATTACGGCAATACGC&TCGCTCCTGGTACTTCGATGTG

TGGGGCCAGGGTACCACTGTTACCGTGTCC

A5 heavy chain full antibody
(including modified IgG2 as described herein)

(SEQ ID NO: 13)
CAGGTGCAGCTGGTGCAGTCTGGTGCTGAGGTGAAGAAGCCTGGCGCTTCCGTGAA

GGTTTCCTGCAAAGCATCTGGTTACACCTTTACCAGCTATCGGATCCACTGGGTGCG

```
-continued
CCAAGCCCCTGGTCAAGGCCTGGAGTGGATGGGCGAAATCTACCCAAGCAACGCGC

GCACTAACTACAACGAGAAGTTCAAATCCCGGGTGACCATGACTCGCGATACCTCC

ACCAGCACTGTCTACATGGAACTGAGCTCTCTGCGCTCTGAGGACACTGCTGTGTAT

TACTGTGCCCGCAAGTACTATTACGGCAATACGCGTCGCTCCTGGTACTTCGATGTG

TGGGGCCAGGGTACCACTGTTACCGTGTCCTCTGCCTCCACCAAGGGCCCATCTGTC

TTCCCACTGGCCCCATGCTCCCGCAGCACCTCCGAGAGCACAGCCGCCCTGGGCTGC

CTGGTCAAGGACTACTTCCCAGAACCTGTGACCGTGTCCTGGAACTCTGGCGCTCTG

ACCAGCGGCGTGCACACCTTCCCAGCTGTCCTGCAGTCCTCAGGTCTCTACTCCCTC

AGCAGCGTGGTGACCGTGCCATCCAGCAACTTCGGCACCCAGACCTACACCTGCAA

CGTAGATCACAAGCCAAGCAACACCAAGGTCGACAAGACCGTGGAGAGAAAGTGT

TGTGTGGAGTGTCCACCTTGTCCAGCCCCTCCAGTGGCCGGACCATCCGTGTTCCTG

TTCCCTCCAAAGCCAAAGGACACCCTGATGATCTCCAGAACCCCAGAGGTGACCTG

TGTGGTGGTGGACGTGTCCCACGAGGACCCAGAGGTGCAGTTCAACTGGTATGTGG

ACGGAGTGGAGGTGCACAACGCCAAGACCAAGCCAAGAGAGGAGCAGTTCAACTC

CACCTTCAGAGTGGTGAGCGTGCTGACCGTGGTGCACCAGGACTGGCTGAACGGAA

AGGAGTATAAGTGTAAGGTGTCCAACAAGGGACTGCCATCCAGCATCGAGAAGACC

ATCTCCAAGACCAAGGGACAGCCAAGAGAGCCACAGGTGTATACCCTGCCACCATC

CAGAGAGGAGATGACCAAGAACCAGGTGTCCCTGACCTGTCTGGTGAAGGGATTCT

ATCCATCCGACATCGCCGTGGAGTGGGAGTCCAACGGACAGCCAGAGAACAACTAT

AAGACCACCCCTCCAATGCTGGACTCCGACGGATCCTTCTTCCTGTATTCCAAGCTG

ACCGTGGACAAGTCCAGATGGCAGCAGGGAAACGTGTTCTCTTGTTCCGTGATGCA

CGAGGCCCTGCACAACCACTATACCCAGAAGAGCCTGTCCCTGTCTCCAGGAAAG

2256 CDR H1 (extended CDR)
                                                 (SEQ ID NO: 22)
GYTFTSYWMH 2256 CDR H2 (extended CDR)
                                                 (SEQ ID NO: 23)
EIYPSNGRTNYNEKFKS 2256 CDR H3 (extended CDR)
                                                 (SEQ ID NO: 24)
KYYYGNSYRSWYFDV 2256 CDR L1 (extended CDR)
                                                 (SEQ ID NO: 25)
RASESVDNYGISFMN 2256 CDR L2 (extended CDR)
                                                 (SEQ ID NO: 26)
AASNQGS 2256 CDR L3 (extended CDR)
                                                 (SEQ ID NO: 27)
QQSKEVPRT
```

It is understood that the examples and embodiments described herein are for illustrative purposes only and that various modifications or changes in light thereof will be suggested to persons skilled in the art and are to be included within the spirit and purview of this application.

What is claimed is:

1. An isolated agonist anti-trkC antibody comprising:
    (a) heavy chain CDRs (CDRHs) comprising:
        (i) a CDRH1 of the formula GYTFTSYXaaXaaH (SEQ ID NO:16), wherein Xaa at position 8 is R or W, and Xaa at position 9 is I, L, R, or M;
        (ii) a CDRH2 of the formula EIYPSNXaaRTNYNEKFXaaS (SEQ ID NO:17), wherein Xaa at position 7 is A, T, S, or G; and Xaa at position 16 is K or E, and
        (iii) a CDRH3 of the formula KYYYGNXaaXaaRSWYFDV (SEQ ID NO:18), wherein Xaa at position 7 is T or S;
    wherein Xaa at position 8 is R, Q, K, S, or Y; and
    (b) light chain CDRs (CDRL) comprising:
        (i) a CDRL1 of the formula RASESXaaDXaaYGISFXaaXaa (SEQ ID NO:19), wherein Xaa at position 6 is I or V; Xaa at position 8 is N or S; Xaa at position 14 is L or M; Xaa at position 15 is A, T, or N;
        (ii) a CDRL2 of the formula AASNXaaGS (SEQ ID NO:20), wherein Xaa at position 5 is R, L, or Q; and
        (iii) a CDRL3 of the formula QQSKXaaVPRT (SEQ ID NO:21), wherein Xaa at position 5 is T, A, S, or E;
    wherein the agonist anti-trkC antibody is not an antibody comprising (a) a heavy chain CDRs comprising a CDRH1 of SEQ ID NO:22, a CDRH2 of SEQ ID NO:23, and a CDRH3 of SEQ ID NO:24; and (b) light chain CDRs comprising a CDRL1 of SEQ ID NO:25, a CDRL2 of SEQ ID NO:26, and a CDRL3 of SEQ ID NO:27.

2. The isolated agonist anti-trkC antibody of claim 1, wherein the agonist anti-trkC antibody binds human trkC.

3. The isolated agonist anti-trkC antibody of claim 2, wherein the agonist anti-trkC antibody binds to human trkC with a $K_D$ less than about 5 nM.

4. The isolated agonist anti-trkC antibody of claim 2, wherein the agonist anti-trkC antibody further binds rodent trkC.

5. The isolated agonist anti-trkC antibody of claim 1, wherein the agonist anti-trkC antibody is a monoclonal antibody.

6. The isolated agonist anti-trkC antibody of claim 1, wherein the agonist anti-trkC antibody is a humanized antibody.

7. The isolated agonist anti-trkC antibody of claim 1, wherein the agonist anti-trkC antibody comprises a heavy chain CDRs (CDRH) comprising:
    (a) a CDRH1 region of SEQ ID NO:4;
    (b) a CDRH2 region of SEQ ID NO:5; and
    (c) a CDRH3 region of SEQ ID NO:6.

8. The isolated agonist anti-trkC antibody of claim 7, wherein the heavy chain variable region consists of the sequence of SEQ ID NO:1.

9. The isolated agonist anti-trkC antibody of claim 1, wherein the agonist anti-trkC antibody comprises a light chain CDRs (CDRL) comprising:
    (a) a CDRL1 region of SEQ ID NO:7;
    (b) a CDRL2 region of SEQ ID NO:8; and
    (c) a CDRL3 region of SEQ ID NO:9.

10. The isolated agonist anti-trkC antibody of claim 9, wherein the light chain variable region consists of the sequence of SEQ ID NO:2.

11. An isolated agonist anti-trkC antibody of claim 1, wherein the agonist anti-trkC antibody comprises
    (a) CDRHs comprising:
        (i) a CDRH1 of SEQ ID NO:4;
        (ii) a CDRH2 of SEQ ID NO:5; and
        (iii) a CDRH3 of SEQ ID NO:6; and
    (b) CDRLs comprising:
        (i) a CDRL1 of SEQ ID NO:7;
        (b) a CDRL2 of SEQ ID NO:8; and
        (c) a CDRL3 of SEQ ID NO:9.

12. The isolated agonist anti-trkC antibody of claim 11, wherein the heavy chain variable region consists of SEQ ID NO:1, and the light chain variable region consists of the sequence of SEQ ID NO:2.

13. The isolated agonist anti-trkC antibody of claim 11, wherein the heavy chain consists of the sequence of SEQ ID NO:28, and the light chain variable region consists of the sequence of SEQ ID NO:29.

14. A pharmaceutical composition comprising (a) an effective amount of the agonist anti-trkC antibody of claim 1 and (b) a pharmaceutical acceptable excipient.

15. A kit comprising the agonist anti-trkC antibody of claim 1.

16. An isolated polypeptide that binds to trkC, comprising:
    (a) a CDRH1 of the formula GYTFTSYXaaXaaH (SEQ ID NO:16), wherein Xaa at position 8 is R or W, and Xaa at position 9 is I, L, R, or M;
    (b) a CDRH2 of the formula EIYPSNXaaRTNYNEKFXaaS (SEQ ID NO:17), wherein Xaa at position 7 is A, T, S, or G; and Xaa at position 16 is K or E; and
    (c) a CDRH3 of the formula KYYYGNXaaXaaRSWYFDV (SEQ ID NO:18), wherein Xaa at position 7 is T or S; wherein Xaa at position 8 is R, Q, K, S, or Y;
    wherein the polypeptide is not a polypeptide comprising CDRHs comprising a CDRH1 region of SEQ ID NO:22, a CDRH2region of SEQ ID NO:23, and a CDRH3 region of SEQ ID NO:24; and further comprising:
    (d) a CDRL1 of the formula RASESXaaDXaaYGISFXaaXaa (SEQ ID NO:19), wherein Xaa at position 6 is I or V; Xaa at position 8 is N or S; Xaa at position 14 is L or M; Xaa at position 15 is A, T, or N;
    (e) a CDRL2 of the formula AASNXaaGS (SEQ ID NO:20), wherein Xaa at position 5 is R, L, or Q; and
    (f) a CDRL3 of the formula QQSKXaaVPRT (SEQ ID NO:21), wherein Xaa at position 5 is T, A, S, or E;
    wherein the polypeptide is not a polypeptide comprising CDRLs comprising a CDRL1 region of SEQ ID NO:25, a CDRL2 region of SEQ ID NO:26, and a CDRL3 region of SEQ ID NO:27.

* * * * *